United States Patent
Trieselmann et al.

(10) Patent No.: US 11,583,532 B2
(45) Date of Patent: Feb. 21, 2023

(54) TRIAZOLOPYRIMIDINE DERIVATIVES FOR USE AS GHRELIN O-ACYL TRANSFERASE (GOAT) INHIBITORS

(71) Applicant: Boehringer Ingelheim International GmbH, Ingelheim am Rhein (DE)

(72) Inventors: Thomas Trieselmann, Mettenberg (DE); Cedrickx Godbout, Attenweiler (DE); Christoph Hoenke, Biberach an der Riss (DE); Viktor Vintonyak, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 193 days.

(21) Appl. No.: 16/966,493

(22) PCT Filed: Jan. 28, 2019

(86) PCT No.: PCT/EP2019/051994
§ 371 (c)(1),
(2) Date: Jul. 31, 2020

(87) PCT Pub. No.: WO2019/149660
PCT Pub. Date: Aug. 8, 2019

(65) Prior Publication Data
US 2021/0038603 A1    Feb. 11, 2021

(30) Foreign Application Priority Data
Feb. 2, 2018  (EP) ..................................... 18154831

(51) Int. Cl.
| | | |
|---|---|---|
| A61K 31/519 | (2006.01) | |
| C07D 487/04 | (2006.01) | |
| A61P 3/04 | (2006.01) | |
| C07D 471/04 | (2006.01) | |

(52) U.S. Cl.
CPC .............. *A61K 31/519* (2013.01); *A61P 3/04* (2018.01); *C07D 471/04* (2013.01)

(58) Field of Classification Search
CPC ........................... A61K 31/519; C07D 487/04
USPC ........................ 514/262.1; 544/263
See application file for complete search history.

(56) References Cited

U.S. PATENT DOCUMENTS

| | | |
|---|---|---|
| 2008/0275057 A1 | 11/2008 | Kawabe |
| 2011/0078154 A1 | 3/2011 | Rickman et al. |
| 2012/0009560 A1 | 1/2012 | Coupe et al. |
| 2015/0018547 A1 | 1/2015 | Takakura et al. |
| 2021/0038603 A1 | 2/2021 | Trieselmann et al. |
| 2021/0040077 A1 | 2/2021 | Trieselmann et al. |

FOREIGN PATENT DOCUMENTS

| | | |
|---|---|---|
| JP | 2004516327 A | 6/2004 |
| JP | 2008538759 A | 11/2008 |
| JP | 2010526083 A | 7/2010 |
| WO | 02051845 A2 | 7/2002 |
| WO | 2006114405 A2 | 11/2006 |
| WO | 2008152403 | 6/2008 |
| WO | 2008101017 | 8/2008 |
| WO | 2008134690 A1 | 11/2008 |
| WO | 2008141843 A1 | 11/2008 |
| WO | 2010007255 | 1/2010 |
| WO | 2010007251 | 6/2010 |
| WO | 2010007253 | 6/2010 |
| WO | 2010070252 | 6/2010 |
| WO | 2011006497 | 1/2011 |
| WO | 2011114148 A1 | 9/2011 |
| WO | 2011160630 | 12/2011 |
| WO | 2011160633 | 12/2011 |
| WO | 2013092703 | 6/2013 |
| WO | 2004082383 | 8/2013 |
| WO | 2013125732 A1 | 8/2013 |
| WO | 2013192388 | 12/2013 |
| WO | 2014041195 | 3/2014 |
| WO | 2015073281 A1 | 5/2015 |
| WO | 2016044467 | 3/2016 |
| WO | 2016123275 | 8/2016 |
| WO | 2016168222 | 10/2016 |
| WO | 2016168225 | 10/2016 |
| WO | 2017070680 A1 | 4/2017 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Hirozane, Identification and Characterization of a new series of Ghrelin O-Acyl Transferase Inhibitors, SLAS Discoery, 2017.
Haffner, Intensive Lifestyle Intervention or Metofrmin on Inflammation and Coagulation in Participants with Impaired Glucose Tolerance, The Diabetes Prevention Research Group, vol. 54, 2007.
Cummings, A preprandial rise in plasma ghrelin, Diabetes, vol. 50, 2001.
Druce, Ghrelinincreases foodintake in obese as well as lean subjects, Int J. of Obesity, vol. 29, 2005.

(Continued)

*Primary Examiner* — Douglas M Willis
(74) *Attorney, Agent, or Firm* — David L. Kershner

(57) ABSTRACT

The present invention relates to compounds of general formula I, wherein the groups $R^1$ and $R^2$ are defined as in claim 1, which have valuable pharmacological properties, in particular bind to ghrelin O-acyl transferase (GOAT) and modulate its activity. The compounds are suitable for treatment and prevention of diseases which can be influenced by this receptor, such as metabolic diseases, in particular obesity.

23 Claims, No Drawings

(56) References Cited

FOREIGN PATENT DOCUMENTS

| WO | 2018024653 | | 2/2018 | |
| WO | 201844663 A1 | | 3/2018 | |
| WO | 2019149657 A1 | | 8/2019 | |
| WO | 2019149658 A1 | | 8/2019 | |
| WO | 2019149659 A1 | | 8/2019 | |
| WO | WO-2019149660 A1 | * | 8/2019 | ........... A61K 31/519 |

OTHER PUBLICATIONS

Zhang, Effect of Des0acyl Ghrelinon Adiposity and Glucose Metabolism, Endocrinology, 2008.

Wierup, The ghrelin cell, Regulatory peptides, vol. 107, 2002.

Broglio, Non-AcelatedGhrelin Counteracts the metabolic but not the neuroendocrine response, J of Endocrine & Metabolism, vol. 80, 2004.

Delparigi, High circulating Ghrelin, J. of Endocrinology & Metabolism, vol. 12, 2002.

Granata, Acylated and Unacylated Ghrelin promote Proliferation and and inhibit Apositis of pancreatic B-cells and Human Islets, Endocrinology, vol. 2, 2007.

Granata, Des-Acyl Ghrelin Fragment and analogues promote survival of pancreatic b-cells, ACS, vol. 55, 2012.

Andianov, Synthesis and Properties of 4-aminoo-3-cyanofurazan, Chem of heterocytic Compunds, vol. 30, 1994.

International Search Authority and Written opinion, for PCT/EP2017/069274, dated Sep. 15, 2017.

Kuppens, "Elelvated Ration of acylated to unacylated ghrelin in children and yoiung adults with Prader-Willi syndrome", Endocrine, Humana Press, vol. 50, No. 3, 2015, p. 633-642.

Vasil. Russian Chern Bulletin, Reactions of cyanoturazans with [beta]-dicarbonyl compiunds, 2001, vol. 50, p. 1280-1286.

Hirozane, SLAS Discovery, Identification and Charactierization of a new series of Ghrelin O-Acyl Transferase Inhibitors, vol. 23, 2018.

Vasil, Mendellev Communications, Effective Synthesis of Funtionalized furazano, 1994, vol. 2, p. 57-58.

Pagoria, Synthesisand Characterization of mutlicyclic oxadiazoles, Chem. of Heterocyclic Compunds, vol. 53, 2017, p. 760-778.

Bohle, Nucelophilic Addition of Hydroxylamine, J. Org Chem, 2000.

Vasil'ev, Effective Synthesis of Functionalized Furazano, Zelinsky Institute of Organix Chem., 1993.

Vasil'ev, Reaction of Cyanofurans, Russian Chem. Bulletin, vol. 50, 2001, p. 1280-1286.

Ichikawa, Central Research Labs, A new Synthesis of Adenine and 4-Aminoimdazole-5-carboxamide, 1965.

International Search Report for PCT/EP2021/063090 dated Jul. 1, 2021.

International Search Report for PCT/EP2021/063088 dated Jul. 1, 2021.

* cited by examiner

TRIAZOLOPYRIMIDINE DERIVATIVES FOR USE AS GHRELIN O-ACYL TRANSFERASE (GOAT) INHIBITORS

FIELD OF THE INVENTION

The present invention relates to novel triazolopyrimidine derivatives, that are inhibitors of the ghrelin O-acyl transferase (GOAT), to processes for their preparation, to pharmaceutical compositions containing these compounds and to their medical use for the prophylaxis and/or treatment of diseases which can be influenced by the modulation of the function of the ghrelin O-acyl transferase (GOAT). Particularly, the pharmaceutical compositions of the invention are suitable for the prophylaxis and/or therapy of metabolic diseases, such as obesity, including, but not limited to obesity in patients suffering from Prader-Willi-Syndrome (PWS), insulin resistance and diabetes, particularly type 2 diabetes.

BACKGROUND OF THE INVENTION

Ghrelin 0-Acyltransferase (GOAT) is a member of the membrane-bound O-acyl transferase (MBOAT) protein family, and the only enzyme in humans capable of promoting an acylation reaction on the peptide hormone ghrelin. By linking a medium-chain fatty acid to the Serine-3 position of the 28-amino acid peptide, GOAT converts unacylated ghrelin (UAG) to acylated ghrelin (AG) which is the natural ligand of the ghrelin receptor GHSR1a (growth hormone secretagogue receptor 1a). The ghrelin receptor is expressed in various areas of the brain involved in energy homeostasis. Activation of the receptor by AG results in stimulation of neuronal pathways leading to increased food intake, fat deposition and weight gain thus linking the ghrelin system to obesity. In humans, AG in plasma peaks immediately before mealtimes and drops in response to food intake (D. E. Cummings et al., Diabetes (2001) 50(8), 1714-1719). Infusion of AG has been shown to increase food intake in lean and obese subjects (M. R. Druce et al., Int. J. Obes. (2005), 29(9), 1130-1136). So far no receptor has been identified for UAG, but it has been shown to have functional antagonistic effects to AG at least with respect to its metabolic properties (W. Zhang et al., Endocrinology (2008) 149 (9), 4710-4716). Since an inhibitor of GOAT would substantially diminish the level of the GHSR1a ligand AG and concomitantly increase the functional antagonist UAG, it would be useful for the treatment of obesity as an adjunct to a reduced-calorie diet and increased physical activity for chronic weight management.

Insatiable hunger and severe obesity are characteristic features of the Prader-Willi-Syndrome (PWS), a genetically caused orphan disease with a complex pathology. AG levels in plasma of PWS subjects are elevated and AG/UAG ratios are increased suggesting a causal relationship (N. Wierup et al., Regulatory Peptides (2002) 107, 63-69; R. J. Kuppens et al., Endocrine (2015) 50(3), 633-642). Therefore GOAT inhibitors may be effective in reducing food craving behavior and body weight in PWS patients ameliorating one major burden affecting the patients and their families.

Furthermore the ghrelin system seems to play a major role in glucose homeostasis. Administration of AG to human subjects leads to suppression of glucose-induced insulin secretion and an increase in plasma glucose. Infusion of UAG is able to counteract the hyperglycemic effect of AG (F. Broglio et al., J. Clin. Endocrinol. Metab. (2004) 89, 3062-3065). The expression of GOAT, ghrelin and GHSR1a in human pancreatic islets suggests a paracrine role on insulin secretion (A. DelParigi et al., J. Clin. Endocrinol. Metab. (2002) 87(12), 5461-5464). In addition UAG promotes pancreatic β-cell and human islet cell survival in vitro (R. Granata et al., Endocrinology (2007) 148(2), 512-529) and prevents diabetes in streptozotocin treated rats (R. Granata et al., J. Med. Chem. (2012) 55(6), 2585-2596). Thus treatment with a GOAT inhibitor is expected to improve glucose homeostasis in patients with type 2 diabetes or obese with impaired glucose tolerance.

Ghrelin O-acyl transferase (GOAT) inhibitors are known in the art, see for example the compounds disclosed in WO 2013/125732 and WO 2015/073281. The triazolopyrimidine derivatives of the present invention are structurally quite different and may provide several advantages, such as enhanced potency, high metabolic and/or chemical stability, high selectivity and tolerability, enhanced solubility, the ability to cross the blood-brain barrier and the possibility to form stable salts.

Triazolopyrimidine derivatives for combating nematode diseases of plants are described in WO 2004/082383.

SUMMARY OF THE INVENTION

The object of the present invention is to provide new compounds, hereinafter described as compounds of formula I, in particular new triazolopyrimidine derivatives, which are active with regard to the ghrelin O-acyl transferase (GOAT), notably they are ghrelin O-acyl transferase (GOAT) inhibitors.

A further object of the present invention is to provide new compounds, in particular triazolopyrimidine derivatives, which have an inhibiting effect on ghrelin O-acyl transferase (GOAT) in vitro and/or in vivo and possess suitable pharmacological and pharmacokinetic properties to use them as medicaments.

A further object of the present invention is to provide effective ghrelin O-acyl transferase (GOAT) inhibitors, in particular for the treatment of metabolic disorders, for obesity, including, but not limited to obesity in patients suffering from Prader-Willi-Syndrome (PWS), insulin resistance and diabetes, in particular type 2 diabetes mellitus.

A further object of the present invention is to provide methods for treating a disease or condition mediated by the inhibition of ghrelin O-acyl transferase (GOAT) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

In a first aspect, the invention relates to a compound of formula

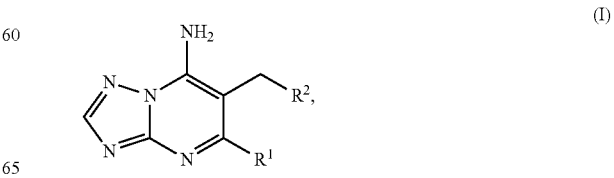

(I)

wherein

R$^1$ is selected from the group R$^1$-G1 consisting of Cl, Br, CN and CH$_3$,
  wherein the CH$_3$ group is optionally substituted with 1-3 F or with one OH;

R$^2$ is selected from the group R$^2$-G1 consisting of a phenyl and a pyridinyl group,
  which are each substituted with one fluoro-containing substituent R$^3$ selected from the group R$^3$-G1 consisting of:
  C$_{1-6}$-alkyl, which is substituted with one or more F;
  C$_{3-7}$-cycloalkyl, which is substituted with one or more F and optionally additionally substituted with one CN;
  —O—(C$_{1-6}$-alkyl), which is substituted with one or more F;
  —O—(C$_{1-3}$-alkyl)-(C$_{3-7}$-cycloalkyl), which is substituted in the cycloalkyl moiety with one or more F and/or with one mono- or polyfluorinated C$_{1-3}$-alkyl group;
  —S—(C$_{1-3}$-alkyl), which is substituted with one or more F;
  —S(=O)—(C$_{1-3}$-alkyl), which is substituted with one or more F;
  —SO$_2$—(C$_{1-3}$-alkyl), which is substituted with one or more F;
  —NH—(C$_{1-3}$-alkyl), which is substituted with one or more F;
  —NH—(C$_{1-4}$-alkyl)-(C$_{3-7}$-cycloalkyl), which is substituted in the cycloalkyl moiety with one or more F;
  —NH—(C$_{3-7}$-cycloalkyl), which is substituted in the cycloalkyl moiety with one or more F;
  —C(=O)—O—(C$_{1-4}$-alkyl), which is substituted with one or more F;
  heterocyclyl, which is substituted with one or more F and/or with one mono- or polyfluorinated C$_{1-3}$-alkyl group and which may additionally be substituted with one OH; and
  heteroaryl, which is substituted with one or more F and/or with one mono- or polyfluorinated C$_{1-3}$-alkyl group and which may additionally be substituted with one C$_{1-3}$-alkyl group;
    wherein each heterocyclyl group is selected from a 4- to 7-membered monocyclic cycloalkyl group, in which 1, 2 or 3 CH$_2$-groups are independently of each other replaced by O, S, NH or C=O; and
    wherein a phenyl ring may be condensated to any 5- to 7-membered heterocycle; and
    wherein each heteroaryl group is selected from a 5-membered aromatic cycle containing 1, 2 or 3 heteroatoms independently selected from N, O and S or from a 6-membered aromatic cycle containing 1 or 2 N;
  and which may additionally be substituted with 1 or 2 substituents R$^4$ independently of each other selected from the group R$^4$-G1 consisting of:
  F, Cl, Br, I, CN, C$_{3-7}$-cycloalkyl, OH, —O—(C$_{1-6}$-alkyl), —O—(C$_{1-3}$-alkyl)-(C$_{3-7}$-cycloalkyl), —O—(C$_{1-3}$-alkyl)-heterocyclyl, —O—(C$_{3-7}$-cycloalkyl), —O-heterocyclyl, —SO$_2$—(C$_{1-3}$-alkyl), —C(=O)—NH$_2$, —C(=O)—NH(C$_{1-3}$-alkyl), —C(=O)—N(C$_{1-3}$-alkyl)$_2$, —C(=O)OH, —C(=O)—O—(C$_{1-4}$-alkyl), —NH$_2$, —NH—(C$_{1-4}$-alkyl), —NH—(C$_{1-4}$-alkyl)-(C$_{3-7}$-cycloalkyl), —NH—(C$_{3-7}$-cycloalkyl), —N=S(=O)(C$_{1-3}$-alkyl)$_2$, heterocyclyl and heteroaryl,
    wherein the alkyl groups of the —N=S(=O)(C$_{1-3}$-alkyl)$_2$ group may be linked and together with the S atom, to which they are attached, form a 4 membered thio-heterocycle,
    wherein each alkyl group is optionally substituted with 1-3 F or with one OH, CN, COOH or —C(=O)—NH$_2$;
    wherein each cycloalkyl group is optionally substituted with one or two F and/or with one CN or —CH$_3$, which is optionally substituted with 1-3 F;
    wherein each heterocyclyl group is selected from a mono- or spirocyclic 4-to 7-membered cycloalkyl group, in which 1, 2 or 3 CH$_2$-groups are independently of each other replaced by O, S, NH or C=O,
    wherein each heterocyclyl group is optionally substituted with 1 to 3 substituents independently of each other selected from F, CN, OH and C$_{1-3}$-alkyl, which is optionally substituted with one or more F; and
    wherein each heteroaryl group is selected from a 5-membered aromatic cycle containing 1, 2 or 3 heteroatoms independently selected from N, O and S or from a 6-membered aromatic cycle containing 1 or 2 N, and
    wherein each heteroaryl group is optionally substituted with 1 or 2 substituents independently of each other selected from a group consisting of F, CN and C$_{1-3}$-alkyl, which is optionally substituted with one or more F;

wherein each of the above-mentioned alkyl groups may be substituted with one or more F;

the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, R-G1 defines genus 1 of the substituent R.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by inhibiting ghrelin O-acyl transferase (GOAT) in a patient in need thereof characterized in that a compound of general formula I or a pharmaceutically acceptable salt thereof is administered to the patient.

According to another aspect of the invention, there is provided a method for treating a metabolic disease or disorder, such as obesity, including, but not limited to obesity in patients suffering from Prader-Willi-Syndrome, insulin resistance and diabetes, in particular type 2 diabetes mellitus, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the inhibition of ghrelin O-acyl transferase (GOAT) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the inhibition of ghrelin O-acyl transferase (GOAT).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION OF THE INVENTION

Unless otherwise stated, the groups, residues, and substituents, particularly $R^1$, $R^2$, $R^3$ and $R^4$, are defined as above and hereinafter. If residues, substituents, or groups occur several times in a compound, such as $R^3$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

In one embodiment the group $R^1$ is selected from the group $R^1$-G2 consisting of Cl, $CH_2OH$ and $CH_3$,
wherein the $CH_3$ group is optionally substituted with 1-3 F.

$R^1$-G3:

In one embodiment the group $R^1$ is selected from the group $R^1$-G3 consisting of Cl, $CH_3$, $-CH_2F$, $-CHF_2$ and $CF_3$.

$R^1$-G4:

In another embodiment the group $R^1$ is selected from the group $R^1$-G4 consisting of Cl, $CH_3$ and $-CHF_2$.

$R^1$-G5:

In another embodiment the group $R^1$ is selected from the group $R^1$-G5 consisting of $-CH_3$ and Cl.

$R^1$-G6:

In another embodiment the group $R^1$ is selected from the group $R^1$-G6 consisting of $CH_3$.

$R^2$:

$R^2$-G1:

The group $R^2$ is preferably selected from the group $R^2$-G1 as defined hereinbefore.

$R^2$-G2:

In another embodiment the group $R^2$ is independently of each other selected from the group $R^2$-G2 consisting of:

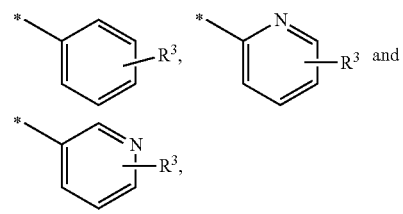

which may each additionally be substituted by one or two substituents $R^4$.

Preferably, $R^3$ is selected from the group $R^3$-G2 or $R^3$-G3 as defined in this application and $R^4$ is selected from the group $R^4$-G2 or $R^4$-G3 as defined in this application.

$R^2$-G3:

In another embodiment the group $R^2$ is independently of each other selected from the group $R^2$-G3 consisting of:

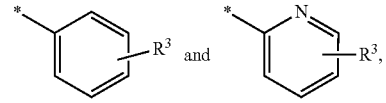

which are each optionally substituted by one or two substituents $R^4$.

Preferably, $R^3$ is selected from the group $R^3$-G2 or $R^3$-G3 as defined in this application and $R^4$ is selected from the group $R^4$-G2 or a combination of the groups $R^4$-G3a and $R^4$-G3b as defined in this application.

Preferably, the substituent $R^3$ is attached to position 3 or 4 of the phenyl or pyridinyl ring.

$R^2$-G3a:

In another embodiment the group $R^2$ is independently of each other selected from the group $R^2$-G3a consisting of:

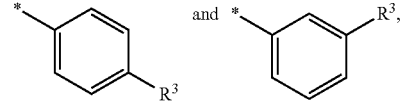

which are each optionally substituted by one or two substituents $R^4$.

Preferably, $R^3$ is selected from the group $R^3$-G3 or $R^3$-G4 as defined in this application and $R^4$ is selected from a combination of the groups $R^4$-G3a and $R^4$-G3b or from the group $R^4$-G4 as defined in this application.

$R^2$-G4:

In another embodiment the group $R^2$ is independently of each other selected from the group $R^2$-G4 consisting of:

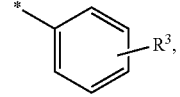

which is optionally additionally substituted by one substituent $R^4$.

Preferably, $R^3$ is selected from the group $R^3$-G3 or $R^3$-G4a as defined in this application and $R^4$ is selected from the group $R^4$-G3a or $R^4$-G4a as defined in this application.

Preferably, the substituent $R^4$ is located in position 3 or 4 of the phenyl ring.

R²-G4a:

In another embodiment the group R² is independently of each other selected from the group R²-G4a consisting of:

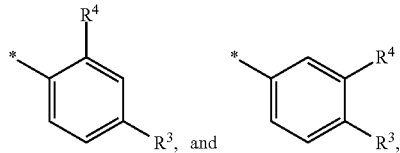

wherein R³ is selected from one of the groups R³-G3 and R³-G4a and R⁴ is either H or is selected from one of the groups R⁴-G3a and R⁴-G4a.

Preferably, R³ is from the groups R³-G3a and R⁴ is either selected form the group R⁴-G4a as defined in this application, or R⁴ is H.

R²-G5:

In another embodiment the group R² is independently of each other selected from the group R²-G5 consisting of:

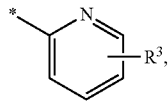

which is optionally additionally substituted by one substituent R⁴.

Preferably, R³ is selected from the group R³-G3a or R³-G4b as defined in this application and, if present, R⁴ is preferably selected from the group R⁴-G3b or R4-G4b as defined in this application.

Preferably, the substituent R³ and, if present, the substituent R⁴ are located in the following positions:

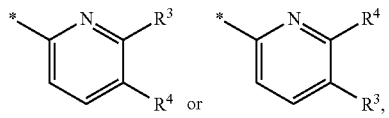

R²-G6:

In another embodiment the group R² is independently selected from the group R²-G6 consisting of:

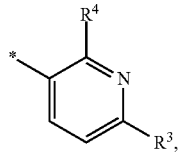

wherein
R³ is selected from one of the groups R³-G5 to R³-G4c and R⁴ is either H or is selected from one of the groups R⁴-G3b and R⁴-G4b2.

Preferably, R³ is selected from the group R³-G4c as defined in this application, and R⁴ is either selected from the group R⁴-G4b2, or R⁴ is H.

R³

R³-G1:

The group R³ is preferably selected from the group R³-G1 as defined hereinbefore.

R³-G2:

In another embodiment the group R³ is selected from the group R³-G2 consisting of:
- $C_{1-3}$-alkyl, which is substituted with one or more F;
- $C_{3-6}$-cycloalkyl, which is substituted with one or more F and optionally additionally substituted with one CN;
- —O—($C_{1-4}$-alkyl), which is substituted with one or more F;
- —O—$CH_2$—($C_{3-6}$-cycloalkyl), which is substituted in the cycloalkyl moiety with one or more F and/or with one mono- or polyfluorinated $C_{1-3}$-alkyl group;
- —S—($C_{1-3}$-alkyl), which is substituted with one or more F;
- —S(=O)—($C_{1-3}$-alkyl), which is substituted with one or more F;
- —$SO_2$—($C_{1-3}$-alkyl), which is substituted with one or more F;
- —NH—($C_{1-3}$-alkyl), which is substituted with one or more F;
- —NH—$CH_2$—($C_{3-6}$-cycloalkyl), which is substituted in the cycloalkyl moiety with one or more F;
- —NH—($C_{3-6}$-cycloalkyl), which is substituted in the cycloalkyl moiety with one or more F;
- —C(=O)—O—($C_{1-4}$-alkyl), which is substituted with one or more F; heterocyclyl, which is substituted with one or more F and/or with one mono- or polyfluorinated $C_{1-3}$-alkyl group and which may additionally be substituted with one OH; and heteroaryl, which is substituted with one or more F and/or with one mono- or polyfluorinated $C_{1-3}$-alkyl group and which may additionally be substituted with one $C_{1-3}$-alkyl group;
  wherein each heterocyclyl group is selected from a group consisting of oxetanyl, tetrahydrofuranyl, tetrahydropyranyl, azetidinyl, pyrrolidinyl, piperidinyl, piperazinyl, morpholinyl and 2,3-dihydro-1H-isoindol-1-yl; and
  wherein each heteroaryl group is selected from a 5-membered aromatic cycle containing 1 or 2 heteroatoms independently selected from N, O and S.

R³-G3:

In another embodiment the group R³ is selected from the group R³-G3 consisting of:
- $C_{1-3}$-alkyl, which is substituted with one to three F;
- cyclobutyl, which is substituted with one or two F and optionally additionally substituted with one CN;
- —O—($C_{1-3}$-alkyl), which is substituted with one to three F;
- —O—$CH_2$-cyclopropyl, which is substituted in the cyclopropyl moiety with one or two F and/or with one $CF_3$ group;
- —S—$CH_3$, which is substituted with one to three F;
- —S(=O)—$CH_3$, which is substituted with one to three F;
- —$SO_2$—$CH_3$, which is substituted with one to three F;
- —NH—($C_{1-3}$-alkyl), which is substituted with one to three F;
- —NH—$CH_2$-cyclopropyl, which is substituted in the cyclopropyl moiety with one or two F;
- —NH-cyclobutyl, which is substituted in the cyclobutyl moiety with one or two F;

—C(=O)—O—(C$_{1-3}$-alkyl), which is substituted with one to three F; heterocyclyl, which is substituted with one or two F and/or with one CF$_3$ group and which may additionally be substituted with one OH; and heteroaryl, which is substituted with one F and/or with one CF$_3$ group and which may additionally be substituted with one CH$_3$ group;

wherein each heterocyclyl group is selected from a group consisting of oxetanyl, tetrahydrofuranyl, tetrahydropyranyl, azetidinyl, pyrrolidinyl, piperidinyl, piperazinyl and morpholinyl; and wherein each heteroaryl group is selected from a group consisting of furanyl, thienyl, pyrazolyl, imidazolyl, oxazolyl, isoxazolyl, thiazolyl and isothiazolyl.

R$^3$-G3a:

In another embodiment the group R$^3$ is selected from the group R$^3$-G3a consisting of:

C$_{1-3}$-alkyl, which is substituted with one to three F;

—O—(C$_{1-3}$-alkyl), which is substituted with one to three F;

—O—CH$_2$-cyclopropyl, which is substituted in the cyclopropyl moiety with one or two F and/or with one CF$_3$ group;

—NH—(C$_{1-3}$-alkyl), which is substituted with one to three F;

—NH—CH$_2$-cyclopropyl, which is substituted in the cyclopropyl moiety with one or two F;

—NH-cyclobutyl, which is substituted in the cyclobutyl moiety with one or two F;

heterocyclyl, which is substituted with one or two F and/or with one CF$_3$ group and which may additionally be substituted with one OH; and heteroaryl, which is substituted with one F and/or with one CF$_3$ group and which may additionally be substituted with one CH$_3$ group;

wherein each heterocyclyl group is selected from a group consisting of oxetanyl, tetrahydrofuranyl, tetrahydropyranyl, azetidinyl, pyrrolidinyl, piperidinyl, piperazinyl and morpholinyl; and wherein each heteroaryl group is selected from a group consisting of furanyl, thienyl, pyrazolyl, imidazolyl, oxazolyl, isoxazolyl, thiazolyl and isothiazolyl.

R$^3$-G4:

In another embodiment the group R$^3$ is selected from the group R$^3$-G4 consisting of:

—CF$_3$, —CHF$_2$, —CH$_2$F, —O—CF$_3$, —O—CHF$_2$, —O—CH$_2$F, —O—CH$_2$—CH$_2$—F, —O—CH$_2$—CHF$_2$, —O—CH$_2$—CF$_3$, —O—CH$_2$—CH$_2$—CH$_2$—F, —O—CH$_2$—CH$_2$—CF$_3$, —S—CF$_3$,

R$^3$-G4a:

In another embodiment the group R$^3$ is selected from the group R$^3$-G4a consisting of:

—CF$_3$, —CHF$_2$, —CH$_2$F, —O—CF$_3$, —O—CHF$_2$, —O—CH$_2$F, —O—CH$_2$—CH$_2$—F, —O—CH$_2$—CHF$_2$, —O—CH$_2$—CF$_3$, —O—CH$_2$—CH$_2$—CH$_2$—F, —O—CH$_2$—CH$_2$—CF$_3$, —S—CF$_3$,

R$^3$-G4b:

In another embodiment the group R$^3$ is selected from the group R$^3$-G4b consisting of:

—CF$_3$, —CHF$_2$, —CH$_2$F, —O—CF$_3$, —O—CHF$_2$, —O—CH$_2$F, —O—CH$_2$—CH$_2$—F, —O—CH$_2$—CHF$_2$, —O—CH$_2$—CF$_3$, —O—CH$_2$—CH$_2$—CH$_2$—F, —O—CH$_2$—CH$_2$—CF$_3$,

-continued

[chemical structures]

R³-G4c:

In another embodiment the group R³ is selected from the group R³-G4c consisting of: —CF₃.

R³-G5:

In another embodiment the group R³ is selected from the group R³-G5 consisting of: —CF₃, —CHF₂, —CH₂F, —O—CF₃, —O—CHF₂ and —O—CH₂F.

R⁴

R⁴-G1:

The group R⁴ is preferably selected from the group R⁴-G1 as defined hereinbefore.

R⁴-G2:

In another embodiment the group R⁴ is independently of each other selected from the group R⁴-G2 consisting of:

F, Cl, Br, I, CN, —O—(C₃₋₇-cycloalkyl), —C(=O)—NH₂, —C(=O)—NH(C₁₋₃-alkyl), —C(=O)—N(C₁₋₃-alkyl)₂, —C(=O)—O—(C₁₋₄-alkyl), —NH₂, —N=S(=O)(C₁₋₃-alkyl)₂, heterocyclyl and heteroaryl, wherein the alkyl groups of the —N=S(=O)(C₁₋₃-alkyl)₂ group may be linked and together with the S atom, to which they are attached, form a 4-7-membered thio-heterocycle, wherein each alkyl group is optionally substituted with 1-3 F;

wherein each heterocyclyl group is selected from a group consisting of oxetanyl, tetrahydrofuranyl, tetrahydropyranyl, azetidinyl, pyrrolidinyl, piperidinyl, piperazinyl and morpholinyl;

wherein each heteroaryl group is selected from a 5-membered aromatic cycle containing 1 or 2 heteroatoms independently selected from N, O and S.

R⁴-G2a:

In another embodiment the group R⁴ is independently of each other selected from the group R⁴-G2a consisting of:

F, Cl, Br, I, CN, —C(=O)—NH₂, —C(=O)—NH(C₁₋₃-alkyl), —C(=O)—N(C₁₋₃-alkyl)₂, —C(=O)—O—(C₁₋₄-alkyl), —N=S(=O)(C₁₋₃-alkyl)₂ and heteroaryl, wherein the alkyl groups of the —N=S(=O)(C₁₋₃-alkyl)₂ group may be linked and together with the S atom, to which they are attached, form a 4-7-membered thio-heterocycle, wherein each alkyl group is optionally substituted with 1-3 F;

wherein each heteroaryl group is selected from a 5-membered aromatic cycle containing 1 or 2 heteroatoms independently selected from N, O and S.

R⁴-G2b:

In another embodiment the group R⁴ is independently of each other selected from the group R⁴-G2b consisting of:

F, Cl, Br, I, CN, C₁₋₃-alkyl, —O—(C₁₋₃-alkyl), —NH₂, heterocyclyl and heteroaryl, wherein each alkyl group is optionally substituted with 1-3 F;

wherein each heterocyclyl group is selected from a group consisting of oxetanyl, tetrahydrofuranyl, tetrahydropyranyl, azetidinyl, pyrrolidinyl, piperidinyl, piperazinyl and morpholinyl;

wherein each heteroaryl group is selected from a 5-membered aromatic cycle containing 1 or 2 heteroatoms independently selected from N, O and S.

R⁴-G3:

In another embodiment the group R⁴ is independently of each other selected from the group R⁴-G3 consisting of:

F, Cl, Br, I, CN, —O—(C₁₋₃-alkyl), —O-cyclobutyl, —C(=O)—NH₂, —C(=O)—NH(C₁₋₃-alkyl), —C(=O)—N(C₁₋₃-alkyl)₂, —C(=O)—O—(C₁₋₃-alkyl), —NH₂, —N=S(=O)(CH₃)₂, heterocyclyl and heteroaryl, wherein each alkyl group is optionally substituted with 1-3 F;

wherein each heterocyclyl group is selected from a group consisting of oxetanyl, tetrahydrofuranyl, tetrahydropyranyl, azetidinyl, pyrrolidinyl, piperidinyl, piperazinyl and morpholinyl;

wherein each heteroaryl group is selected from a group consisting of furanyl, thienyl, pyrazolyl, imidazolyl, oxazolyl, isoxazolyl, thiazolyl and isothiazolyl.

R⁴-G3a:

In another embodiment the group R⁴ is independently of each other selected from the group R⁴-G3a consisting of:

F, Cl, Br, I, CN, —C(=O)—NH₂, —C(=O)—NH(C₁₋₃-alkyl), —C(=O)—N(C₁₋₃-alkyl)₂, —C(=O)—O—(C₁₋₃-alkyl), —N=S(=O)(CH₃)₂, heterocyclyl and heteroaryl, wherein each alkyl group is optionally substituted with 1-3 F;

wherein each heterocyclyl group is selected from a group consisting of oxetanyl, tetrahydrofuranyl, tetrahydropyranyl, azetidinyl, pyrrolidinyl, piperidinyl, piperazinyl and morpholinyl;

wherein each heteroaryl group is selected from a group consisting of furanyl, thienyl, pyrazolyl, imidazolyl, oxazolyl, isoxazolyl, thiazolyl and isothiazolyl.

R⁴-G3b:
In another embodiment the group R⁴ is independently of each other selected from the group R⁴-G3b consisting of:
F, Cl, Br, I, CN, $C_{1-3}$-alkyl, —O—($C_{1-3}$-alkyl), —NH$_2$, heterocyclyl and heteroaryl,
wherein each alkyl group is optionally substituted with 1-3 F;
wherein each heterocyclyl group is selected from a group consisting of oxetanyl, tetrahydrofuranyl, tetrahydropyranyl, azetidinyl, pyrrolidinyl, piperidinyl, piperazinyl and morpholinyl;
wherein each heteroaryl group is selected from a group consisting of furanyl, thienyl, pyrazolyl, imidazolyl, oxazolyl, isoxazolyl, thiazolyl and isothiazolyl.

R⁴-G4:
In another embodiment the group R⁴ is independently of each other selected from the group R⁴-G4 consisting of:
H, F, Cl, Br, —CN, —CH$_3$, —CF$_3$, —O—CH$_3$, —O—CF$_3$, —O—CH$_2$CH$_3$, —NH$_2$,

[chemical structures]

R⁴-G4a:
In another embodiment the group R⁴ is independently of each other selected from the group R⁴-G4a consisting of:
H, F, Cl, Br, —CN, —CH$_3$, —CF$_3$, —O—CH$_3$, —O—CF$_3$, —O—CH$_2$CH$_3$,

[chemical structures]

R⁴-G4b:
In another embodiment the group R⁴ is independently of each other selected from the group R⁴-G4b consisting of:
H, F, Cl, Br, —CN, —CH$_3$, —CF$_3$, —O—CH$_3$, —O—CF$_3$, —O—CH$_2$CH$_3$, —NH$_2$,

[chemical structures]

R⁴-G4b2:
In another embodiment the group R⁴ is independently of each other selected from the group R⁴-G4b2 consisting of:
H, F, Cl, Br, —CN, —CH$_3$, —CF$_3$, —O—CH$_3$, —O—CF$_3$, —NH$_2$,

[chemical structures]

R⁴-G4c:
In another embodiment the group R⁴ is independently of each other selected from the group R⁴-G4c consisting of:
H, F, —CF$_3$, —O—CH$_3$, —O—CH$_2$CH$_3$ and

[chemical structure]

R⁴-G5:
In another embodiment the group R⁴ is independently of each other selected from the group R⁴-G5 consisting of: H, F, Br, —CN, —CH$_3$, —CF$_3$ and —O—CH$_3$.

R⁴-G5a:
In another embodiment the group R⁴ is independently of each other selected from the group R⁴-5a consisting of: H, Br, —CN and —O—CH$_3$.

n
The index n as used below is an integer selected from 0, 1 and 2.
Preferably, n is 0 or 1.
More preferably, n is 0.
Most preferably, n is 1.
In another embodiment, n is 2.
The following preferred embodiments of compounds of the formula I are described using generic formulae (I.1) to (I.16), wherein any tautomers, solvates, hydrates and salts thereof, in particular the pharmaceutically acceptable salts thereof, are encompassed. $R^1$, $R^3$, $R^4$ and n are as defined in this application.

(I.1)

[chemical structure]

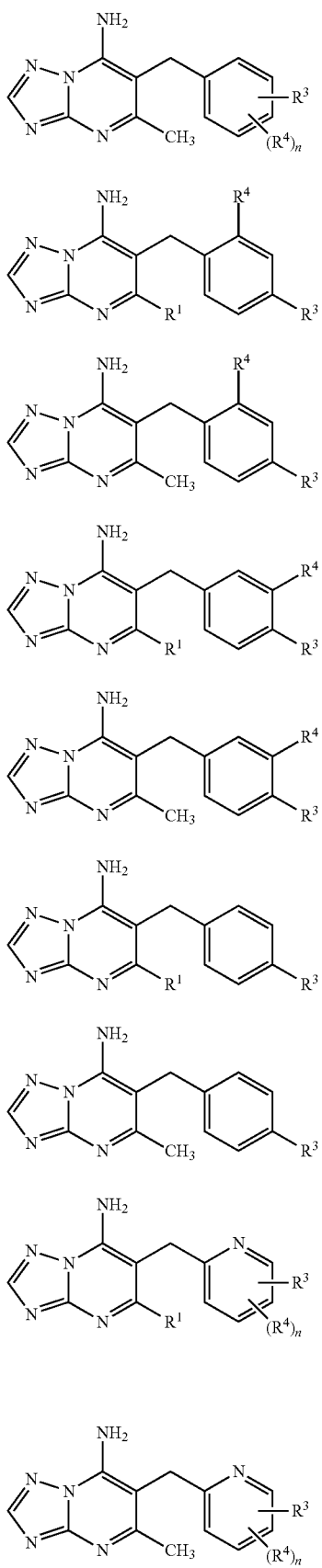
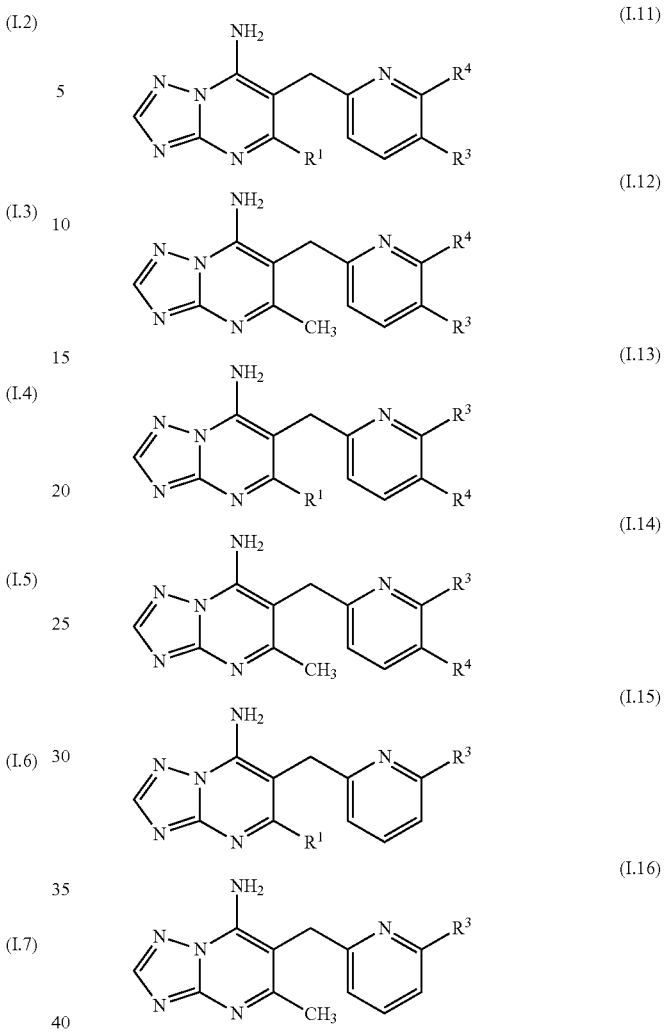

Examples of preferred subgeneric embodiments (E) according to the present invention are set forth in the following table 1, wherein each substituent group of each embodiment is defined according to the definitions set forth hereinbefore and wherein all other substituents of the formulae I and 1.1 to 1.16 are defined according to the definitions set forth hereinbefore. For example, the entry -G1 in the column under R¹— and in the line of E1 means that in embodiment E1 substituent R¹ is selected from the definition designated R¹-G1. The same applies analogously to the other variables incorporated in the general formulae.

TABLE 1

| E | formula | R¹— | R²— | R³— | R⁴— | number n of substituents R⁴ |
|---|---|---|---|---|---|---|
| E1 | I | —G1 | —G1 | —G1 | —G1 | 0, 1 or 2 |
| E2 | I | —G1 | —G1 | —G1 | —G1 | 0 or 1 |
| E3 | I | —G2 | —G2 | —G2 | —G2 | 0 or 1 |
| E4 | I | —G3 | —G2 | —G2 | —G2 | 0 or 1 |
| E5 | I | —G6 | —G2 | —G2 | —G2 | 0 or 1 |
| E6 | I | —G3 | —G2 | —G3 | —G3 | 0 or 1 |
| E7 | I | —G3 | —G2 | —G4 | —G4 | 0 or 1 |
| E8 | I | —G3 | —G2 | —G4 | —G5 | 0 or 1 |
| E9 | I | —G3 | —G2 | —G4 | —G5a | 0 or 1 |
| E10 | I | —G3 | —G2 | —G4c | —G3 | 0 or 1 |

TABLE 1-continued

| E | formula | R$^1$— | R$^2$— | R$^3$— | R$^4$— | number n of substituents R$^4$ |
|---|---|---|---|---|---|---|
| E11 | I | —G3 | —G2 | —G4c | —G4 | 0 or 1 |
| E12 | I | —G3 | —G2 | —G5 | —G3 | 0 or 1 |
| E13 | I | —G3 | —G2 | —G5 | —G4 | 0 or 1 |
| E14 | I | —G3 | —G2 | —G5 | —G5 | 0 or 1 |
| E15 | I | —G3 | —G3 | —G3 | —G3 | 0 or 1 |
| E16 | I | —G3 | —G3 | —G4 | —G4 | 0 or 1 |
| E17 | I | —G3 | —G3 | —G4 | —G5 | 0 or 1 |
| E18 | I | —G3 | —G3 | —G4 | —G5a | 0 or 1 |
| E19 | I | —G3 | —G3 | —G4c | —G3 | 0 or 1 |
| E20 | I | —G3 | —G3 | —G4c | —G4 | 0 or 1 |
| E21 | I | —G3 | —G3 | —G5 | —G3 | 0 or 1 |
| E22 | I | —G3 | —G3 | —G5 | —G4 | 0 or 1 |
| E23 | I | —G3 | —G3 | —G5 | —G5 | 0 or 1 |
| E24 | I | —G3 | —G3a | —G3 | —G3 | 0 or 1 |
| E25 | I | —G3 | —G3a | —G4 | —G4 | 0 or 1 |
| E26 | I | —G3 | —G3a | —G4 | —G5 | 0 or 1 |
| E27 | I | —G5 | —G4 | —G3 | —G2a | 0 or 1 |
| E28 | I | —G5 | —G4 | —G3a | —G3 | 0 or 1 |
| E29 | I | —G5 | —G4 | —G4a | —G4a | 0 or 1 |
| E30 | I | —G5 | —G4a | —G3 | —G2a | 0 or 1 |
| E31 | I | —G5 | —G4a | —G3a | —G4a | 0 or 1 |
| E32 | I | —G5 | —G4a | —G4a | —G4a | 0 or 1 |
| E33 | I | —G5 | —G5 | —G3a | —G4b | 0 or 1 |
| E34 | I | —G5 | —G5 | —G4b | —G4b | 0 or 1 |
| E35 | I | —G5 | —G5 | —G5 | —G4b | 0 or 1 |

Another embodiment concerns compounds of formula (I.1)

wherein
R$^1$ is CH$_3$ or Cl;
n is 0 or 1;
R$^3$ is —CF$_3$, —CHF$_2$, —CH$_2$F, —O—CF$_3$, —O—CHF$_2$, —O—CH$_2$F, —O—CH$_2$—CH$_2$—F, —O—CH$_2$—CHF$_2$, —O—CH$_2$—CF$_3$, —O—CH$_2$—CH$_2$—CH$_2$—F, —O—CH$_2$—CH$_2$—CF$_3$, —S—CF$_3$, and
R$^4$ is F, Cl, Br, I, CN, —C(=O)—NH$_2$, —C(=O)—NH(C$_{1-3}$-alkyl), —C(=O)—N(C$_{1-3}$-alkyl)$_2$, —C(=O)—O—(C$_{1-3}$-alkyl), —N=S(=O)(CH$_3$)$_2$, heterocyclyl or heteroaryl,
  wherein each alkyl group is optionally substituted with 1-3 F;
  wherein each heterocyclyl group is selected from a group consisting of oxetanyl, tetrahydrofuranyl, tetrahydropyranyl, azetidinyl, pyrrolidinyl, piperidinyl, piperazinyl and morpholinyl;
  wherein each heteroaryl group is selected from a group consisting of furanyl, thienyl, pyrazolyl, imidazolyl, oxazolyl, isoxazolyl, thiazolyl and isothiazolyl;
or a salt thereof, particularly a pharmaceutically acceptable salt thereof.

Still another embodiment concerns compounds of formula (I.10)

wherein
n is 0 or 1;
R$^3$ is:
  C$_{1-3}$-alkyl, which is substituted with one to three F;
  —O—(C$_{1-3}$-alkyl), which is substituted with one to three F;
  —O—CH$_2$-cyclopropyl, which is substituted in the cyclopropyl moiety with one or two F and/or with one CF$_3$ group;
  —NH—(C$_{1-3}$-alkyl), which is substituted with one to three F;
  —NH—CH$_2$-cyclopropyl, which is substituted in the cyclopropyl moiety with one or two F;
  —NH-cyclobutyl, which is substituted in the cyclobutyl moiety with one or two F; heterocyclyl, which is substituted with one or two F and/or with one CF$_3$ group and which may additionally be substituted with one OH; or
  heteroaryl, which is substituted with one F and/or with one CF$_3$ group and which may additionally be substituted with one CH$_3$ group;
    wherein each heterocyclyl group is selected from a group consisting of oxetanyl, tetrahydrofuranyl, tetrahydropyranyl, azetidinyl, pyrrolidinyl, piperidinyl, piperazinyl and morpholinyl; and
    wherein each heteroaryl group is selected from a group consisting of furanyl, thienyl, pyrazolyl, imidazolyl, oxazolyl, isoxazolyl, thiazolyl and isothiazolyl; and
R$^4$ is F, Cl, Br, I, CN, —O—(C$_{1-3}$-alkyl), —NH$_2$, heterocyclyl or heteroaryl,
  wherein each alkyl group is optionally substituted with 1-3 F;
  wherein each heterocyclyl group is selected from a group consisting of oxetanyl, tetrahydrofuranyl, tetrahydropyranyl, azetidinyl, pyrrolidinyl, piperidinyl, piperazinyl and morpholinyl;
  wherein each heteroaryl group is selected from a group consisting of furanyl, thienyl, pyrazolyl, imidazolyl, oxazolyl, isoxazolyl, thiazolyl and isothiazolyl;
or a salt thereof, particularly a pharmaceutically acceptable salt thereof.

Preferred compounds of the invention include:

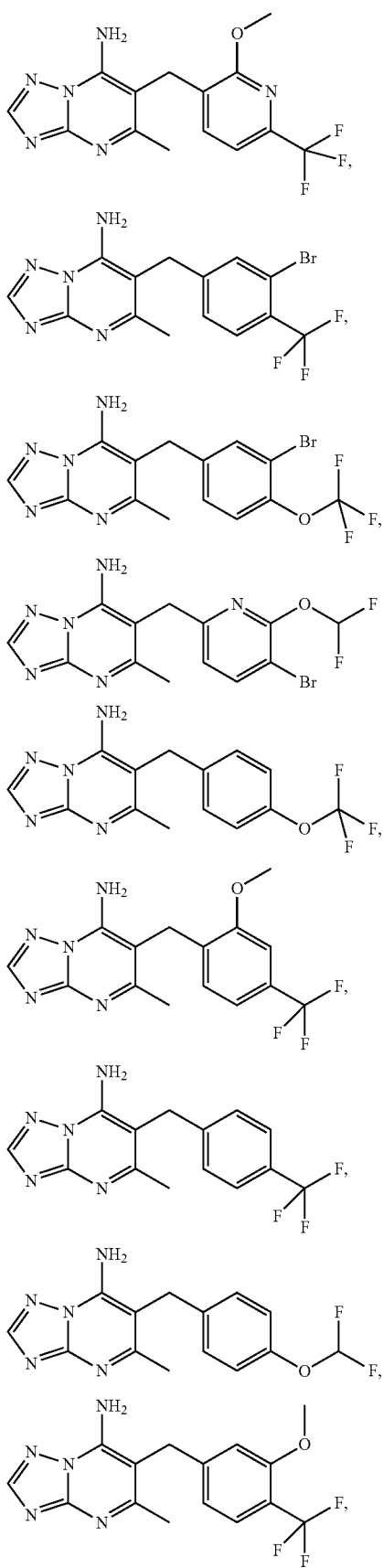
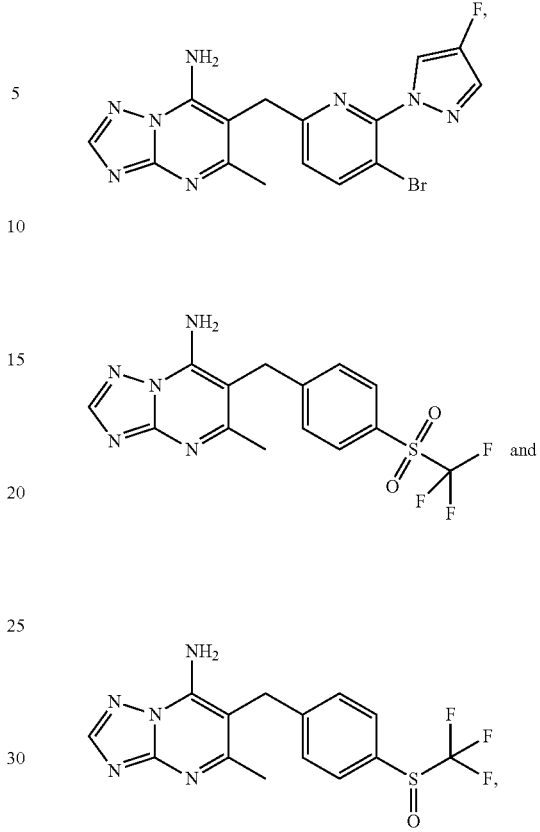

or a salt thereof, particularly a pharmaceutically acceptable salt thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis for example.

Moreover, the invention provides processes for making a compound of Formula I.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula I may be made by the method outlined in Scheme 1, 2, or 3:

Scheme 1

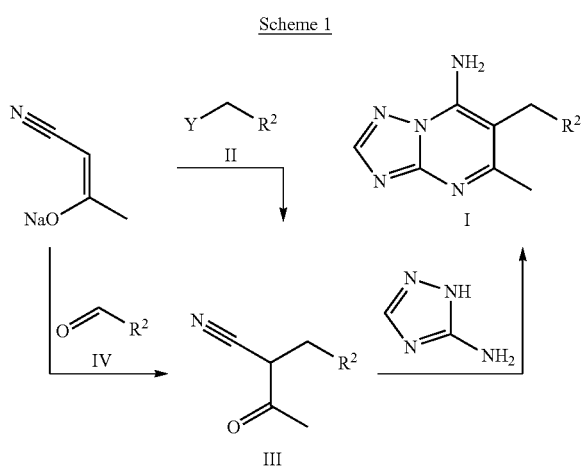

As illustrated in Scheme 1 reacting of the cyanoacetone sodium salt (sodium (E) cyanoprop-1-en-2-olate) with an alkylating agent of formula II (Y=Cl, Br, I, OMs, OTs) in a suitable solvent such as N,N-dimethylformamide, provides a compound of formula III. Alternatively, compound of formula III can be obtained via direct proline catalysed cascade reductive alkylation of cyanoacetone sodium salt: reacting of the cyanoacetone sodium salt (sodium (E)-1-cyanoprop-1-en-2-olate) with an aldehyde of Formula IV in the presence of a suitable amino acid such as proline and suitable organic hydrogen source such as diethyl 1,4-dihydro-2,6-dimethyl-3,5-pyridinedi-carboxylate in a suitable solvent such as ethanol, provides compound of formula III.

Reacting of the compound of Formula III with the 1H-1,2,4-triazol-3-amine in a suitable solvent such as n-propionic or 2,2-dimethylpropionic acid, provides a compound of Formula I.

Scheme 2

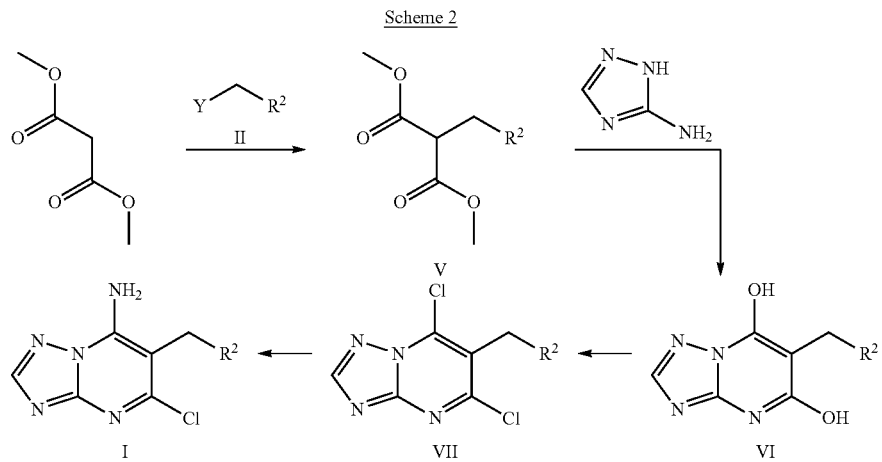

As illustrated in Scheme 2 reacting of the dimethyl malonate with an alkylating agent of formula II (Y=Cl, Br, I, OMs, OTs) in the presence of a suitable base such as sodium hydride, in a suitable solvent such as N,N-dimethylformamide, provides compound of formula V.

Reacting of the malonate derivative V with 1H-1,2,4-triazol-3-amine, in the presence of a suitable base such as tri-n-butylamine provides compound of formula VI.

Dihydroxy derivative VI can be converted into the corresponding dichloride VII using suitable reagents, such as phosphorus oxychloride.

Reacting of the compound of formula VII with ammonia in a suitable solvent such as 1,4-dioxane or methanol, provides compound of formula I.

Scheme 3

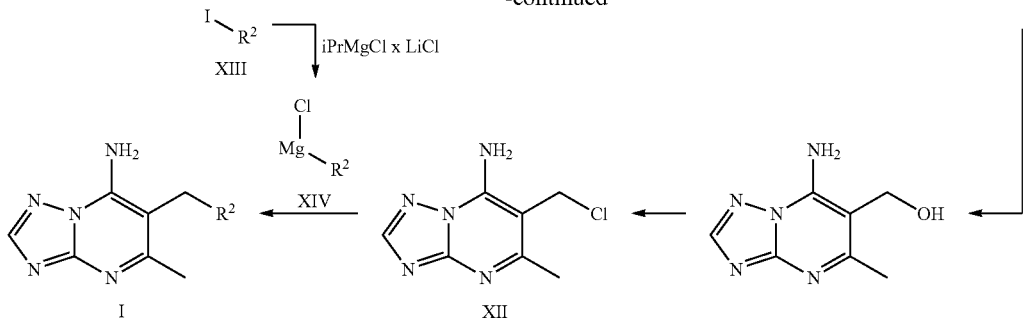

As illustrated in Scheme 3 reacting of the cyanoacetone sodium salt (sodium (E)-1-cyanoprop-1-en-2-olate) with the 1H-1,2,4-triazol-3-amine in a suitable solvent such as glacial acetic acid, provides a compound of formula VIII. Reacting of compound of formula VIII with the suitable reagent such as chloramine-T (N-chloro tosylamide, sodium salt) in the presence of a sodium iodide, in a suitable solvent such as glacial acetic acid, provides a compound of formula IX. Compound IX can be reacted with carbon monoxide in the presence of methanol, a suitable catalyst such as [1,1'-bis(diphenylphosphino)ferrocene]dichloropalladium(II), and a suitable base such triethylamine, in a suitable solvent such as N,N-dimethylformamide to yield the ester X.

Reduction of the ester X with the reducing agent such as sodium bis(2-methoxyethoxy)aluminiumhydride (Red-Al®) or lithium aluminium hydride, in a suitable solvent such as toluene/tetrahydrofuran mixture, provides alcohol XI. Alcohol XI can be converted into the corresponding chloride XII using suitable reagent such as oxalyl chloride in a suitable solvent such as 1-methyl-2-pyrrolidinone or tetrahydrofuran.

Iodide of formula XIII can be converted into the corresponding magnesium reagent of formula XIV using suitable reagent such as isopropylmagnesium chloride lithium chloride complex, in a suitable solvent such as tetrahydrofuran. Reacting of the magnesium reagent of formula XIV with the compound of formula XII in the presence of copper(I) cyanide di(lithium chloride) complex, in a suitable solvent such as tetrahydrofuran, provides a compound of formula I.

Further modifications of compounds of formula I by methods known in the art and illustrated in the Examples below, may be used to prepare additional compounds of the invention.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis for example in "Protecting Groups, 3$^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the inhibition of the ghrelin O-acyl transferase (GOAT) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

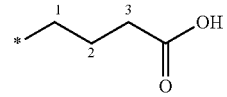

wherein the carboxy group is attached to the third carbon atom of the propyl group. The terms "1-methylpropyl-", "2,2-dimethylpropyl-" or "cyclopropylmethyl-" group represent the following groups:

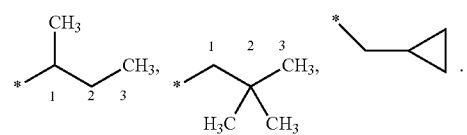

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $-(CH_2)-$, $-(CH_2-CH_2)-$, $-(CH(CH_3))-$, $-(CH_2-CH_2-CH_2)-$, $-(C(CH_3)_2)-$, $-(CH(CH_2CH_3))-$, $-(CH(CH_3)-CH_2)-$, $-(CH_2-CH(CH_3))-$, $-(CH_2-CH_2-CH_2-CH_2)-$, $-(CH_2-CH_2-CH(CH_3))-$, $-(CH(CH_3)-CH_2-CH_2)-$, $-(CH_2-CH(CH_3)-CH_2)-$, $-(CH_2-C(CH_3)_2)-$, $-(C(CH_3)_2-CH_2)-$, $-(CH(CH_3)-CH(CH_3))-$, $-(CH_2-CH(CH_2CH_3))-$, $-(CH(CH_2CH_3)-CH_2)-$, $-(CH(CH_2CH_2CH_3))-$, $-(CHCH(CH_3)_2)-$ and $-C(CH_3)(CH_2CH_3)-$.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes $-CH=CH_2$, $-CH=CH-CH_3$, $-CH_2-CH=CH_2$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes $-C\equiv CH$, $-C\equiv C-CH_3$, $-CH_2-C\equiv CH$.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclononyl, cyclododecyl, bicyclo[3.2.1.]octyl, spiro[4.5]decyl, norpinyl, norbornyl, norcaryl, adamantyl, etc.

Many of the terms given above may be used repeatedly in the definition of a formula or group and in each case have one of the meanings given above, independently of one another.

Pharmacological Activity

Determination of hGOAT Activity in HEK293 Cells after incubation with test compound Principle:

HEK293 cells stably transfected with two expression vectors, one coding for preproghrelin cDNA and a second for the expression of human GOATcDNA are used as a cellular model. After feeding the cells with octanoic acid for 5 hours, acyl-ghrelin is measured in cell culture medium by an ELISA procedure.

Materials:

Cellline: Hek293 hGOAT/PPGhrl Clone #1B8Sodium octanoate, Sigma, Cat.-No. C5038

BSA: Sigma, Cat.-No. A8806

BD Poly-D-Lysin 384-well Plates, black-clear polystyrene BD Bioscience Cat.-No. 356697348-well ELISA human acylated Ghrelin Kit purchased from Bertin Pharman (detailed composition of buffers e.g. wash-puffer, ELISA buffer not known)

All further reagents used were of highest analytical grade available.

Method:

Cells are plated with a density of 5000 cells/well in 384-well poly-D-lysin plates and incubated for 1 day at 37° C., 5% CO2 in DMEM medium, 10% FCS, 1×NEAA, Puromycin (0.5 µg/ml) and G418 (1 mg/ml). Then the medium is changed to a identical medium without FCS and containing Octanoate-BSA (final concentration 100 µM each) and compound in DMSO (final DMSO concentration 0.3%). After incubation for 5 hours acylghrelin in the medium is measured by ELISA.

The medium sample is diluted 1:25 in Elisa buffer, a 25 µl aliquot is transferred to a 384-well ELISA plate previously washed 4 times with 100 µL wash buffer, and 25 µl tracer-solution is added. After incubation overnight (~20 h) at 4° C. temperature the plate is washed 4 times with 100 µl wash-buffer per well. Finally 50 µl Ellman's reagent is added to each well and the plate is incubated in the dark for 20 minutes. The absorbance is measured at 405 nm in an Envision multilabel reader and the amount of acylated ghrelin is calculated according to a acylated ghrelin standard curve provided in the same plate.

Each assay plate contains wells with vehicle controls (1% DMSO) for the measurement of non-inhibited transfer reaction (=100% Ctl) and wells with 10 µM ([Dap3]-Ghrelin) as controls for fully inhibited GOAT enzyme The analysis of the data is performed by calculation of the percentage of acyl-ghrelin produced in the presence of test compound compared to the amount of acyl-ghrelin produced in the vehicle control samples. An inhibitor of the GOAT enzyme will give values between 100% CTL (no inhibition) and 0% CTL (complete inhibition).

IC50 values are calculated with Assay Explorer or other suited software based on curve fitting of results of 8 different compound concentrations.

Results:

| example | IC50 [nM] |
|---------|-----------|
| 1.1 | 0.31 |
| 1.2 | 2 |
| 2.1 | 0.40 |
| 2.2 | 0.59 |
| 3.1 | 0.65 |
| 3.3 | 0.32 |
| 3.3 | 0.76 |
| 3.4 | 6.5 |

| example | IC50 [nM] |
|---|---|
| 4.1 | 0.30 |
| 4.2 | 1.9 |
| 4.3 | 1.1 |
| 4.4 | 1.1 |
| 4.5 | 2.4 |
| 4.6 | 3 |
| 4.7 | 2.9 |
| 4.8 | 8.8 |
| 4.9 | 9.8 |
| 5.1 | 0.13 |
| 6.1 | 3.9 |
| 6.2 | 0.69 |
| 6.3 | 3.4 |
| 6.4 | 1.9 |
| 6.5 | 1.7 |
| 7.1 | 0.37 |
| 7.2 | 0.57 |
| 7.3 | 2.3 |
| 7.4 | 1.3 |
| 7.5 | 0.92 |
| 7.6 | 0.69 |
| 7.7 | 0.93 |
| 7.8 | 1.1 |
| 7.9 | 1.3 |
| 7.10 | 6.2 |
| 7.11 | 5.2 |
| 8.1 | 0.27 |
| 8.2 | 0.23 |
| 8.3 | 0.30 |
| 8.4 | 0.30 |
| 9.1 | 2.4 |
| 9.2 | 8.3 |
| 9.3 | 0.56 |
| 9.4 | 3.7 |
| 9.5 | 3.9 |
| 10.1 | 0.68 |
| 10.2 | 2.8 |
| 10.3 | 8.6 |
| 11.1 | 0.95 |
| 11.2 | 0.68 |
| 12.1 | 4.4 |
| 13.1 | 1.7 |
| 13.2 | 2.1 |
| 14.1 | 0.31 |
| 15.1 | 0.83 |
| 15.2 | 3.5 |
| 15.2 | 5.4 |
| 15.3 | 8.6 |
| 15.4 | 9.3 |
| 16.1 | 3.1 |
| 17.1 | 0.95 |
| 17.2 | 5 |
| 18.1 | 4.2 |
| 19.1 | 4.9 |
| 20.1 | 9.2 |
| 21.1 | 8.1 |
| 22.1 | 7.2 |
| 23.1 | 0.25 |
| 23.2 | 0.29 |
| 23.3 | 0.36 |
| 23.4 | 0.70 |
| 23.5 | 0.83 |
| 23.6 | 0.86 |
| 23.7 | 7.7 |
| 24.1 | 4.6 |
| 25.1 | 0.83 |
| 25.2 | 1 |
| 25.3 | 5.7 |

In view of their ability to modulate the activity of ghrelin O-acyl transferase (GOAT), in particular an inhibitory activity, the compounds of general formula I according to the invention, including the corresponding salts thereof, are suitable for the treatment of all those diseases or conditions which may be affected or which are mediated by the inhibition of ghrelin O-acyl transferase (GOAT).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the inhibition of ghrelin O-acyl transferase (GOAT) in a patient, preferably in a human.

In yet another aspect the present invention relates to a method for treating a disease or condition mediated by the inhibition of ghrelin O-acyl transferase (GOAT) in a mammal that includes the step of administering to a patient, preferably a human, in need of such treatment a therapeutically effective amount of a compound or a pharmaceutical composition of the present invention.

Diseases and conditions mediated by inhibitors of ghrelin O-acyl transferase (GOAT) embrace obesity, including, but not limited to obesity in patients suffering from Prader-Willi-Syndrome (PWS), body weight regain, diabetes, particularly type 2 diabetes mellitus, insulin resistance, hyperphagia in PWS, Binge eating disorder, nighttime eating syndrome and alcohol and/or narcotic dependence.

Preferably, the compounds of the invention are used for treating obesity, body weight regain, type 2 diabetes, insulin resistance, and hyperphagia and obesity in PWS.

More preferably, the compounds of the invention are used for treating obesity, body weight regain, type 2 diabetes and insulin resistance.

In particular, the compounds and pharmaceutical compositions according to the invention are suitable for the treatment of obesity, including, but not limited to obesity in patients suffering from Prader-Willi-Syndrome, body weight regain, diabetes, in particular type 2 diabetes mellitus, and insulin resistance.

The compounds according to the invention are most particularly suitable for treating obesity.

The present invention further provides a GOAT inhibitor of the invention for use in a method of medical treatment.

GOAT inhibitors are useful, inter alia, in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or disorders, such as diabetes (e.g. type 2 diabetes). It will be understood that the GOAT inhibitors may thus be administered to subjects affected by conditions characterised by inadequate control of appetite or otherwise over-feeding, such as binge-eating disorder and Prader-Willi syndrome.

Thus, the invention provides a GOAT inhibitor of the invention for use in a method of treating, inhibiting or reducing weight gain, promoting weight loss and/or reducing excess body weight. Treatment may be achieved, for example, by control of appetite, feeding, food intake, calorie intake and/or energy expenditure.

The invention also provides a GOAT inhibitor of the invention for use in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides a GOAT inhibitor of the invention for use in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides a GOAT inhibitor of the invention for use in a method of lowering circulating LDL levels and/or increasing HDL/LDL ratio.

Effects of GOAT inhibitors on these conditions may be mediated in whole or in part via an effect on body weight, or may be independent thereof.

The invention further provides use of a GOAT inhibitor of the invention in the manufacture of a medicament for treating, inhibiting or reducing weight gain, promoting weight loss and/or reducing excess body weight.

The invention also provides use of a GOAT inhibitor of the invention in the manufacture of a medicament for treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides use of a GOAT inhibitor of the invention in the manufacture of a medicament for the prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides use of a GOAT inhibitor of the invention in the manufacture of a medicament for lowering circulating LDL levels and/or increasing HDL/LDL ratio.

The invention further provides a method of treating, inhibiting or reducing weight gain, promoting weight loss and/or reducing excess body weight in a subject, comprising administering a therapeutically effective amount of a GOAT inhibitor of the invention to the subject.

The invention also provides a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility in a subject, comprising administering a therapeutically effective amount of a GOAT inhibitor of the invention to the subject.

The invention also provides a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke in a subject, comprising administering a therapeutically effective amount of a GOAT inhibitor of the invention to the subject.

The invention further provides a method of lowering circulating LDL levels and/or increasing HDL/LDL ratio in a subject, comprising administering a therapeutically effective amount of a GOAT inhibitor of the invention to the subject.

The invention further provides the use of a GOAT inhibitor as described above in a method of cosmetic (i.e. non-therapeutic) weight loss. It will be understood that references to therapeutic uses of GOAT inhibitors and methods comprising administration of GOAT inhibitors may equally be taken to encompass uses and administration of such compositions.

Further aspects and embodiments of the present invention will become apparent from the disclosure below.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

A compound of the invention may be administered as part of a combination therapy together with another active agent for the treatment of the disease or disorder in question, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus a compound of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), an SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, lixisenatide (Lyxumia™) and liraglutide (Victoza™)

Moreover, a compound of the invention may be used in combination with an anti-obesity agent of known type, including, but not limited to, peptide YY or an analogue thereof, neuropeptide Y (NPY) or an analogue thereof, a cannabinoid receptor 1 antagonist, a lipase inhibitor, Human proIslet Peptide (HIP), a melanocortin receptor 4 agonist, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), Orlistat™, Sibutramine™, phentermine, a melanin concentrating hormone receptor 1 antagonist, CCK, amylin, pramlintide and leptin, as well as analogues thereof.

A compound of the invention may further be used in combination with an anti-hypertension agent of a known type, including, but not limited to, an angiotensin-converting enzyme inhibitor, an angiotensin II receptor blocker, a diuretic, a beta-blocker and a calcium channel blocker.

A compound of the invention may still further be used in combination with an anti-dyslipidemia agent of known type, including, but not limited to, a statin, a fibrate, a niacin, a PSCK9 (Proprotein convertase subtilisin/kexin type 9) inhibitor, and a cholesterol absorption inhibitor.

A compound of the invention may also be used in combination with a proton pump inhibitor (i.e. a pharmaceutical agent possessing pharmacological activity as an inhibitor of W/K$^+$-ATPase) of known type, including, but not limited to, an agent of the benzimidazole derivative type or of the imidazopyridine derivative type, such as Omeprazole™, Lansoprazole™, Dexlansoprazole™, Esomeprazole™, Pantoprazole™, Rabeprazole™, Zolpidem™, Alpidem™, Saripidem™ or Necopidem™.

In addition, with regard to anti-inflammatory treatment, a compound of the invention may be beneficial if administered in combination with an anti-inflammatory agent of known type, including, but not limited to:

steroids and corticosteroids, such as beclomethasone, methylprednisolone, betamethasone, prednisone, dexamethasone, and hydrocortisone;

non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);

COX II inhibitors, such as rofecoxib and celecoxib; preparations of interferon beta (e.g. interferon beta-1a or interferon beta-1b);

and certain other compounds, such as 5-aminosalicylic acid and prodrugs and pharmaceutically acceptable salts thereof.

Metformin has also been demonstrated to have anti-inflammatory properties (see, e.g., Haffner et al., *Diabetes* 54: 1566-1572 (2005)) and as such may also be useful in combination with compounds of the invention.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the inhibition of ghrelin O-acyl transferase (GOAT), in particular diseases or conditions as described hereinbefore and hereinafter.

In yet another aspect the present invention relates a method for treating a disease or condition mediated by the inhibition of ghrelin O-acyl transferase (GOAT) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The following examples serve to further explain the invention without restricting it.

The hereinafter described compounds have been characterized through their characteristic mass after ionisation in a mass-spectrometer and/or their retention time on an analytical HPLC.

HPLC Methods:

Method 1: Column: Waters XBridge C18, 3×30 mm, 2.5 µm

Detection: Agilent 1200 with DA- and MS-Detector

Eluent A: Water (0.1% $NH_4OH$); Eluent B: Acetonitrile

| Gradient: | | | |
| --- | --- | --- | --- |
| Time (min.) | % Eluent B | Flow [mL/min] | Temp [° C.] |
| 0.00 | 3 | 2.2 | 60 |
| 0.20 | 3 | 2.2 | 60 |
| 1.20 | 100 | 2.2 | 60 |
| 1.25 | 100 | 3.0 | 60 |
| 1.40 | 100 | 3.0 | 60 |

Method 2: Column: Waters SunFire, 3×30 mm, 2.5 µm

Detection: Agilent 1200 with DA- and MS-Detector

Eluent A: Water (0.1% Trifluoroacetic acid); Eluent B: Acetonitrile

| Gradient: | | | |
| --- | --- | --- | --- |
| Time (min.) | % Eluent B | Flow [mL/min] | Temp [° C.] |
| 0.00 | 3 | 2.2 | 60 |
| 0.20 | 3 | 2.2 | 60 |
| 1.20 | 100 | 2.2 | 60 |
| 1.25 | 100 | 3.0 | 60 |
| 1.40 | 100 | 3.0 | 60 |

Method 3: Column: Waters SunFire C18, 3×30 mm, 2.5 µm

Detection: Agilent 1200 with DA- and MS-Detector

Eluent A: Water (0.1% Formic acid); Eluent B: Acetonitrile

| Gradient: | | | |
| --- | --- | --- | --- |
| Time (min.) | % Eluent B | Flow [mL/min] | Temp [° C.] |
| 0.00 | 3 | 2.2 | 60 |
| 0.20 | 3 | 2.2 | 60 |
| 1.20 | 100 | 2.2 | 60 |
| 1.25 | 100 | 3.0 | 60 |
| 1.40 | 100 | 3.0 | 60 |

Method 4: Column: Waters XBridge C18, 3×30 mm, 2.5 µm

Detection: Agilent 1200 with DA- and MS-Detector

Eluent A: Water (0.1% Formic acid); Eluent B: Acetonitrile

| Gradient: | | | |
| --- | --- | --- | --- |
| Time (min.) | % Eluent B | Flow [mL/min] | Temp [° C.] |
| 0.00 | 3 | 2.2 | 60 |
| 0.20 | 3 | 2.2 | 60 |
| 1.20 | 100 | 2.2 | 60 |
| 1.25 | 100 | 3.0 | 60 |
| 1.40 | 100 | 3.0 | 60 |

Method 5: Column: Waters SunFire C18, 3.0×30 mm, 2.5 µm

Detection: Agilent 1100 with DAD; Waters Autosampler and MS-Detector

Eluent A: Water (0.1% Trifluoroacetic acid); Eluent B: Acetonitrile

| Gradient: | | | |
| --- | --- | --- | --- |
| Time (min.) | % Eluent B | Flow [mL/min] | Temp [° C.] |
| 0.00 | 2 | 2.0 | 60 |
| 1.20 | 100 | 2.0 | 60 |
| 1.40 | 100 | 2.0 | 60 |

Method 6: Column: Waters XBridge C18, 3.0×30 mm, 2.5 µm

Detection: Waters Acquity with 3100 MS

Eluent A: Water (0.1% $NH_4OH$); Eluent B: Acetonitrile

| Gradient: | | | |
| --- | --- | --- | --- |
| Time (min.) | % Eluent B | Flow [mL/min] | Temp [° C.] |
| 0.00 | 5 | 1.5 | 60 |
| 1.30 | 99.0 | 1.5 | 60 |
| 1.50 | 99.0 | 1.5 | 60 |

Method 7: XBridge C18_3.0×30 mm, 2.5 µm

Detection: Agilent 1200 with DA- and MS-Detector

Eluent A: Water (0.1% Trifluoroacetic acid); Eluent B: Acetonitrile

| Gradient: | | | |
|---|---|---|---|
| Time (min.) | % Eluent B | Flow [mL/min] | Temp [° C.] |
| 0.00 | 3 | 2.2 | 60 |
| 0.20 | 3 | 2.2 | 60 |
| 1.20 | 0 | 2.2 | 60 |
| 1.25 | 0 | 2.2 | 60 |
| 1.40 | 0 | 2.2 | 60 |

Method 8: Sunfire C18_3.0×30 mm, 3.5 µm

Detection: Agilent 1100 with DAD, CTC Autosampler and Waters MS-Detector

Eluent A: Water (0.1% Trifluoroacetic acid); Eluent B: Acetonitrile

| Gradient: | | | |
|---|---|---|---|
| Time (min.) | % Eluent B | Flow [mL/min] | Temp [° C.] |
| 0.00 | 2 | 2.0 | 60 |
| 0.30 | 2 | 2.0 | 60 |
| 1.50 | 100 | 2.0 | 60 |
| 1.60 | 100 | 2.0 | 60 |

Intermediate 4.1.A

[6-Bromo-5-(difluoromethoxy)pyridin-2-yl]methanol

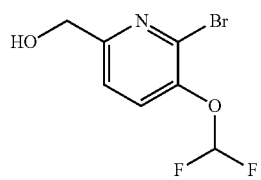 [SMILES: OCc1ccc(OC(F)F)c(Br)n1]

To a solution of 2-bromo-6-(hydroxymethyl)pyridin-3-ol (1.60 g; 7.84 mmol), 20 mL N,N-dimethylformamide and 2 mL water is added potassium carbonate (2.71 g; 19.61 mmol).

The solution is stirred for a few minutes, sodium 2-chloro-2,2-difluoroacetate (2.99 g; 19.61 mmol) is added and the solution is stirred overnight at 100° C. The reaction is diluted with ethyl acetate and extracted with NaHCO$_3$ (half saturated aqueous solution) and brine, dried and concentrated under reduced pressure.

Yield: 2.2 g (100% of theory)

Mass spectrometry (ESI$^+$): m/z=254, 256 [M+H]$^+$ (Br)

HPLC (Method 4): Retention time=0.750 min.

Intermediate 4.2.B

Step A

2-Methoxy-6-(trifluoromethyl)pyridine-3-carboxylic acid

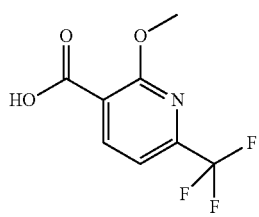

2-Chloro-6-(trifluoromethyl)pyridine-3-carboxylic acid (750 mg; 2.99 mmol) dissolved in 4 mL sodium methanolate (30% in methanol) and the reaction mixture is stirred for 2 hours at 80° C. The reaction is acidified with HCl (4M aqueous solution) and extracted two times with dichloromethane. The combined organic layers are dried and concentrated under reduced pressure.

Yield: 727 mg (99% of theory)

Mass spectrometry (ESI$^+$): m/z=222 [M+H]$^+$

HPLC (Method 4): Retention time=0.875 min.

Step B

[2-Methoxy-6-(trifluoromethyl)pyridin-3-yl]methanol

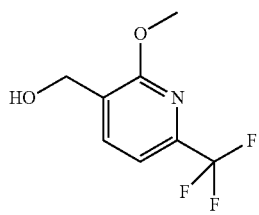

To 2-methoxy-6-(trifluoromethyl)pyridine-3-carboxylic acid (727 mg; 2.96 mmol) dissolved in 10 mL tetrahydrofuran is added lithium aluminium hydride (2M in tetrahydrofuran) (2.22 mL; 4.44 mmol) and the reaction mixture is stirred for 3 hours at room temperature. The reaction mixture is quenched with HCl (4M aqueous solution) and extracted two times with dichloromethane. The combined organic layers are dried and concentrated under reduced pressure.

Yield: 603 mg (98% of theory)

Mass spectrometry (ESI$^+$): m/z=208 [M+H]$^+$

HPLC (Method 7): Retention time=0.927 min.

Prepared analogously to intermediate 4.2.B starting with the corresponding carboxylic acid

| Intermediate | Structure | HPLC Retention time | Starting material for step B Carboxylic acid |
|---|---|---|---|
| 4.9.B | 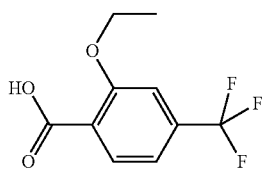 [SMILES: CCOc1cc(C(F)(F)F)ccc1C(=O)O] | (Method 3): 0.774 min | 4-(difluoro-methyl)benzoic acid |

Intermediate 4.5.B

Step A

2-Ethoxy-4-(trifluoromethyl)benzoic acid

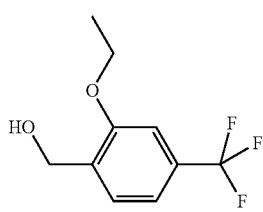

To a mixture of ethanol (2.05 g; 44.5 mmol) and 30 mL N-methyl pyrrolidine is added sodium hydride (55% in mineral oil) (534 mg; 22.3 mmol) and the reaction mixture is stirred for 30 min at room temperature. 2-chloro-4-(trifluoromethyl)benzoic acid (1.00 g; 4.45 mmol) is added and the reaction mixture is stirred at 120° C. overnight. The reaction is acidified with HCl (1M aqueous solution) and extracted three times with ethyl acetate. The combined organic layers are dried and concentrated under reduced pressure.

Yield: 1 g (96% of theory)
Mass spectrometry (ESI⁺): m/z=233 [M−H]⁻
HPLC (Method 3): Retention time=0.980 min.

Step B

[2-Ethoxy-4-(trifluoromethyl)phenyl]methanol

To 2-ethoxy-4-(trifluoromethyl)benzoic acid (1.00 g; 4.27 mmol) dissolved in 20 mL tetrahydrofuran is added 1-(1H-imidazole-1-carbonyl)-1H-imidazole (767 mg; 4.70 mmol) and the reaction mixture is stirred at room temperature overnight. The reaction mixture is cooled to 0° C. and sodium borohydride (404 mg; 10.67 mmol) dissolved in 5 mL water is added dropwise. The reaction mixture is stirred overnight at room temperature. The reaction mixture is diluted with water, acidified with HCl (half saturated aqueous solution) and extracted two times with dichloromethane. The combined organic layers are dried and concentrated under reduced pressure.

Yield: 990 mg (95% of theory)
HPLC (Method 3): Retention time=1.008 min.

Intermediate 4.6.B

Step A

2-Cyclobutoxy-6-(trifluoromethyl)pyridine-3-carboxylic acid

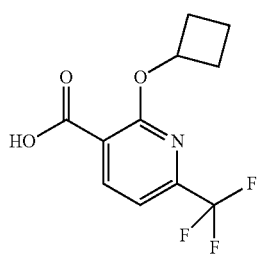 [SMILES: O=C(O)c1ccc(C(F)(F)F)nc1OC1CCC1]

The reaction is carried out under a nitrogen atmosphere. To a solution of cyclobutanol (2.11 mL; 26.9 mmol) in 50 mL dichloromethane and 5 mL tetrahydrofuran is added sodium hydride (55% in mineral oil) (1.12 g; 25.6 mmol) in portions over 5 minutes. After stirring for 15 minutes at room temperature, the reaction mixture is cooled to 10° C. and 2-chloro-6-(trifluoromethyl)pyridine-3-carboxylic acid (1.50 g; 6.32 mmol) is added to the reaction. The reaction mixture is stirred for 10 minutes at 0° C. and overnight at room temperature. The reaction is quenched with ice water and stirred for 10 minutes. The separated organic layer is extracted two times with water. The aqueous layer is washed with ethyl acetate and 20 g sodium chloride is added to the aqueous layer. The aqueous layer is acidified with KHSO₄ and extracted two times with dichloromethane. The combined organic layers are dried and concentrated under reduced pressure.

Yield: 1.94 g (100% of theory)
Mass spectrometry (ESI⁺): m/z=262 [M+H]⁺
HPLC (Method 4): Retention time=1.011 min.

Step B

[2-Cyclobutoxy-6-(trifluoromethyl)pyridin-3-yl]methanol

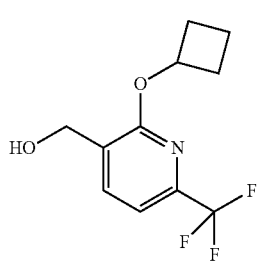 [SMILES: OCc1ccc(C(F)(F)F)nc1OC1CCC1]

To a solution of 2-cyclobutoxy-6-(trifluoromethyl)pyridine-3-carboxylic acid (1.94 g; 6.31 mmol) in 50 mL tetrahydrofuran is added borane tetrahydrofuran complex (1M solution in tetrahydrofuran) (18.9 mL; 18.9 mmol) and the reaction mixture is stirred for 1 hour at room temperature. The reaction mixture is quenched with HCl (1M aqueous solution) and extracted two times with dichloromethane. The combined organic layers are dried and concentrated under reduced pressure.

Yield: 1.65 g (100% of theory)
Mass spectrometry (ESI+): m/z=248 [M+H]+
HPLC (Method 4): Retention time=1.036 min Intermediate 4.7.B Step A 2-Ethoxy-6-(trifluoromethyl)pyridine-3-carboxylic acid

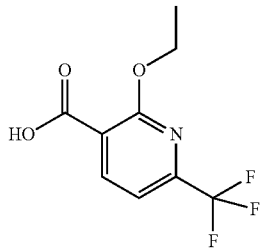 [SMILES: CCOc1nc(C(F)(F)F)ccc1C(=O)O]

A mixture of 2-chloro-6-(trifluoromethyl)pyridine-3-carboxylic acid (500 mg; 2.22 mmol) and sodium ethanolate (7.54 mg; 11.1 mmol) in 10 mL ethanol are stirred for 3 hours at reflux. The reaction is quenched with HCl (1M aqueous solution) and extracted two times with dichloromethane. The combined organic layers are dried and concentrated under reduced pressure.

Yield: 523 mg (100% of theory)
Mass spectrometry (ESI+): m/z=236 [M+H]+
HPLC (Method 3): Retention time=1.013 min Step B

[2-Ethoxy-6-(trifluoromethyl)pyridin-3-yl]methanol

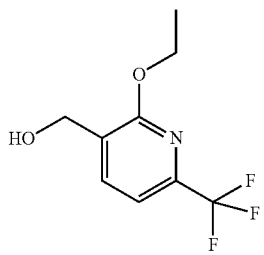

To a solution of 2-ethoxy-6-(trifluoromethyl)pyridine-3-carboxylic acid (919 mg; 3.91 mmol) in 10 mL tetrahydrofuran is added borane tetrahydrofuran complex (1M solution in tetrahydrofuran) (11.72 mL; 11.72 mmol) and the reaction is stirred for 3 hours at room temperature. The reaction is quenched with HCl (1M aqueous solution) and extracted two times with dichloromethane. The combined organic layers are dried and concentrated under reduced pressure.

Yield: 873 mg (100% of theory)
Mass spectrometry (ESI+): m/z=222 [M+H]+
HPLC (Method 3): Retention time=1.006 min Intermediate 4.8.0

Step A

Ethyl 6-oxo-1,6-dihydropyridine-2-carboxylate

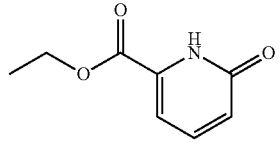

To a suspension of 6-oxo-1,6-dihydropyridine-2-carboxylic acid (400 mg; 2.88 mmol) in 10 mL ethanol is added thionyl chloride (315 µL; 4.31 mmol) and the reaction mixture is stirred for 90 minutes at reflux. The reaction mixture is concentrated under reduced pressure.

Yield: 480 mg (100% of theory)
Mass spectrometry (ESI+): m/z=168 [M+H]+)
HPLC (Method 3): Retention time=0.663 min.

Step B

Ethyl 6-(difluoromethoxy)pyridine-2-carboxylate

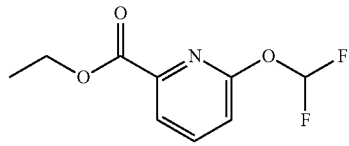

To a solution of ethyl 6-oxo-1,6-dihydropyridine-2-carboxylate (240 mg; 1.44 mmol) in 15 mL of acetonitrile is added sodium hydride (55% in mineral oil) (170 mg; 3.88 mmol) and the reaction mixture is stirred for a few minutes. 2,2-difluoro-2-sulfoacetic acid (252 µL; 2.44 mmol) is added and the reaction mixture is stirred for 30 minutes at room temperature. The reaction mixture is quenched with water and extracted with ethyl acetate. The organic layer is dried and concentrated under reduced pressure.

Yield: 260 mg (83% of theory)
Mass spectrometry (ESI+): m/z=218 [M+H]+
HPLC (Method 3): Retention time=0.974 min.

Step C

[6-(Difluoromethoxy)pyridin-2-yl]methanol

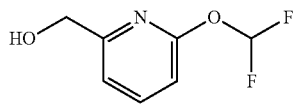 [SMILES: OCc1cccc(OC(F)F)n1]

To a solution of ethyl 6-(difluoromethoxy)pyridine-2-carboxylate (260 mg; 1.20 mmol) in 5 mL of tetrahydrofuran is added borane tetrahydrofuran complex (1M solution in tetrahydrofuran) (3.60 mL; 3.59 mmol) and the reaction mixture is stirred for 3 hours at room temperature. The reaction mixture is quenched with HCl (1M aqueous solution) and extracted two times with dichloromethane. The combined organic layers are dried and concentrated under reduced pressure.

Yield: 210 mg (100% of theory)
Mass spectrometry (ESI$^+$): m/z=176 [M+H]$^+$
HPLC (Method 4): Retention time=0.715 min Intermediate 4.10.B Step A 6-Fluoro-2-methoxypyridine-3-carboxylic acid

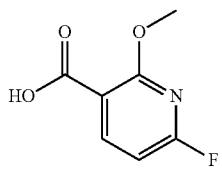

The reaction is carried out under a nitrogen atmosphere. To a mixture of methanol (1.53 mL; 38.21 mmol), 50 mL of dichloromethane and 10 mL of tetrahydrofuran is added sodium hydride (55% in mineral oil) (1.58 mg; 36.28 mmol) in portions and the reaction mixture is stirred for 15 minutes at room temperature. The reaction mixture is cooled to 10° C. and 2,6-difluoropyridine-3-carboxylic acid (1.50 g; 8.96 mmol) is added and the mixture is stirred at room temperature overnight. The reaction mixture is acidified with HCl (4M aqueous solution) and extracted two times with dichloromethane. The combined organic layers are dried and concentrated under reduced pressure.

Yield: 2.04 g (100% of theory)
HPLC (Method 2): Retention time=0.769 min

Step B (6-Fluoro-2-methoxypyridin-3-yl)methanol

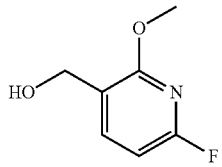

To 6-fluoro-2-methoxypyridine-3-carboxylic acid (1.00 g; 4.38 mmol) in 20 mL tetrahydrofuran is added lithium aluminium hydride (2 M in tetrahydrofuran) (3.28 mL; 6.57 mmol) and the reaction mixture is stirred for 3 hours at room temperature. The reaction mixture is quenched with HCl (4M aqueous solution) and extracted two times with dichloromethane. The combined organic layers are dried and concentrated under reduced pressure.

Yield: 849 mg (99% of theory)
HPLC (Method 7): Retention time=0.717 min.

Intermediate 7.4.A 2-(2,2-Difluoropropoxy)-6-methylpyridine-3-carbonitrile

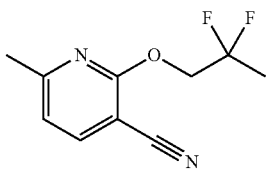

2-Chloro-6-methylpyridine-3-carbonitrile (600 mg; 3.93 mmol) in 10 mL of N,N-dimethylformamide is cooled to 0° C. and sodium hydride (55% in mineral oil) (429 mg; 9.83 mmol) is added to the reaction mixture. After stirring for a few minutes, 2,2-difluoropropanol (453 mg; 4.72 mmol) is added and the reaction mixture is stirred for 2 hours at 50° C. The reaction mixture is quenched with methanol, filtered and purified by reverse phase chromatography-HPLC (modifier: trifluoroacetic acid)

Yield: 355 mg (43% of theory)
Mass spectrometry (ESI$^+$): m/z=213 [M+H]$^+$
HPLC (Method 3): Retention time=1.020 min.

Intermediate 7.11.A

Step A 2-(Difluoromethoxy)-6-methylpyridine-3-carbonitrile

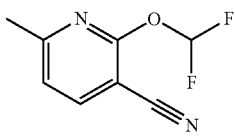

To 2-hydroxy-6-methylpyridine-3-carbonitrile (1.00 g; 7.46 mmol) in 30 mL acetonitrile is added sodium hydride (55% in mineral oil) (878 mg; 20.1 mmol) and the reaction mixture is stirred for a few minutes at room temperature. 2,2-difluoro-2-sulfoacetic acid (1.31 mL; 12.7 mmol) is added and the reaction mixture is stirred overnight at room temperature. The reaction is quenched with water and extracted with ethyl acetate. The organic layer is dried and concentrated under reduced pressure. The residue is purified by reverse phase chromatography-HPLC (modifier: ammonium hydroxide).

Yield: 654 mg (48% of theory)
Mass spectrometry (ESI$^+$): m/z=185 [M+H]$^+$)
HPLC (Method 1): Retention time=0.899 min.

Preparation of the Final Compounds

Procedure 1

Step A

5-Bromo-2-carboxypyridin-1-ium-1-olate

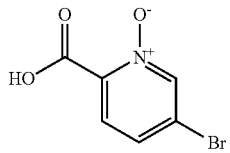

5-Bromopyridine-2-carboxylic acid (40.0 g; 0.20 mol) in 750 mL of acetonitrile is cooled to 0° C. and hydrogen peroxide-urea adduct (39.1 g; 0.42 mol) is added and the reaction mixture is stirred for 20 minutes at 0° C. Trifluoroacetic acid anhydride (67.1 mL; 0.88 mol) is added in portions and the reaction mixture is stirred overnight at room temperature. The reaction is quenched with NaHCO$_3$ (saturated aqueous solution) and extracted three times with dichloromethane. The combined organic layers are dried and concentrated under reduced pressure. The residue is basified with NaOH (1M aqueous solution) and extracted with dichloromethane. The aqueous layer is acidified with HCl (1M aqueous solution), the precipitate is filtered off and dried.

Yield: 36.5 g (85% of theory)

Mass spectrometry (ESI$^+$): m/z=218/220 [M+H]$^+$ (Br)

HPLC (Method 3): Retention time=0.569 min.

Step B

Methyl 5-bromo-6-chloropyridine-2-carboxylate

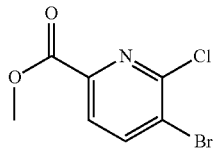

A mixture of 5-bromo-2-carboxypyridin-1-ium-1-olate (7.00 g; 25.7 mmol) in 5 mL of phosphorus oxychloride is stirred for 1 hour at 100° C. The reaction is cooled to 0° C. and quenched with methanol. NaHCO$_3$ (saturated aqueous solution) is added and the reaction mixture is extracted two times with dichloromethane. The combined organic layers are dried and concentrated under reduced pressure. The residue is purified by silica gel chromatography (eluent: dichloromethane/methanol 0%→25%).

Yield: 2.13 g (33% of theory)

Mass spectrometry (ESI$^+$): m/z=250, 252, 254 [M+H]$^+$ (Br/Cl)

HPLC (Method 3): Retention time=0.927 min.

Step C (5-Bromo-6-chloropyridin-2-yl)methanol

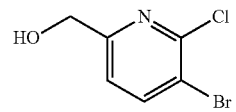

Methyl 5-bromo-6-chloropyridine-2-carboxylate (1.06 g; 4.23 mmol) in 50 mL of tetrahydrofuran is cooled to 0° C. and lithium borohydride (2 M in tetrahydrofuran) (3.17 mL; 6.35 mmol) is added dropwise. After stirring for 15 minutes at 0° C., the reaction is stirred at room temperature for 30 minutes. The reaction is quenched with HCl (1M aqueous solution) and extracted two times with dichloromethane. The combined organic layers are dried and concentrated under reduced pressure.

Yield: 930 mg (99% of theory)

Mass spectrometry (ESI$^+$): m/z=222/224/226 [M+H]$^+$ (Br/Cl)

HPLC (Method 3): Retention time=0.808 min.

Step D

3-Bromo-6-(bromomethyl)-2-chloropyridine

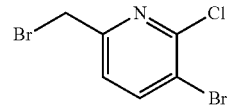

To a solution of (5-bromo-6-chloropyridin-2-yl)methanol (930 mg; 4.18 mmol) in 30 mL of dichloromethane is added dropwise phosphorous tribromide (238 μL: 2.53 mmol) at 0° C. After stirring for 15 minutes at 0° C., the reaction mixture is quenched with cooled NaHCO$_3$ (saturated aqueous solution) and extracted two times with dichloromethane. The combined organic layers are dried and concentrated under reduced pressure.

Yield: 980 mg (82% of theory)

Mass spectrometry (ESI$^+$): m/z=284/286/290 [M+H]$^+$ (2Br/Cl)

HPLC (Method 3): Retention time=1.053 min.

Step E

2-[(5-Bromo-6-chloropyridin-2-yl)methyl]-3-oxobutanenitrile

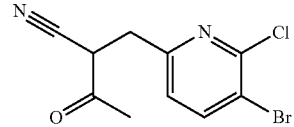

A solution of cyanoacetone sodium salt (CAS: 70807-22-6; 469 mg; 4.05 mmol) in 5 mL of N,N-dimethylformamide and 75 μL of water is cooled to 0° C. and 3-bromo-6-(bromomethyl)-2-chloropyridine (850 mg; 2.98 mmol) in 2.5 mL N,N-dimethylformamide is added dropwise. After stirring for 3 hours at room temperature, the reaction is concentrated under reduced pressure to provide the crude product, which was used directly in the next step.

Yield: 390 mg (46% of theory)

Mass spectrometry (ESI⁺): m/z=287/289/291 [M+H]⁺ (Br/Cl)

HPLC (Method 3): Retention time=0.961 min.

Step F

6-[(5-Bromo-6-chloropyridin-2-yl)methyl]-5-methyl-[1,2,4]triazolo[1,5-a]pyrimidin-7-amine

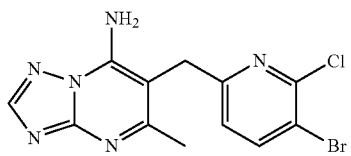 [SMILES: Cc1nc2ncnn2c(N)c1Cc1ccc(Br)c(Cl)n1]

A mixture of 2-[(5-bromo-6-chloropyridin-2-yl)methyl]-3-oxobutanenitrile (390 mg; 1.36 mmol), 1H-1,2,4-triazol-3-amine (114 mg; 1.36 mmol) and pivalic acid (800 mg; 7.89 mmol) is stirred at 120° C. for a few hours until HPLC indicated complete conversion. The reaction is quenched with methanol, the precipitate is filtered off and washed with methanol.

Yield: 260 mg (54% of theory)

Mass spectrometry (ESI⁺): m/z=353/355/357 [M+H]⁺ (Br/Cl)

HPLC (Method 3): Retention time=0.835 min.

Step G

Example 1.1

6-{[5-Bromo-6-(2,2-difluoropropoxy)pyridin-2-yl]methyl}-5-methyl-[1,2,4]triazolo[1,5-a]pyrimidin-7-amine

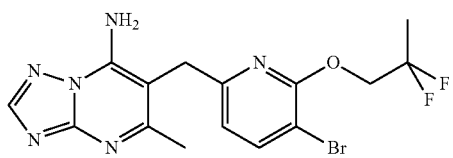 [SMILES: Cc1nc2ncnn2c(N)c1Cc1ccc(Br)c(OCC(C)(F)F)n1]

To 2,2-difluoropropan-1-ol (20.4 mg; 0.212 mmol) in 1.5 mL of dimethyl sulfoxide is added potassium hydroxide (19.8 mg; 0.354 mmol) and the mixture is stirred for a few minutes at room temperature. 6-[(5-Bromo-6-chloropyridin-2-yl)methyl]-5-methyl-[1,2,4]triazolo[1,5-a]pyrimidin-7-amine (50.0 mg; 0.141 mmol) is added and the reaction mixture is stirred for 1 hour at 120° C. The reaction is quenched with methanol, filtered and purified by reverse phase chromatography-HPLC (modifier: ammonium hydroxide).

Yield: 20 mg (34% of theory)

Mass spectrometry (ESI⁺): m/z=413/415 [M+H]⁺ (Br)

HPLC (Method 1): Retention time=0.911 min.

Analogously to Example 1.1 step A to step F, the following examples are prepared using [3-bromo-4-(difluoromethoxy)phenyl]methanol as the starting material for step D and 2-bromo-4-(bromomethyl)-1-(difluoromethoxy)benzene as the starting material for step E:

| Example | | Mass spectrometry | HPLC Retention time |
|---|---|---|---|
| 1.2 | 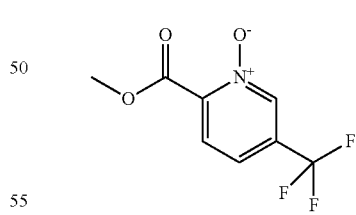 | (ESI⁻): m/z = 384 [M]⁺ | (Method 1): 0.858 min |

Procedure 2

Step A 2-(Methoxycarbonyl)-5-(trifluoromethyl)pyridin-1-ium-1-olate

Methyl 5-(trifluoromethyl)pyridine-2-carboxylate (15.0 g; 73.1 mmol) in 200 mL of acetonitrile is cooled to 0° C. and hydrogen peroxide-urea adduct (14.4 g; 0.15 mol) is added to the reaction mixture. After stirring for 20 minutes, trifluoroacetic acid anhydride (11.2 mL; 0.15 mol) is added and the reaction mixture is stirred for a few minutes at room temperature. The reaction is quenched with NaHCO₃ (saturated aqueous solution) and extracted three times with dichloromethane. The combined organic layers are dried and concentrated under reduced pressure. The residue is further used as crude product.

Yield: 19.5 g (97% of theory)

Mass spectrometry (ESI+): m/z=222 [M+H]+

HPLC (Method 3): Retention time=0.700 min.

Step B

Methyl 6-chloro-5-(trifluoromethyl)pyridine-2-carboxylate

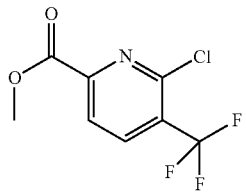

A mixture of 2-(methoxycarbonyl)-5-(trifluoromethyl)pyridin-1-ium-1-olate (10.0 g; 36.2 mmol) in 10 mL of phosphor oxychloride is stirred for 2 days at 60° C. The reaction is stirred at 0° C. and quenched with methanol. NaHCO₃ (saturated aqueous solution) is added and the reaction mixture is extracted with dichloromethane. The organic layer is dried and concentrated under reduced pressure. The residue is purified by silica gel chromatography (eluent: dichloromethane/ethyl acetate 0→10%).

Yield: 3.1 g (36% of theory)

Mass spectrometry (ESI+): m/z=240/242 [M+H]+ (Cl)

HPLC (Method 3): Retention time=0.993 min.

Step C

Methyl 6-(furan-2-yl)-5-(trifluoromethyl)pyridine-2-carboxylate

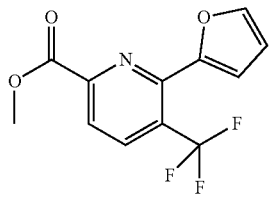 [SMILES: COC(=O)c1ccc(C(F)(F)F)c(-c2ccco2)n1]

A mixture of methyl 6-chloro-5-(trifluoromethyl)pyridine-2-carboxylate (200 mg; 0.83 mmol), (furan-2-yl)boronic acid (158 mg; 1.42 mmol), potassium carbonate (2M aqueous solution) (793 µL; 1.58 mmol) in 4 mL of dioxane is stirred under argon. [1,1'-bis(di-tert-butylphosphino)-ferrocene]palladium (II) dichloride (163 mg; 0.250 mmol) is added and the reaction mixture is stirred at 100° C. for 1 hour. The reaction is quenched with methanol and purified by reverse phase chromatography-HPLC (modifier: trifluoroacetic acid).

Yield: 165 mg (73% of theory)

Mass spectrometry (ESI+): m/z=272 [M+H]+

HPLC (Method 1): Retention time=1.038 min.

Step D

[6-(Furan-2-yl)-5-(trifluoromethyl)pyridin-2-yl]methanol

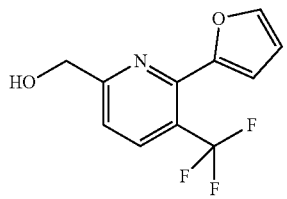 [SMILES: OCc1ccc(C(F)(F)F)c(-c2ccco2)n1]

A mixture of methyl 6-(furan-2-yl)-5-(trifluoromethyl)pyridine-2-carboxylate (165 mg; 0.61 mmol) in 10 mL of tetrahydrofuran is cooled to 0° C. and lithium aluminium hydride (2 M in tetrahydrofuran) (0.31 mL; 0.61 mmol) is added dropwise After stirring for 15 minutes at 0° C., the reaction is quenched with NaHCO₃ (saturated aqueous solution) and extracted two times with dichloromethane. The combined organic layers are dried and concentrated under reduced pressure.

Yield: 148 mg (100% of theory)

HPLC (Method 3): Retention time=0.913 min.

Step E 6-(Bromomethyl)-2-(furan-2-yl)-3-(trifluoromethyl)pyridine

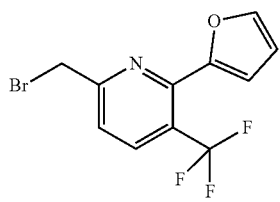 [SMILES: FC(F)(F)c1ccc(CBr)nc1-c1ccco1]

To a solution of [6-(furan-2-yl)-5-(trifluoromethyl)pyridin-2-yl]methanol (148 mg; 0.61 mmol) in 10 mL of dichloromethane is added dropwise phosphorus tribromide (34.3 µL; 0.37 mmol) at 0° C. After stirring for 15 minutes at 0° C., the reaction is stirred for 4 hours at room temperature. The reaction is quenched with cooled NaHCO₃ (half saturated aqueous solution) and extracted two times with dichloromethane. The combined organic layers are dried and concentrated under reduced pressure.

Yield: 186 mg (100% of theory)

Mass spectrometry (ESI+): m/z=306/308 [M+H]+ (Br)

HPLC (Method 3): Retention time=1.109 min.

Step F

2-{[6-(Furan-2-yl)-5-(trifluoromethyl)pyridin-2-yl]methyl}-3-oxobutanenitrile

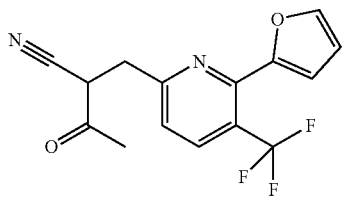 [SMILES: CC(=O)C(C#N)Cc1ccc(C(F)(F)F)c(-c2ccco2)n1]

A solution of cyanoacetone sodium salt (CAS: 70807-22-6; 127 mg; 1.22 mmol) in 4 mL of N,N-dimethylformamide and 100 μL of water is cooled to 0° C. and 6-(bromomethyl)-2-(furan-2-yl)-3-(trifluoromethyl)pyridine (186 mg; 0.61 mmol) in 2 mL of N,N-dimethylformamide is added dropwise. After stirring for 4 hours, the reaction is concentrated under reduced pressure to provide a crude product, which is used directly in the next step.

Yield: 187 mg (100% of theory)
Mass spectrometry (ESI$^+$): m/z=309 [M+H]$^+$
HPLC (Method 1): Retention time=0.650 min.

Step G

Example 2.1

6-{[6-(Furan-2-yl)-5-(trifluoromethyl)pyridin-2-yl]methyl}-5-methyl-[1,2,4]triazolo[1,5-a]pyrimidin-7-amine

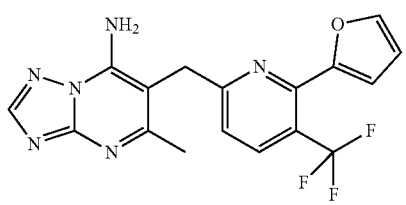 [SMILES: Cc1nc2ncnn2c(N)c1Cc1ccc(C(F)(F)F)c(-c2ccco2)n1]

A mixture of 2-{[6-(furan-2-yl)-5-(trifluoromethyl)pyridin-2-yl]methyl}-3-oxobutanenitrile (187 mg; 0.61 mmol), 1H-1,2,4-triazol-3-amine (76.5 mg; 0.91 mmol) and pivalic acid (400 mg; 3.96 mmol) is stirred at 120° C. for a few hours. The reaction is quenched with methanol and purified by reverse phase chromatography-HPLC (modifier: trifluoroacetic acid).

Yield: 16 mg (5% of theory)
Mass spectrometry (ESI$^+$): m/z=375 [M+H]$^+$
HPLC (Method 3): Retention time=0.907 min.

Analogously to Example 2.1, the following examples are prepared using [[3-bromo-4-(trifluoromethyl)phenyl as the starting material for step C and replacing phosphorus tribromide by thionyl for step E:

| Example | Structure | Mass spectrometry | HPLC Retention time |
|---|---|---|---|
| 2.2 | 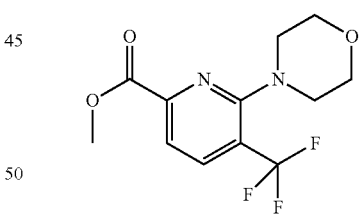 | (ESI$^-$): m/z = 384 [M + H]$^+$ | (Method 1): 0.858 min |

Procedure 3

Step A

Methyl 6-(morpholin-4-yl)-5-(trifluoromethyl)pyridine-2-carboxylate

A mixture of methyl 6-chloro-5-(trifluoromethyl)pyridine-2-carboxylate (see procedure 2, step B) (200 mg; 0.83 mmol), morpholine (73 μL; 0.83 mmol); N,N-diisopropylethylamine (159 μL; 0.92 mmol) and 3 mL of dimethyl sulfoxide is stirred for 1 hour at 120° C. The reaction is quenched with methanol, filtered and purified by reverse phase chromatography-HPLC (modifier: trifluoroacetic acid).

Yield: 110 mg (45% of theory)
Mass spectrometry (ESI$^+$): m/z=291 [M+H]$^+$
HPLC (Method 3): Retention time=1.021 min.

Step B

[6-(Morpholin-4-yl)-5-(trifluoromethyl)pyridin-2-yl]methanol

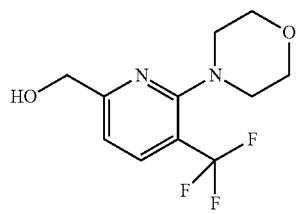

To methyl 6-(morpholin-4-yl)-5-(trifluoromethyl)pyridine-2-carboxylate (110 mg; 0.38 mmol) in 10 mL of tetrahydrofuran is added dropwise solution of lithium aluminium hydride (2M in tetrahydrofuran) (0.189 mL; 0.38 mmol) at 0° C. and the reaction mixture is stirred for 15 minutes. The reaction is quenched with NaHCO$_3$ (saturated aqueous solution) and extracted two times with dichloromethane. The combined organic layers are dried and concentrated under reduced pressure.

Yield: 99 mg (100% of theory)

Mass spectrometry (ESI$^+$): m/z=263 [M+H]$^+$

HPLC (Method 3): Retention time=0.912 min.

Step C

4-[6-(Bromomethyl)-3-(trifluoromethyl)pyridin-2-yl]morpholine

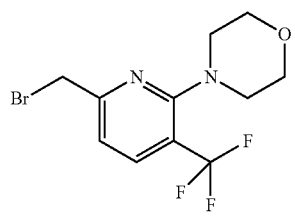 [SMILES: FC(F)(F)c1ccc(CBr)nc1N1CCOCC1]

To a solution of [6-(morpholin-4-yl)-5-(trifluoromethyl)pyridin-2-yl]methanol (99 mg; 0.38 mmol) in 10 mL of dichloromethane is added dropwise phosphorus tribromide (21 µL; 0.23 mmol) at 0° C. and the reaction mixture is stirred for 15 minutes. After stirring for 4 hours at room temperature, the reaction is quenched with cooled NaHCO$_3$ (half saturated aqueous solution) and extracted two times with dichloromethane. The combined organic layers are dried and concentrated under reduced pressure.

Yield: 122 mg (99% of theory)

Mass spectrometry (ESI$^+$): m/z=325/327 [M+H]$^+$ (Br)

HPLC (Method 3): Retention time=1.131 min.

Step D

2-{[6-(Morpholin-4-yl)-5-(trifluoromethyl)pyridin-2-yl]methyl}-3-oxobutanenitrile

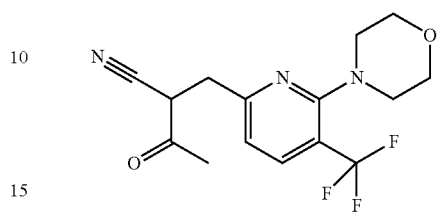

A solution of cyanoacetone sodium salt (CAS: 70807-22-6; 78.8 mg; 0.75 mmol) in 4 mL of N,N-dimethylformamide and 100 µL of water is cooled to 0° C. and 4-[6-(bromomethyl)-3-(trifluoromethyl)pyridin-2-yl]morpholine (122 mg; 0.38 mmol) in 2 mL of N,N-dimethylformamide is added dropwise and the reaction is stirred for 5 hours at 0° C. The reaction is concentrated under reduced pressure to provide a crude product, which is used directly in the next step.

Yield: 122 mg (99% of theory)

Mass spectrometry (ESI$^+$): m/z=328 [M+H]$^+$

HPLC (Method 2): Retention time=0.994 min.

Step E

Example 3.1

5-Methyl-6-{[6-(morpholin-4-yl)-5-(trifluoromethyl)pyridin-2-yl]methyl}-[1,2,4]triazolo[1,5-a]pyrimidin-7-amine

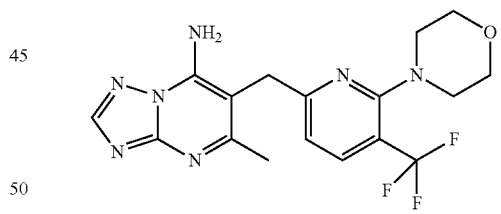

A mixture of 2-{[6-(morpholin-4-yl)-5-(trifluoromethyl)pyridin-2-yl]methyl}-3-oxobutanenitrile (122 mg; 0.37 mmol), 1H-1,2,4-triazol-3-amine (31.3 mg; 0.37 mmol) and pivalic acid (400 mg; 3.96 mmol) is stirred at 120° C. for 4 hours. The reaction is quenched with methanol, filtered and purified by reverse phase chromatography-HPLC (modifier: trifluoroacetic acid).

Yield: 20 mg (11% of theory)

Mass spectrometry (ESI$^+$): m/z=394 [M+H]$^+$

HPLC (Method 3): Retention time=0.890 min.

Analogously to Example 3.1, the following examples are prepared using methyl 6-chloro (trifluoromethyl)pyridine-2-carboxylate and the corresponding amines:

| Example | | Mass spectrometry | HPLC Retention time |
|---|---|---|---|
| 3.2 | (structure) | (ESI+): m/z = 414 [M + H]+ | (Method 3): 0.965 min |
| 3.3 | (structure) | (ESI+): m/z = 400 [M + H]+ | (Method 3): 0.961 min |
| 3.4 | (structure) | (ESI+): m/z = 324 [M + H]+ | (Method 3): 0.740 min |

For example 3.4 (2,4-dimethoxyphenyl)methanamine was used as the amine

Procedure 4

Step A

2-Bromo-6-(bromomethyl)-3-(difluoromethoxy)pyridine

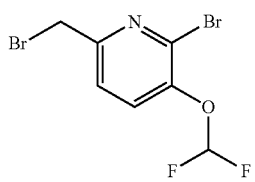 [SMILES: FC(F)Oc1ccc(CBr)nc1Br]

To a solution of [6-bromo-5-(difluoromethoxy)pyridin-2-yl]methanol (2.00 g; 7.09 mmol) (Intermediate 4.1.A) in 20 mL dichloromethane is added dropwise phosphorus tribromide (0.400 mL; 4.25 mmol) at 0° C. and the reaction is stirred for 15 minutes. The reaction is quenched with cooled NaHCO₃ (half saturated aqueous solution) and extracted two times with dichloromethane. The combined organic layers are dried and concentrated under reduced pressure.

Yield: 2.25 g (100% of theory)

Mass spectrometry (ESI+): m/z=316 [M+H]+

Step B

2-{[6-Bromo-5-(difluoromethoxy)pyridin-2-yl]methyl}-3-oxobutanenitrile

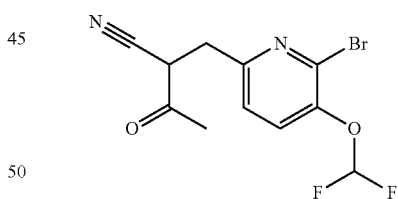

A solution of cyanoacetone sodium salt (CAS: 70807-22-6; 2.98 g; 25.4 mmol) in 30 mL of N,N-dimethylformamide and 500 µL of water is cooled to 0° C. and 2-bromo-6-(bromomethyl)-3-(difluoromethoxy)pyridine (2.25 g; 7.10 mmol) in 5 mL of N,N-dimethylformamide is added dropwise and the reaction is stirred for 3 hours at room temperature. The reaction mixture is purified by reverse phase chromatography-HPLC (modifier: trifluoroacetic acid).

Yield: 0.980 mg (43% of theory)

57

Step C

Example 4.1

6-{[6-Bromo-5-(difluoromethoxy)pyridin-2-yl]methyl}-5-methyl-[1,2,4]triazolo[1,5-a]pyrimidin-7-amine

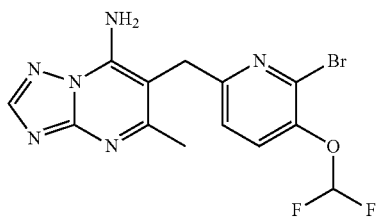 [SMILES: Cc1nc2ncnn2c(N)c1Cc1ccc(OC(F)F)c(Br)n1]

58

A mixture of 2-{[6-bromo-5-(difluoromethoxy)pyridin-2-yl]methyl}-3-oxobutanenitrile (980 mg; 3.07 mmol), 1H-1,2,4-triazol-3-amine (387 mg; 4.61 mmol) and pivalic acid (1.5 g; 14.74 mmol) is stirred at 120° C. for 1 hour. The reaction is quenched with methanol, the precipitate is filtered off and washed with methanol. The precipitate is suspended in acetonitrile, methanol, water, N,N-dimethylformamide and trifluoroacetic acid. The precipitate is filtered off and dried.

Yield: 703 mg (59% of theory)
Mass spectrometry (ESI$^+$): m/z=385, 387 [M+H]$^+$ (Br)
HPLC (Method 2): Retention time=0.744 min.

Following examples are prepared analogously to procedure 4 starting with an appropriate alcohol

| Example | Structure | Mass spectrometry | HPLC Retention time | Starting material for Step A |
|---|---|---|---|---|
| 4.2 | 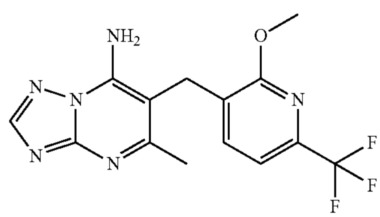 [SMILES: COc1nc(C(F)(F)F)ccc1Cc1c(C)nc2ncnn2c1N] | (ESI$^+$): m/z = 339 [M + H]$^+$ | (Method 7): 0.869 min | [2-methoxy-6-(trifluoromethyl)-pyridin-3-yl]-methanol (Intermediate 4.2.B) |
| 4.3 | 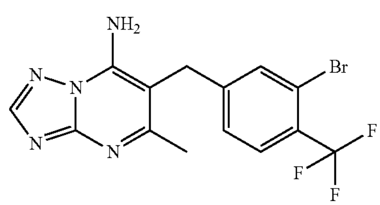 [SMILES: Cc1nc2ncnn2c(N)c1Cc1ccc(C(F)(F)F)c(Br)c1] | (ESI$^+$): m/z = 386/388 [M + H]$^+$ (Br) | (Method 3): 0.923 min | [3-bromo-4-(trifluoromethyl)-phenyl]-methanol |
| 4.4 | 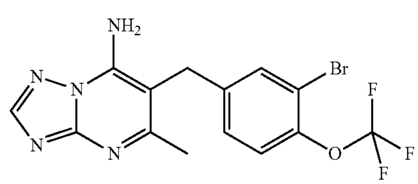 [SMILES: Cc1nc2ncnn2c(N)c1Cc1ccc(OC(F)(F)F)c(Br)c1] | (ESI$^+$): m/z = 402/404 [M + H]$^+$ (Br) | (Method 3): 0.954 min | [3-bromo-4-(trifluoromethoxy)-phenyl]-methanol |
| 4.5 | 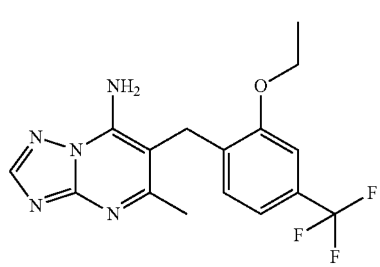 [SMILES: CCOc1cc(C(F)(F)F)ccc1Cc1c(C)nc2ncnn2c1N] | (ESI$^+$): m/z = 352 [M + H]$^+$ | (Method 3): 0.934 min | [2-ethoxy-4-(trifluoromethyl)-phenyl]-methanol (Intermediate 4.5.B) |

-continued

| Example | Structure | Mass spectrometry | HPLC Retention time | Starting material for Step A |
|---|---|---|---|---|
| 4.6 | 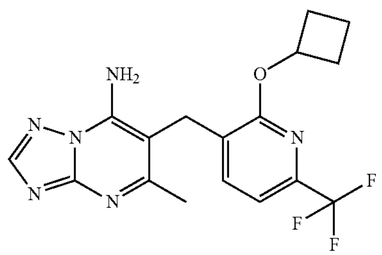 [SMILES: Cc1nc2ncnn2c(N)c1Cc1ccc(C(F)(F)F)nc1OC1CCC1] | (ESI⁺): m/z = 379 [M + H]⁺ | (Method 4): 0.999 min | [2-cyclobutoxy-6-(trifluoro-methyl)-pyridin-3-yl]-methanol (Intermediate 4.6.B) |
| 4.7 | 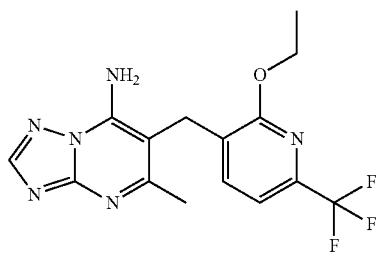 [SMILES: CCOc1nc(C(F)(F)F)ccc1Cc1c(C)nc2ncnn2c1N] | (ESI⁺): m/z = 353 [M + H]⁺ | (Method 3): 0.953 min | [2-ethoxy-6-(trifluoro-methyl)-pyridin-3-yl]-methanol (Intermediate 4.7.B) |
| 4.8 | 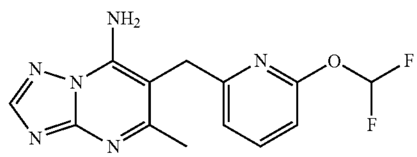 [SMILES: Cc1nc2ncnn2c(N)c1Cc1cccc(OC(F)F)n1] | (ESI⁺): m/z = 307 [M + H]⁺ | (Method 1): 0.79 min | [6-(difluoro-methoxy)-pyridin-2-yl]-methanol (Intermediate 4.8.C) |
| 4.9 | 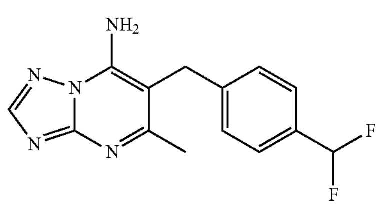 [SMILES: Cc1nc2ncnn2c(N)c1Cc1ccc(C(F)F)cc1] | (ESI⁺): m/z = 290 [M + H]⁺ | (Method 1): 0.787 min | [4-(difluoro-methyl)-phenyl]-methanol (Intermediate 4.9.B) |

Procedure 5

Step A 6-({7-Amino-5-methyl-[1,2,4]triazolo[1,5-a]pyrimidin-6-yl}methyl)-3-bromo-1,2-dihydropyridin-2-one

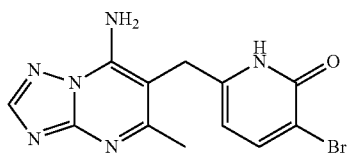 [SMILES: Cc1nc2ncnn2c(N)c1Cc1ccc(Br)c(=O)[nH]1]

To 6-[(5-bromo-6-chloropyridin-2-yl)methyl]-5-methyl-[1,2,4]triazolo[1,5-a]pyrimidin-7-amine (450 mg; 1.27 mmol) (see procedure 1, step F) is added KOH (10M aqueous solution) (2.0 mL; 20 mmol) and the reaction is stirred for a few hours at 120° C. The reaction is acidified with HCl (4M aqueous solution) and extracted with dichloromethane. The aqueous layer is concentrated under reduced pressure.

Yield: 400 mg (94% of theory)
Mass spectrometry (ESI⁺): m/z=335/337 [M+H]⁺ (Br)
HPLC (Method 1): Retention time=0.553 min.

Step B

Example 5.1

6-{[5-Bromo-6-(difluoromethoxy)pyridin-2-yl]methyl}-5-methyl-[1,2,4]triazolo[1,5-a]pyrimidin-7-amine

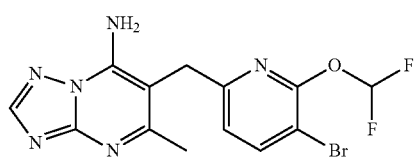 [SMILES: Cc1nc2ncnn2c(N)c1Cc1ccc(Br)c(OC(F)F)n1]

6-({7-Amino-5-methyl-[1,2,4]triazolo[1,5-a]pyrimidin-6-yl}methyl)-3-bromo-1,2-dihydropyridin-2-one (74 mg; 0.22 mmol) is suspended in 7 mL of acetonitrile and sodium hydride (26 mg; 0.59 mmol) is added. After stirring for a few minutes at room temperature, 2,2-difluoro sulfoacetic acid (39 μL; 0.38 mmol) is added and the reaction mixture is stirred for 30 minutes. 2,2-difluoro-2-sulfoacetic acid (39 μL; 0.38 mmol) is added two times and the reaction mixture is stirred at room temperature until full conversion. The reaction is quenched with water and extracted with ethyl acetate. The organic layer is dried and concentrated under reduced pressure. The residue is purified by reverse phase chromatography-HPLC (modifier: ammonium hydroxide).

Yield: 24 mg (28% of theory)
Mass spectrometry (ESI$^+$): m/z=385/387 [M+H]$^+$ (Br)
HPLC (Method 1): Retention time=0.851 min.

Procedure 6

Step A

3-Oxo-2-{[4-(trifluoromethoxy)phenyl]methyl}butanenitrile

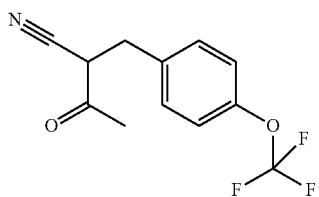 [SMILES: CC(=O)C(C#N)Cc1ccc(OC(F)(F)F)cc1]

A solution of cyanoacetone sodium salt (CAS: 70807-22-6; 500 mg; 4.76 mmol) in 12 mL of N,N-dimethylformamide and 200 μL of water is cooled to 0° C. and 1-(bromomethyl)-4-(trifluoromethoxy)benzene (0.506 mL; 3.17 mmol) in N,N-dimethylformamide is added dropwise and the reaction is stirred for 18 hours at room temperature. The residue is purified by reverse phase chromatography-HPLC (modifier: trifluoroacetic acid).

Yield: 135 mg (17% of theory)
Mass spectrometry (ESI$^+$): m/z=258 [M+H]$^+$
HPLC (Method 3): Retention time=1.025 min.

Step B

Example 6.1

5-methyl-6-{[4-(trifluoromethoxy)phenyl]methyl}-[1,2,4]triazolo[1,5-a]pyrimidin-7-amine

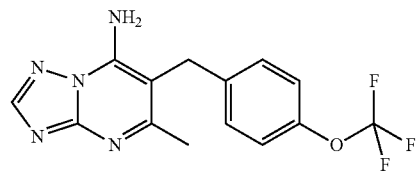 [SMILES: Cc1nc2ncnn2c(N)c1Cc1ccc(OC(F)(F)F)cc1]

A mixture of 3-oxo-2-{[4-(trifluoromethoxy)phenyl]methyl}butanenitrile (85 mg; 1.01 mmol), 1H-1,2,4-triazol-3-amine (130 mg; 0.51 mmol) and pivalic acid (206 mg; 2.02 mmol) is stirred at 140° C. for 2 hours. The reaction is quenched with methanol/acetonitril and the precipitate is filtered off, washed with acetonitrile and dried.

Yield: 100 mg (61% of theory)
Mass spectrometry (ESI$^+$): m/z=324 [M+H]$^+$
HPLC (Method 2): Retention time=0.831 min.

Following examples are prepared analogously to example 6.1 starting with cyanoacetone sodium salt and the appropriate bromide

| Example | Structure | Mass spectrometry | HPLC Retention time | Starting material for Step A |
|---|---|---|---|---|
| 6.2 | 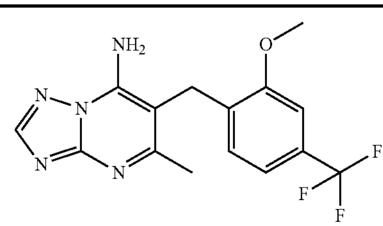 | (ESI$^+$): m/z = 338 [M + H]$^+$ | (Method 3): 0.888 min | 1-(bromomethyl)-2-methoxy-4-(trifluoromethyl)benzene |
| 6.3 | 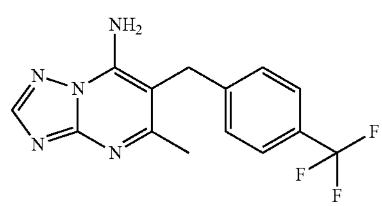 [SMILES: Cc1nc2ncnn2c(N)c1Cc1ccc(C(F)(F)F)cc1] | (ESI$^+$): m/z = 308 [M + H]$^+$ | (Method 2): 0.819 min | 1-(bromomethyl)-4-(trifluoromethyl)benzene |
| 6.4 | 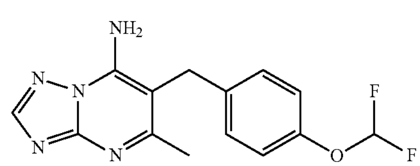 [SMILES: Cc1nc2ncnn2c(N)c1Cc1ccc(OC(F)F)cc1] | (ESI$^+$): m/z = 306 [M + H]$^+$ | (Method 1): 0.797 min | 1-(bromomethyl)-4-(difluoromethoxy)benzene |

| Example | Structure | Mass spectrometry | HPLC Retention time | Starting material for Step A |
|---|---|---|---|---|
| 6.5 | 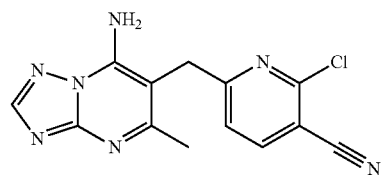 | (ESI+): m/z = 340 [M + H]+ | (Method 7): 0.882 min | 1-(chloro-methyl)-4-[(trifluoro-methyl)sulfanyl]benzene |

Procedure 7

Step A 6-(Bromomethyl)-2-chloropyridine-3-carbonitrile

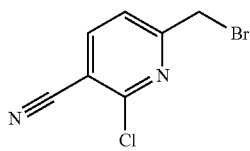

A mixture of 2-chloro-6-methylpyridine-3-carbonitrile (5.00 g; 31.8 mmol), 1-bromopyrrolidine-2,5-dione (9.05 g; 50.9 mmol), azobisisobutyronitrile (1.56 g; 9.54 mmol) in 60 mL of dichloromethane is stirred for 15 minutes at 110° C. in the microwave. 1-bromopyrrolidine-2,5-dione (500 mg; 2.81 mmol) and azobisisobutyronitrile (100 mg; 0.61 mmol) are added and the reaction is stirred for 30 minutes at 110° C. The reaction mixture is concentrated under reduced pressure and the residue is purified by silica gel chromatography (eluent: cyclohexene/ethyl acetate 0→20%).

Yield: 1.69 g (23% of theory)
Mass spectrometry (ESI+): m/z=231/233/235 [M+H]+ (Br/Cl)
HPLC (Method 4): Retention time=0.848 min.

Step B 6-(2-Acetyl-2-cyanoethyl)-2-chloropyridine-3-carbonitrile

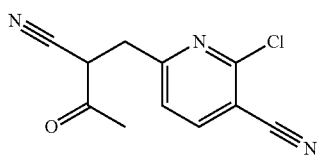 [SMILES: CC(=O)C(C#N)Cc1ccc(C#N)c(Cl)n1]

A solution of cyanoacetone sodium salt (CAS: 70807-22-6; 1.01 g; 9.66 mmol) in 8 mL of N,N-dimethylformamide and 240 µL water are cooled to 0° C. and 6-(bromomethyl)-2-chloropyridine-3-carbonitrile (1.49 g; 6.44 mmol) in 8 mL of N,N-dimethylformamide is added dropwise and the reaction is stirred at room temperature overnight. The reaction is concentrated under reduced pressure to provide a crude product, which is used directly in the next step.

Yield: 1.5 g (100% of theory)
Mass spectrometry (ESI+): m/z=232/234 [M+H]+ (Cl)
HPLC (Method 3): Retention time=0.877 min.

Step C 6-({7-Amino-5-methyl-[1,2,4]triazolo[1,5-a]pyrimidin-6-yl}methyl)-2-chloropyridine-3-carbonitrile

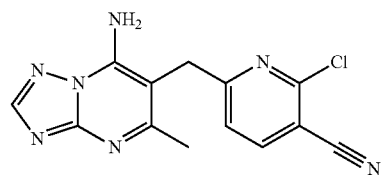 [SMILES: Cc1nc2ncnn2c(N)c1Cc1ccc(C#N)c(Cl)n1]

A mixture of 6-(2-acetyl-2-cyanoethyl)-2-chloropyridine-3-carbonitrile (1.50 g; 6.42 mmol), 1H-1,2,4-triazol-3-amine (648 mg; 7.70 mmol) and pivalic acid (1.30 g; 12.84 mmol) is stirred at 120° C. for 6 hours. The reaction is quenched with methanol and the precipitate is filtered off, washed with methanol and dried.

Yield: 280 mg (15% of theory)
Mass spectrometry (ESI+): m/z=300/302 [M+H]+ (Cl)
HPLC (Method 3): Retention time=0.715 min.

Step D

Example 7.1

6-({7-amino-5-methyl-[1,2,4]triazolo[1,5-a]pyrimidin-6-yl}methyl)-2-[(2,2-difluoroethyl)amino]pyridine-3-carbonitrile

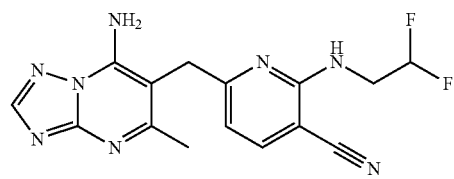 [SMILES: Cc1nc2ncnn2c(N)c1Cc1ccc(C#N)c(NCC(F)F)n1]

A mixture of 6-({7-amino-5-methyl-[1,2,4]triazolo[1,5-a]pyrimidin-6-yl}methyl)-2-chloropyridine-3-carbonitrile (35 mg; 0.12 mmol), 2,2-difluoroethan-1-amine (142 mg; 1.75 mmol), N,N-diisopropylethylamine (202 µL; 1.17 mmol), potassium fluoride (34 mg; 0.58 mmol) in 3 mL 1-methylpiperazine is stirred for 1 hour at 150° C. The reaction is quenched with methanol, filtered and purified by reverse phase chromatography-HPLC (modifier: ammonium hydroxide).

Yield: 13 mg (32% of theory)
Mass spectrometry (ESI+): m/z=345 [M+H]+
HPLC (Method 1): Retention time=0.731 min.

Following examples are prepared analogously to example 7.1:

| Example | Structure | Mass spectrometry | HPLC Retention time | Starting material Step A | Starting material Step D |
|---|---|---|---|---|---|
| 7.2 | 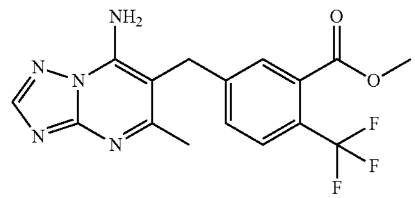 [SMILES: COC(=O)c1cc(Cc2c(C)nc3ncnn3c2N)ccc1C(F)(F)F] | (ESI+): m/z = 366 [M + H]+ | (Method 1): 1.080 min | methyl 5-methyl-2-(trifluoro-methyl)-benzoate | No Step D |
| 7.3 | 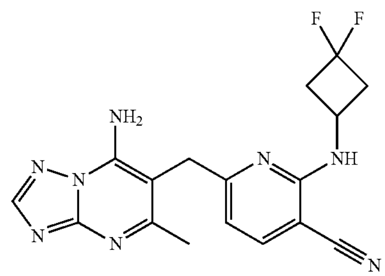 [SMILES: Cc1nc2ncnn2c(N)c1Cc1ccc(C#N)c(NC2CC(F)(F)C2)n1] | (ESI+): m/z = 371 [M + H]+ | (Method 1): 0.832 min | 2-chloro-6-methyl-pyridine-3-carbo-nitrile | 3,3-difluoro-cyclo-butan-1-amine hydro-chloride |
| 7.4 | 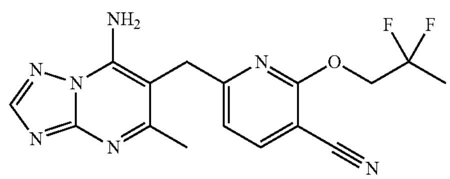 [SMILES: Cc1nc2ncnn2c(N)c1Cc1ccc(C#N)c(OCC(C)(F)F)n1] | (ESI+): m/z = 360 [M + H]+ | (Method 1): 0.814 min | 2-(2,2-di-fluoro-propoxy)-6-methyl-pyridine-3-carbo-nitrile (Inter-mediate 7.4.A) | No Step D |
| 7.5 | 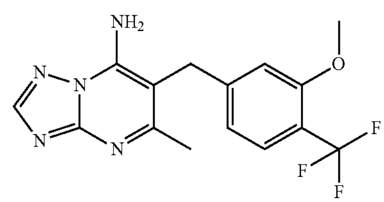 [SMILES: COc1cc(Cc2c(C)nc3ncnn3c2N)ccc1C(F)(F)F] | (ESI+): m/z = 338 [M + H]+ | (Method 3): 0.881 min | 4-(bromo-methyl)-2-methoxy-1-(tri-fluoro-methyl) benzene | No Step D |
| 7.6 | 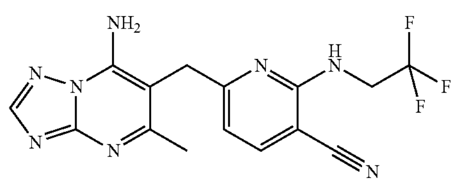 [SMILES: Cc1nc2ncnn2c(N)c1Cc1ccc(C#N)c(NCC(F)(F)F)n1] | (ESI+): m/z = 363 [M + H]+ | (Method 1): 0.761 min | 2-chloro-6-methyl-pyridine-3-carbo-nitrile | 2,2,2-trifluoro-ethan-1-amine |
| 7.7 | 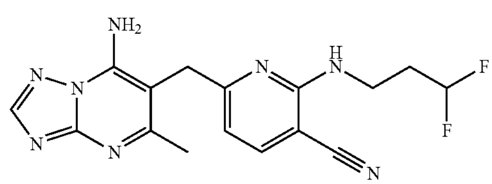 [SMILES: Cc1nc2ncnn2c(N)c1Cc1ccc(C#N)c(NCCC(F)F)n1] | (ESI+): m/z = 359 [M + H]+ | (Method 1): 0.784 min | 2-chloro-6-methyl-pyridine-3-carbo-nitrile | 3,3-difluoro-propan-1-amine hydro-chloride |
| 7.8 | 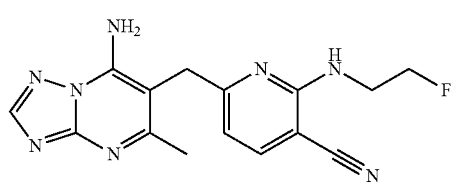 [SMILES: Cc1nc2ncnn2c(N)c1Cc1ccc(C#N)c(NCCF)n1] | (ESI+): m/z = 327 [M + H]+ | (Method 1): 0.723 min | 2-chloro-6-methyl-pyridine-3-carbo-nitrile | 2-fluoro-ethan-1-amine hydro-chloride |

-continued

| Example | Structure | Mass spectrometry | HPLC Retention time | Starting material Step A | Starting material Step D |
|---------|-----------|-------------------|---------------------|--------------------------|--------------------------|
| 7.9 | 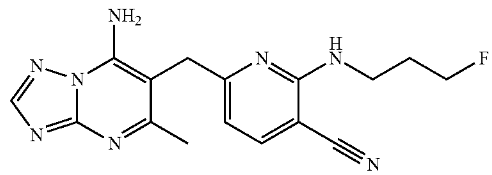 [SMILES: Cc1nc2ncnn2c(N)c1Cc1ccc(C#N)c(NCCCF)n1] | (ESI+): m/z = 341 [M + H]+ | (Method 1): 0.758 min | 2-chloro-6-methyl-pyridine-3-carbo-nitrile | 3-fluoro-propan-1-amine hydro-chloride |
| 7.10 | 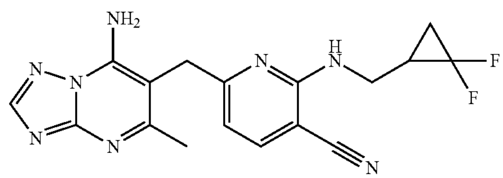 [SMILES: Cc1nc2ncnn2c(N)c1Cc1ccc(C#N)c(NCC2CC2(F)F)n1] | (ESI+): m/z = 371 [M + H]+ | (Method 1): 0.807 min | 2-chloro-6-methyl-pyridine-3-carbo-nitrile | (2,2-difluoro-cyclo-propyl)-methan-amine hydro-chloride |
| 7.11 | 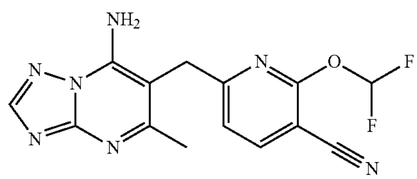 [SMILES: Cc1nc2ncnn2c(N)c1Cc1ccc(C#N)c(OC(F)F)n1] | (ESI+): m/z = 330 [M + H]+ | (Method 1): 0.759 min | 2-(difluoro-methoxy)-6-methyl-pyridine-3-carbo-nitrile (Inter-mediate 7.11.A) | No Step D |

Procedure 8

Step A

3-Bromo-6-(bromomethyl)-2-fluoropyridine

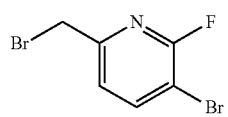

A mixture of 3-bromo-2-fluoro-6-methylpyridine (2.50 g; 12.8 mmol), 1-bromopyrrolidine-2,5-dione (2.73 g; 15.3 mmol), azobisisobutyronitrile (419 mg; 2.55 mmol) in 25 mL of dichloromethane is stirred for 15 minutes at 110° C. in the microwave. The reaction is concentrated under reduced pressure and the residue is purified by silica gel chromatography (eluent: cyclohexene/ethyl acetate 0→20%).

Yield: 2.9 g (59% of theory)

HPLC (Method 3): Retention time=1.006 min.

Step B

2-[(5-Bromo-6-fluoropyridin-2-yl)methyl]-3-oxobu-tanenitrile

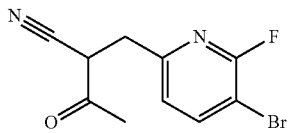

A solution of cyanoacetone sodium salt (CAS: 70807-22-6; 1.20 g; 11.46 mmol) in 6 mL of N,N-dimethylformamide and 180 μL water is cooled to 0° C. and 3-bromo-6-(bromomethyl)-2-fluoropyridine (2.74 g; 7.64 mmol) in 6 mL of N,N-dimethylformamide is added dropwise and the reaction is stirred at room temperature overnight. The reaction is quenched with methanol, filtered and purified by reverse phase chromatography-HPLC (modifier: trifluoro-acetic acid).

Yield: 880 mg (42% of theory)

Mass spectrometry (ESI+): m/z=271/273 [M+H]+ (Br)

HPLC (Method 3): Retention time=0.928 min.

Step C

6-[(5-Bromo-6-fluoro-pyridin-2-yl)methyl]-7-methyl-[1,2,4]triazolo[4,3-a]pyrimidin-5-amine and 6-(5-Bromo-6-fluoro-pyridin-2-ylmethyl)-5-methyl-[1,2,4]triazolo[1,5-a]pyrimidin-7-amine

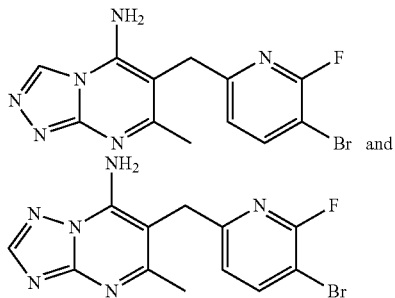

A mixture of 2-[(5-bromo-6-fluoropyridin-2-yl)methyl]-3-oxobutanenitrile (880 mg; 3.25 mmol), 1H-1,2,4-triazol-3-amine (327 mg; 3.90 mmol) and pivalic acid (1.00 g; 9.75 mmol) is stirred at 120° C. for 3 hours. The reaction is quenched with methanol, the precipitate is filtered off, washed with methanol and dried to yield 6-(5-bromo-6-fluoro-pyridin-2-ylmethyl)-5-methyl-[1,2,4]triazolo[1,5-a]pyrimidin-7-amine. The filtrate is concentrated under reduced pressure and purified by reverse phase chromatography (modifier: trifluoroacetic acid) to yield 6-[(5-bromo-6-fluoropyridin-2-yl)methyl]-7-methyl-[1,2,4]triazolo[4,3-a]pyrimidin-5-amine.

6-(5-Bromo-6-fluoro-pyridin-2-ylmethyl)-5-methyl-[1,2,4]triazolo[1,5-a]pyrimidin-7-ylamine Yield: 416 mg (38% of theory)
Mass spectrometry (ESI$^+$): m/z=337/339 [M+H]$^+$ (Br)
HPLC (Method 3): Retention time=0.777 min. 6-[(5-bromo-6-fluoropyridin-2-yl)methyl]-7-methyl-[1,2,4]triazolo[4,3-a]pyrimidin-5-amine Yield: 300 mg (27% of theory)
Mass spectrometry (ESI$^+$): m/z=337/339 [M+H]$^+$ (Br)
HPLC (Method 2): Retention time=0.702 min.

Step D

Example 8.1

6-{[5-Bromo-6-(3-fluoropropoxy)pyridin-2-yl]methyl}-5-methyl-[1,2,4]triazolo[1,5-a]pyrimidin-7-amine

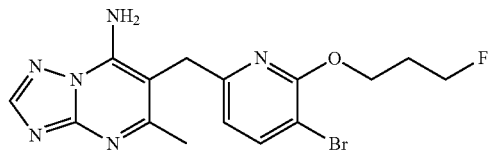 [SMILES: Cc1nc2ncnn2c(N)c1Cc1ccc(Br)c(OCCCF)n1]

A mixture of 6-[(5-bromo-6-fluoropyridin-2-yl)methyl]-7-methyl-[1,2,4]triazolo[4,3-a]pyrimidin-5-amine (50.0 mg; 0.15 mmol), 3-fluoropropan-1-ol (111 μL; 1.48 mmol), cesium carbonate (120 mg; 0.37 mmol) in 2.5 mL dioxane is stirred at 120° C. for a few hours. The reaction is quenched with methanol, filtered and purified by reverse phase chromatography-HPLC (modifier: ammonium hydroxide).

Yield: 11 mg (19% of theory)
Mass spectrometry (ESI$^+$): m/z=395/397 [M+H]$^+$ (Br)
HPLC (Method 1): Retention time=0.884 min.

Following examples are prepared analogously to procedure 8 starting with 6-[(5-bromo fluoropyridin-2-yl)methyl]-7-methyl-[1,2,4]triazolo[4,3-a]pyrimidin-5-amine

| Example | | Mass spectrometry | HPLC Retention time | Starting material Step D |
|---|---|---|---|---|
| 8.2 | (structure) | (ESI$^-$): m/z = 414/416 [M − H]$^-$ (Br) | (Method 1): 0.866 min | 2,2,2-trifluoroethan-1-amine |
| 8.3 | (structure) | (ESI$^-$): m/z = 379/381 [M − H]$^-$ (Br) | (Method 1): 0.847 min | 2-fluoroethan-1-ol |
| 8.4 | (structure) | (ESI$^-$): m/z = 397/399 [M − H]$^-$ (Br) | (Method 1): 0.860 min | 2,2-difluoroethan-1-ol |

Procedure 9

Step A

Example 9.1

6-({7-Amino-5-methyl-[1,2,4]triazolo[1,5-a]pyrimidin-6-yl}methyl)-2-(2,2-difluoroethoxy)pyridine-3-carbonitrile

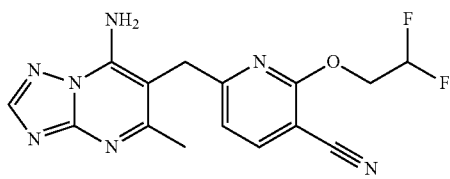 [SMILES: Cc1nc2ncnn2c(N)c1Cc1ccc(C#N)c(OCC(F)F)n1]

A mixture of 6-({7-amino-5-methyl-[1,2,4]triazolo[1,5-a]pyrimidin-6-yl}methyl)-2-chloropyridine-3-carbonitrile (67 mg; 0.22 mmol) (see procedure 7, step C), 2,2-difluoroethan-1-ol (183 mg; 2.24 mmol), cesium carbonate (182 mg; 0.56 mmol) in 3 mL of dioxane is stirred for 1 hour at 100° C. The reaction is quenched with methanol, filtered and purified by reverse phase chromatography-HPLC (modifier: ammonium hydroxide).

Yield: 40 mg (52% of theory)
Mass spectrometry (ESI$^+$): m/z=346 [M+H]$^+$
HPLC (Method 1): Retention time=0.760 min.

Following examples are prepared analogously to procedure 9 starting with 6-({7-amino methyl-[1,2,4]triazolo[1,5-a]pyrimidin-6-yl}methyl)-2-chloropyridine-3-carbonitrile

| Example | Structure | Mass spectrometry | HPLC Retention time | Starting material Step D |
|---|---|---|---|---|
| 9.2 | 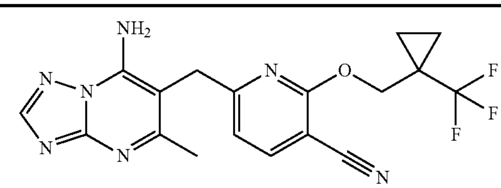 | (ESI$^+$): m/z = 404 [M + H]$^+$ | (Method 1): 0.866 min | [1-(trifluoromethyl)cyclopropyl]methanol |
| 9.3 | 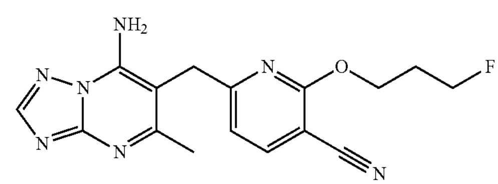 [SMILES: Cc1nc2ncnn2c(N)c1Cc1ccc(C#N)c(OCCCF)n1] | (ESI$^+$): m/z = 342 [M + H]$^+$ | (Method 1): 0.766 min | 3-fluoropropan-1-ol |
| 9.4 | 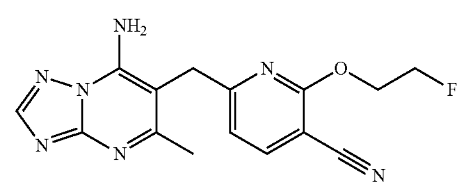 [SMILES: Cc1nc2ncnn2c(N)c1Cc1ccc(C#N)c(OCCF)n1] | (ESI$^+$): m/z = 328 [M + H]$^+$ | (Method 1): 0.735 min | 2-fluoroethan-1-ol |
| 9.5 | 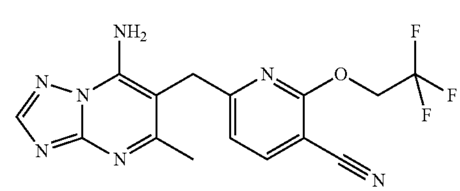 [SMILES: Cc1nc2ncnn2c(N)c1Cc1ccc(C#N)c(OCC(F)(F)F)n1] | (ESI$^+$): m/z = 364 [M + H]$^+$ | (Method 1): 0.806 min | 2,2,2-trifluoroethan-1-ol |

Procedure 10

Step A

6-[(5-Bromo-6-fluoropyridin-2-yl)methyl]-5-methyl-[1,2,4]triazolo[1,5-a]pyrimidin-7-amine

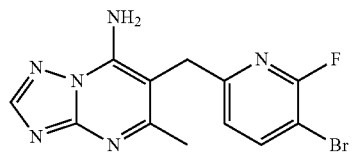 [SMILES: Cc1nc2ncnn2c(N)c1Cc1ccc(Br)c(F)n1]

A mixture of 2-[(5-bromo-6-fluoropyridin-2-yl)methyl]-3-oxobutanenitrile (840 g; 3.10 mmol) (see procedure 8, step B), 1H-1,2,4-triazol-3-amine (312.6 mg; 3.72 mmol) and pivalic acid (1 g; 9.92 mmol) are stirred at 120° C. for 3 hours. The reaction is quenched with methanol and the precipitate is filtered off, washed with methanol and dried.

Yield: 481 mg (46% of theory)
Mass spectrometry (ESI⁺): m/z=337/339 [M+H]⁺ (Br)
HPLC (Method 3): Retention time=0.780 min.

Step B

Example 10.1

6-{[5-Bromo-6-(4-fluoro-1H-pyrazol-1-yl)pyridin-2-yl]methyl}-5-methyl-[1,2,4]triazolo[1,5-a]pyrimidin-7-amine

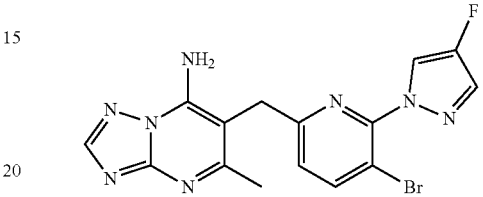

To 4-fluoro-1H-pyrazole (15.3 mg; 0.18 mmol) in 3 mL of N,N-dimethylformamide is added potassium carbonate (24.6 mg; 0.18 mmol) and the mixture is stirred for 15 minutes at room temperature. 6-[(5-Bromo-6-fluoropyridin-2-yl)methyl]-5-methyl-[1,2,4]triazolo[1,5-a]pyrimidin-7-amine (30 mg; 89.0 μmol) is added and the reaction is stirred for 90 minutes at 70° C. and for 1 hour at 100° C. The reaction is quenched with methanol, filtered and purified by reverse phase chromatography-HPLC (modifier: ammonium hydroxide).

Yield: 21 mg (59% of theory)
Mass spectrometry (ESI⁺): m/z=403, 405 [M+H]⁺ (Br)
HPLC (Method 1): Retention time=0.803 min.

Following examples are prepared analogously to procedure 10 starting with 3-bromo-2-fluoro-6-methylpyridine and the appropriate pyrazole derivative:

| Example | Structure | Mass spectrometry | HPLC Retention time |
| --- | --- | --- | --- |
| 10.2 | ![structure] | (ESI⁻): m/z = 451/453 [M − H]⁻ (Br) | (Method 1): 0.911 min |
| 10.3 | ![structure] | (ESI⁻): m/z = 451/453 [M − H]⁻ (Br) | (Method 1): 0.914 min |

Procedure 11

Example 11.1

{[5-({7-Amino-5-methyl-[1,2,4]triazolo[1,5-a]pyrimidin-6-yl}methyl)-2-(trifluoromethoxy)phenyl]imino}dimethyl-λ6-sulfanone

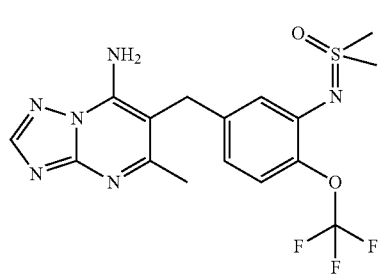 [SMILES: Cc1nc2ncnn2c(N)c1Cc1ccc(OC(F)(F)F)c(N=S(C)(C)=O)c1]

The reaction is carried out under an argon atmosphere. To a mixture of 6-{[3-bromo-4-(trifluoromethoxy)phenyl]methyl}-5-methyl-[1,2,4]triazolo[1,5-a]pyrimidin-7-amine (280 mg; 0.70 mmol) (see procedure 4, example 4.4), iminodimethyl-lambda6-sulfanone (97.3 mg; 1.04 mmol), {[1,1'-biphenyl]-2-yl}di-tert-butyl)phosphane (41.5 mg; 0.14 mmol) and sodium-tert-butylate (100 mg; 1.04 mmol) in 1 mL N,N-dimethylformamide is added tris((1E,4E)-1,5-diphenylpenta-1,4-dien-3-one) dipalladium (51.0 mg; 55.7 µmol) and the reaction mixture is stirred at 90° C. for 1 hour. The reaction is quenched with acetonitrile/water, filtered and purified by reverse phase chromatography-HPLC (modifier: ammonium hydroxide).

Yield: 22 mg (8% of theory)
Mass spectrometry (ESI⁺): m/z=415 [M+H]⁺
HPLC (Method 1): Retention time=0.768 min.

Following example is prepared analogously to procedure 11 starting with 6-{[3-bromo (trifluoromethoxy)phenyl]methyl}-5-methyl-[1,2,4]triazolo[1,5-a]pyrimidin-7-amine and 1-imino-1λ6-thietan-1-one (prepared according to WO 2008/141843

Procedure 12

Example 12.1

6-({7-Amino-5-methyl-[1,2,4]triazolo[1,5-a]pyrimidin-6-yl}methyl)-3-(difluoromethoxy)pyridine-2-carbonitrile

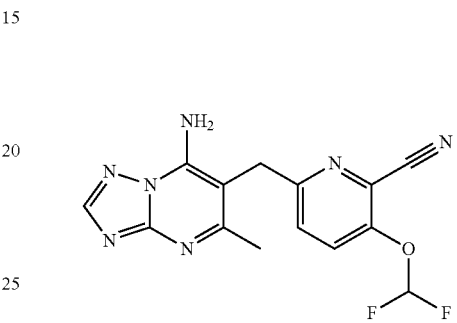

The reaction is carried out under an argon atmosphere. To a solution of 6-{[6-bromo-5-(difluoromethoxy)pyridin-2-yl]methyl}-5-methyl-[1,2,4]triazolo[1,5-a]pyrimidin-7-amine (155 mg; 0.32 mmol) (see procedure 4, example 4.1) in 5 mL of N,N-dimethylformamide is added 1,1'-bis(diphenylphosphino)ferrocene (17.9 mg; 32.3 µmol) and zinc cyanide (56.7 mg; 0.48 mmol). After stirring for a few minutes, tris(dibenzylideneacetone)dipalladium(0) (14.8 mg; 16.2 µmol) is added and the reaction is stirred for 30 min at 120° C. The reaction is purified by reverse phase chromatography (modifier: ammonium hydroxide).

Yield: 43 mg (40% of theory)
Mass spectrometry (ESI⁺): m/z=332 [M+H]⁺
HPLC (Method 1): Retention time=0.753 min.

| Example | Structure | Mass spectrometry | HPLC Retention time |
|---|---|---|---|
| 11.2 | (structure shown) | (ESI⁺): m/z = 427 [M + H]⁺ | (Method 7): 0.787 min |

Procedure 13

Step A

2-Bromo-6-(bromomethyl)pyridine

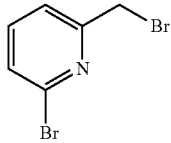

To a solution of (6-bromo-pyridin-2-yl)-methanol (2.00 g; 10.64 mmol) in 15 mL of dichloromethane is added dropwise phosphorus tribromide (0.61 mL; 6.44 mmol) at 0° C. The mixture is warmed to room temperature and stirred overnight. Additional 100 μL of phosphorus tribromide is added and the reaction mixture is stirred for 3 hours at room temperature. The reaction is quenched with cooled NaHCO₃ (half saturated aqueous solution) and extracted two times with dichloromethane. The combined organic layers are dried and concentrated under reduced pressure.

Yield: 2.44 g (91% of theory)

Mass spectrometry (ESI⁺): m/z=250/252 [M+H]⁺ (Br)

HPLC (Method 1): Retention time=0.878 min.

Step B

2-[(6-Bromopyridin-2-yl)methyl]-3-oxobutanenitrile

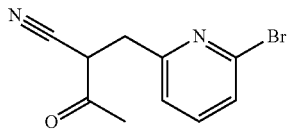

A solution of cyanoacetone sodium salt (CAS: 70807-22-6; 1.53 g; 14.6 mmol) in 8 mL of N,N-dimethylformamide and 240 μL of water is cooled to 0° C. and 2-bromo-6-(bromomethyl)pyridine (2.44 g; 9.72 mmol) in 8 mL of N,N-dimethylformamide is added dropwise and the reaction is stirred at room temperature overnight. The reaction is concentrated under reduced pressure to provide a crude product, which is used directly in the next step.

Yield: 0.89 g (36% of theory)

Mass spectrometry (ESI⁺): m/z=253/255 [M+H]⁺ (Br)

HPLC (Method 3): Retention time=0.87 min.

Step C

6-[(6-Bromopyridin-2-yl)methyl]-5-methyl-[1,2,4]triazolo[1,5-a]pyrimidin-7-amine

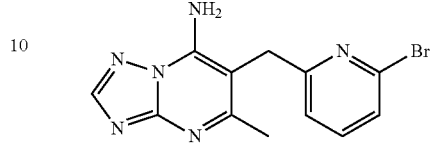

A mixture of 2-[(6-bromopyridin-2-yl)methyl]-3-oxobutanenitrile (0.89 g; 3.52 mmol), triazol-3-amine (295 mg; 3.52 mmol) and pivalic acid (1.00 g; 9.79 mmol) is stirred at 120° C. for 4 hours. The reaction is quenched with methanol and the precipitate is filtered off, washed with methanol and dried.

Yield: 780 mg (69% of theory)

Mass spectrometry (ESI⁺): m/z=319/321 [M+H]⁺ (Br)

HPLC (Method 1): Retention time=0.748 min.

Step D

Example 13.1

5-Methyl-6-({6-[1-methyl-3-(trifluoromethyl)-1H-pyrazol-4-yl]pyridin-2-yl}methyl)-[1,2,4]triazolo[1,5-a]pyrimidin-7-amine

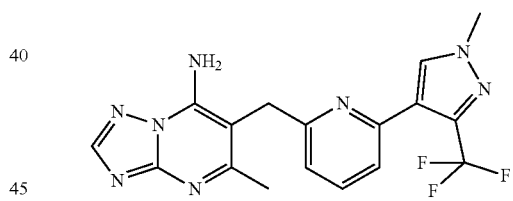

The reaction is carried out under an argon atmosphere. To a mixture of 6-[(6-bromopyridin-2-yl)methyl]-5-methyl-[1,2,4]triazolo[1,5-a]pyrimidin-7-amine (50.0 mg; 0.16 mmol), [1-methyl-3-(trifluoromethyl)-1H-pyrazol-4-yl]boronic acid (51.6 mg; 0.27 mmol), potassium carbonate (2M aqueous solution) (200 μL; 0.40 mmol) in 2 mL of dioxane is added 1,1'-bis(di-tert-butylphosphino)ferrocene palladium dichloride (30.6 mg; 47.0 μmol) and the reaction mixture is stirred for 1 hour at 100° C. The reaction is quenched with methanol, filtered and purified by reverse phase chromatography-HPLC (modifier: ammonium hydroxide).

Yield: 28 mg (46% of theory)

Mass spectrometry (ESI⁺): m/z=389 [M+H]⁺

HPLC (Method 1): Retention time=0.849 min.

Following example is prepared analogously to example 13.1 starting with 6-[(6-bromopyridin-2-yl)methyl]-5-methyl-[1,2,4]triazolo[1,5-a]pyrimidin-7-amine and 4-(4,4,5,5-tetramethyl-1,3,2-dioxaborolan-2-yl)-3-(trifluoromethyl)-1H-pyrazole:

| Example | Structure | Mass spectrometry | HPLC Retention time |
|---|---|---|---|
| 13.2 | 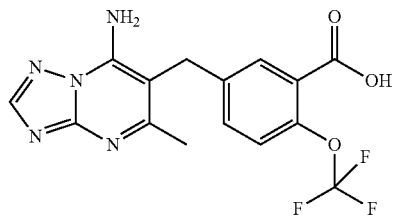 | (ESI+): m/z = 375 [M + H]+ | (Method 1): 0.766 min |

Procedure 14

Example 14.1

1-[6-({7-Amino-5-methyl-[1,2,4]triazolo[1,5-a]pyrimidin-6-yl}methyl)-3-bromopyridin-2-yl]-3,3-difluorocyclobutane-1-carbonitrile

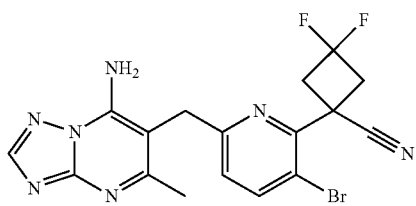 [SMILES: Cc1nc2ncnn2c(N)c1Cc1ccc(Br)c(C2(C#N)CC(F)(F)C2)n1]

To a solution of 6-[(5-bromo-6-chloropyridin-2-yl)methyl]-5-methyl-[1,2,4]triazolo[1,5-a]pyrimidin-7-amine (50.0 mg; 0.14 mmol) (see procedure 1, step F), 3,3-difluorocyclobutane-1-carbonitrile (76 μL; 0.49 mmol) in 3 mL tetrahydrofuran is added dropwise sodium bis(trimethylsilyl)amide (1M solution in tetrahydrofuran) (495 μL; 0.49 mmol) and the reaction is stirred for a few minutes at room temperature. After stirring at 100° C. for 10 minutes, the reaction is quenched with NaHCO₃ (saturated aqueous solution) and extracted two times with ethyl acetate. The combined organic layers are dried and concentrated under reduced pressure. The residue is purified by reverse phase chromatography (modifier: ammonium hydroxide).

Yield: 9 mg (15% of theory)
Mass spectrometry (ESI+): m/z=434, 436 [M+H]+ (Br)
HPLC (Method 1): Retention time=0.849 min.

Procedure 15

Step A

Example 15.1

Methyl 5-({7-amino-5-methyl-[1,2,4]triazolo[1,5-a]pyrimidin-6-yl}methyl)-2-(trifluoromethoxy)benzoate

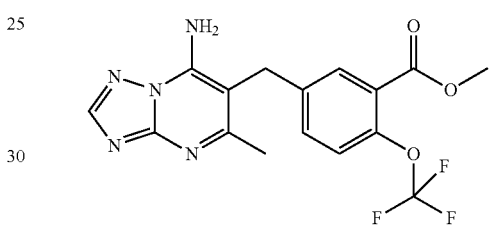

To a solution of 6-{[3-bromo-4-(trifluoromethoxy)phenyl]methyl}-5-methyl-[1,2,4]triazolo[1,5-a]pyrimidin-7-amine (100 mg; 0.25 mmol) (see procedure 4, example 4.4) in 4 mL of methanol and 1 mL of N,N-dimethylformamide is added triethylamine (70.0 μL; 0.505 mmol) and 1,1'-bis(diphenylphosphino)ferrocene dichloromethane (40.0 mg; 49.0 μmol). The reaction is stirred under a CO atmosphere at 5 bar and 80° C. overnight. The reaction is filtered and concentrated under reduced pressure. The residue is purified by reverse phase chromatography (modifier: trifluoroacetic acid).

Yield: 11 mg (12% of theory)
Mass spectrometry (ESI+): m/z=382 [M+H]+
HPLC (Method 3): Retention time=0.885 min

Step B 5-({7-Amino-5-methyl-[1,2,4]triazolo[1,5-a]pyrimidin-6-yl}methyl)-2-(trifluoromethoxy)benzoic acid To methyl 5-({7-amino-5-methyl-[1,2,4]triazolo[1,5-a]pyrimidin-6-yl}methyl) (trifluoromethoxy)benzoate (115 mg; 0.30 mmol) in 2 mL of tetrahydrofuran is added lithium hydroxide (2M aqueous solution) (377 µL; 0.75 mmol) and the reaction is stirred for 2 hours at room temperature. The reaction is concentrated under reduced pressure. The residue is dissolved in water and acidified with HCl (4M aqueous solution) at pH 6. The precipitate is filtered off and dried.

Yield: 60 mg (54% of theory)
Mass spectrometry (ESI+): m/z=368 [M+H]+
HPLC (Method 3): Retention time=0.779 min Step C Example 15.2

5-({7-Amino-5-methyl-[1,2,4]triazolo[1,5-a]pyrimidin-6-yl}methyl)-N,N-dimethyl-2-(trifluoromethoxy)benzamide

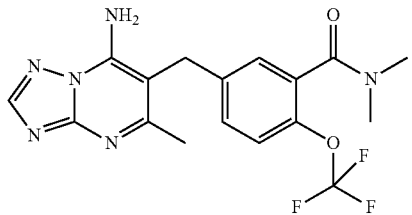 [SMILES: Cc1nc2ncnn2c(N)c1Cc1ccc(OC(F)(F)F)c(C(=O)N(C)C)c1]

To a solution of 5-({7-amino-5-methyl-[1,2,4]triazolo[1,5-a]pyrimidin-6-yl}methyl)-2-(trifluoromethoxy)benzoic acid (20.0 mg; 54.4 µmol) in 1 mL of N,N-dimethylformamide is added (1-[bis(dimethylamino)methylene]-1H-1,2,3-triazolo[4,5-b]pyridinium 3-oxid hexafluorophosphate, HATU) (22.7 mg; 59.9 µmol) and N,N-diisopropylethylamine (22.1 µL; 0.12 mmol) and the reaction is stirred for 15 minutes at room temperature. Dimethylamine (2M in tetrahydrofuran) (29.9 µL; 59.9 µmol) is added and the reaction is stirred overnight at room temperature. The reaction is diluted with water/acetonitrile, filtered and purified by reverse phase chromatography (modifier: ammonium hydroxide).

Yield: 12 mg (56% of theory)
Mass spectrometry (ESI+): m/z=395 [M+H]+
HPLC (Method 3): Retention time=0.790 min Following examples are prepared analogously to example 15.2 starting with 5-({7-Amino methyl-[1,2,4]triazolo[1,5-a]pyrimidin-6-yl}methyl)-2-(trifluoromethoxy)benzoic acid and an appropriate amine:

| Example | Structure | Mass spectrometry | HPLC Retention time |
|---|---|---|---|
| 15.3 | | (ESI+): m/z = 409 [M + H]+ | (Method 5): 0.56 min |
| 15.4 | | (ESI+): m/z = 367 [M + H]+ | (Method 3): 0.688 min |
| 15.5 | | (ESI+): m/z = 381 [M + H]+ | (Method 5): 0.45 min |

Procedure 16

Step A 6-({7-Amino-5-methyl-[1,2,4]triazolo[1,5-a]pyrimidin-6-yl}methyl)-3-bromopyridin-2-amine

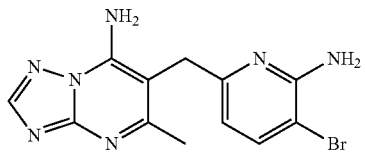 [SMILES: Cc1nc2ncnn2c(N)c1Cc1ccc(Br)c(N)n1]

A mixture of 6-[(5-bromo-6-chloropyridin-2-yl)methyl]-5-methyl-[1,2,4]triazolo[1,5-a]pyrimidin-7-amine (700 mg; 1.98 mmol) (see procedure 1, step F), (2,4-dimethoxyphenyl)methanamine (1.19 mL; 7.91 mmol) and N,N-diisopropylethylamine (1.03 mL; 5.94 mmol) in 8 mL of dimethyl sulfoxide is stirred for a few hours at 125° C. The reaction is quenched with methanol, filtered and purified by reverse phase chromatography (modifier: trifluoroacetic acid).

The product is dissolved in dichloromethane and 0.5 mL trifluoroacetic acid is added and the mixture is stirred for 2 hours at room temperature. The mixture is concentrated, the residue is dissolved in methanol and tetraalkylammonium carbonate, polymer-bound is added. After stirring for 2 h, the mixture is filtered and the filtrate is concentrated under reduced pressure. The residue is treated with methanol and the precipitate is filtered off and dried.

Yield: 50 mg (8% of theory)
Mass spectrometry (ESI$^+$): m/z=334, 336 [M+H]$^+$ (Br)
HPLC (Method 3): Retention time=0.646 min Step B Example 16.1

6-({7-Amino-5-methyl-[1,2,4]triazolo[1,5-a]pyrimidin-6-yl}methyl)-3-[3-(trifluoromethyl)-1H-pyrazol-4-yl]pyridin-2-amine

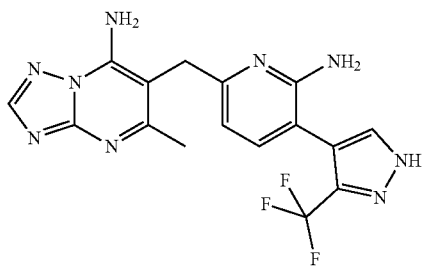 [SMILES: Cc1nc2ncnn2c(N)c1Cc1ccc(-c2c[nH]nc2C(F)(F)F)c(N)n1]

The reaction is carried out under an argon atmosphere. To a mixture of 6-({7-amino-5-methyl-[1,2,4]triazolo[1,5-a]pyrimidin-6-yl}methyl)-3-bromopyridin-2-amine (50.0 mg; 0.15 mmol), 4-(4,4,5,5-tetramethyl-1,3,2-dioxaborolan-2-yl)-3-(trifluoromethyl)-1H-pyrazole (66.6 mg; 0.25 mmol), potassium carbonate (2M aqueous solution) (200 µL; 0.40 mmol) in 2 mL of dioxane is added 1,1'-bis(di-tert-butylphosphino)ferrocene palladium dichloride (29.2 mg; 44.9 µmol) and the reaction is stirred for 1 hour at 120° C. The reaction is quenched with methanol, filtered and purified by reverse phase chromatography-HPLC (modifier: ammonium hydroxide)

Yield: 7 mg (12% of theory)
Mass spectrometry (ESI$^+$): m/z=390 [M+H]$^+$
HPLC (Method 1): Retention time=0.716 min.

Procedure 17

Step A 4,4-Difluoro-3-oxo-2-{[4-(trifluoromethyl)phenyl]methyl}butanenitrile

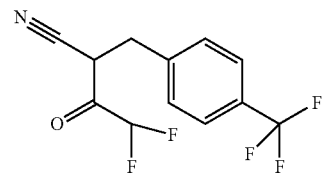 [SMILES: N#CC(Cc1ccc(C(F)(F)F)cc1)C(=O)C(F)F]

To a solution of 4-(trifluoromethyl)benzaldehyde (250 mg; 1.44 mmol) in 5 mL of ethanol is added sodium (1E)-1-cyano-3,3-difluoroprop-1-en-2-olate (200 mg; 1.42 mmol), 3,5-diethyl 2,6-dimethyl-1,4-dihydropyridine-3,5-dicarboxylate (360 mg; 1.42 mmol) and pyrrolidine-2-carboxylic acid (16 mg; 0.14 mmol). The reaction is stirred for 7 days at room temperature. The reaction mixture is concentrated under reduced pressure. The residue is diluted in ethyl acetate and extracted three times with HCl (1M aqueous solution). The organic layer is dried and concentrated under reduced pressure.

Yield: 617 mg (86% of theory)
Mass spectrometry (ESI$^+$): m/z=276 [M–H]$^-$
HPLC (Method 1): Retention time=0.65 min.

Step B

Example 17.1

5-(Difluoromethyl)-6-{[4-(trifluoromethyl)phenyl]methyl}-[1,2,4]triazolo[1,5-a]pyrimidin-7-amine

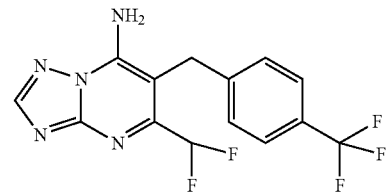 [SMILES: Nc1c(Cc2ccc(C(F)(F)F)cc2)c(C(F)F)nc2ncnn12]

A mixture of 4,4-difluoro-3-oxo-2-{[4-(trifluoromethyl)phenyl]methyl}butanenitrile (610 mg; 1.10 mmol), 1H-1,2,4-triazol-3-amine (280 mg; 3.33 mmol) and pivalic acid (1.00 g; 9.79 mmol) are stirred at 140° C. for 4 hours. The reaction is quenched with methanol and purified by reverse phase chromatography-HPLC (modifier: trifluoroacetic acid).

Yield: 49 mg (13% of theory)
Mass spectrometry (ESI$^+$): m/z=344 [M+H]$^+$
HPLC (Method 6): Retention time=0.77 min.

Following example is prepared analogously to procedure 17 starting from cyanoacetone sodium salt and 2-bromo-4-(trifluoromethyl)benzaldehyde:

| Example | Structure | Mass spectrometry | HPLC Retention time |
|---|---|---|---|
| 17.2 | 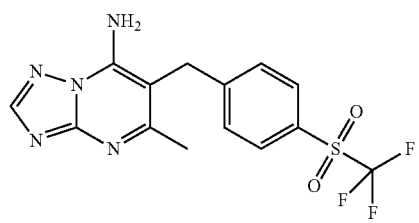 | (ESI⁻): m/z = 384/386 [M − H]⁻ (Br) | (Method 1): 0.95 min |

Procedure 18

Example 18.1

5-Methyl-6-[(4-trifluoromethanesulfonylphenyl)methyl]-[1,2,4]triazolo[1,5-a]pyrimidin-7-amine To a solution of 5-methyl-6-({4-[(trifluoromethyl)sulfanyl]phenyl}methyl)-[1,2,4]triazolo[1,5-a]pyrimidin-7-amine (550 mg; 1.62 mmol) (see procedure 6, example 6.5) in 15 mL of acetic acid is added dropwise a solution of potassium permanganate (380 mg; 2.40 mmol) in 10 mL of water. The reaction is stirred overnight at room temperature. The reaction is diluted with water and extracted three times with ethyl acetate. The combined organic layers are dried over magnesium sulfate, filtered and concentrated under reduced pressure.

Yield: 139 mg (23% of theory)
Mass spectrometry (ESI⁺): m/z=372 [M+H]⁺
HPLC (Method 2): Retention time=0.83 min.

Procedure 19

Step A

Example 19.1

5-Methyl-6-[(4-trifluoromethanesulfinylphenyl)methyl]-[1,2,4]triazolo[1,5-a]pyrimidin-7-amine

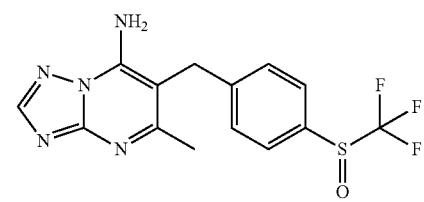 [SMILES: Cc1nc2ncnn2c(N)c1Cc1ccc(S(=O)C(F)(F)F)cc1]

To a suspension of 5-methyl-6-({4-[(trifluoromethyl)sulfanyl]phenyl}methyl)-[1,2,4]triazolo[1,5-a]pyrimidin-7-amine (2.00 g; 5.89 mmol) (see procedure 6, example 6.5) in 150 mL of dichloromethane is added 3-chlorobenzene-1-carboperoxoic acid (75%; 3.66 g; 15.9 mmol) and the reaction is stirred overnight at room temperature. 3-chlorobenzene-1-carboperoxoic acid (75%; 677 mg; 2.95 mmol) is added and the reaction is stirred for 3 hours. The reaction is concentrated under reduced pressure and the residue is purified by silica gel chromatography (eluent: dichloromethane/methanol 3%→7%). The crude product is purified by reverse phase chromatography-HPLC (modifier: trifluoroacetic acid).

Yield: 315 mg (15% of theory)
Mass spectrometry (ESI⁺): m/z=356 [M+H]⁺
HPLC (Method 1): Retention time=0.767 min.

Procedure 20

Step A

Example 20.1

5-({7-Amino-5-methyl-[1,2,4]triazolo[1,5-a]pyrimidin-6-yl}methyl)-2-(trifluoromethoxy)benzonitrile

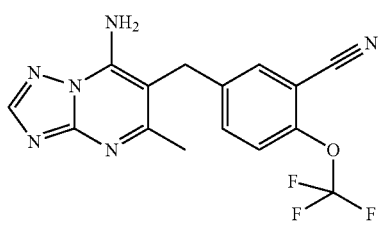 [SMILES: Cc1nc2ncnn2c(N)c1Cc1ccc(OC(F)(F)F)c(C#N)c1]

The reaction is carried out under an argon atmosphere. To a solution of 6-{[3-bromo (trifluoromethoxy)phenyl]methyl}-5-methyl-[1,2,4]triazolo[1,5-a]pyrimidin-7-amine (60 mg; 0.15 mmol) (see procedure 4, example 4.4) in 1 mL of N,N-dimethylformamide is added zinc cyanide (43.8 mg; 0.37 mmol) and tetrakis(triphenylphosphane) palladium (103.4 mg; 89.4 mmol). After stirring for 1 hour at 110° C., the reaction is quenched with water/acetonitrile, filtered and purified by reverse phase chromatography-HPLC (modifier: trifluoroacetic acid). The residue is basified and purified again by reverse phase chromatography-HPLC (modifier: ammonium hydroxide).

Yield: 3 mg (6% of theory)
Mass spectrometry (ESI$^+$): m/z=349 [M+H]$^+$
HPLC (Method 3): Retention time=0.865 min.

Procedure 21

Step A

2-{[2-Fluoro-4-(trifluoromethyl)phenyl]methyl}-3-oxobutanenitrile

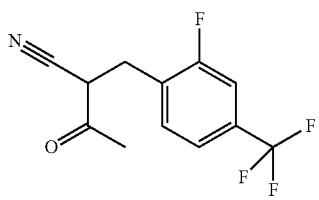 [SMILES: CC(=O)C(C#N)Cc1ccc(C(F)(F)F)cc1F]

A solution of cyanoacetone sodium salt (CAS: 70807-22-6; 0.98 g; 9.34 mmol) in 10 mL of N,N-dimethylformamide and 300 µL water are cooled to 0° C. and 1-(bromomethyl)-2-fluoro-4-(trifluoromethyl)benzene (2 g; 7.78 mmol) in 10 mL of N,N-dimethylformamide is added dropwise and the reaction is stirred for 18 hours at room temperature. The reaction mixture is purified by reverse phase chromatography-HPLC (modifier: trifluoroacetic acid).

Yield: 750 mg (37% of theory)
Mass spectrometry (ESI$^+$): m/z=260 [M+H]$^+$
HPLC (Method 3): Retention time=1.022 min.

Step B

6-{[2-Fluoro-4-(trifluoromethyl)phenyl]methyl}-5-methyl-[1,2,4]triazolo[1,5-a]pyrimidin-7-amine

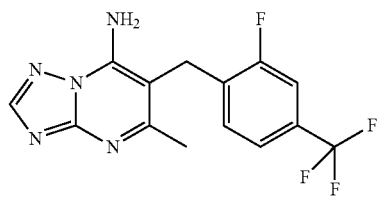 [SMILES: Cc1nc2ncnn2c(N)c1Cc1ccc(C(F)(F)F)cc1F]

A mixture of 2-{[2-fluoro-4-(trifluoromethyl)phenyl]methyl}-3-oxobutanenitrile (350 mg; 1.35 mmol), 1H-1,2,4-triazol-3-amine (170 mg; 2.03 mmol) and pivalic acid (400 mg; 3.92 mmol) are stirred at 140° C. for 1 hours. The reaction is quenched with N,N-dimethylformamide and the precipitate is filtered off and dried.

Yield: 250 mg (57% of theory)
Mass spectrometry (ESI$^+$): m/z=326 [M+H]$^+$
HPLC (Method 3): Retention time=0.908 min.

Procedure 22

Step A

Methyl 5-(2-acetyl-2-cyanoethyl)-2-bromobenzoate

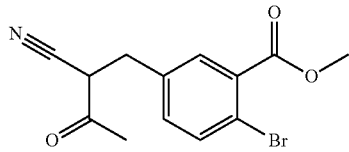 [SMILES: COC(=O)c1cc(CC(C#N)C(C)=O)ccc1Br]

A solution of cyanoacetone sodium salt (CAS: 70807-22-6; 1.02 g; 9.74 mmol) in 20 mL N,N-dimethylformamide and 450 µL of water is cooled to 0° C. and methyl 2-bromo-5-(bromomethyl)benzoate (2 g; 6.49 mmol) in 10 mL of N,N-dimethylformamide is added dropwise and the reaction is stirred for 18 hours at room temperature. The reaction is purified by reverse phase chromatography-HPLC (modifier: trifluoroacetic acid).

Yield: 525 mg (26% of theory)
Mass spectrometry (ESI$^+$): m/z=310 [M+H]$^+$
HPLC (Method 3): Retention time=0.960 min.

Step B

Methyl 5-({7-amino-5-methyl-[1,2,4]triazolo[1,5-a]pyrimidin-6-yl}methyl)-2-bromobenzoate

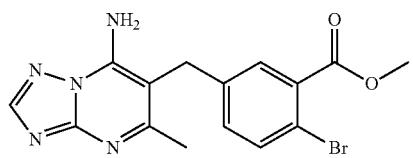 [SMILES: COC(=O)c1cc(Cc2c(C)nc3ncnn3c2N)ccc1Br]

A mixture of methyl 5-(2-acetyl-2-cyanoethyl)-2-bromobenzoate (525 mg; 1.69 mmol), 1H-1,2,4-triazol-3-amine (156 mg; 1.86 mmol) and pivalic acid (500 mg; 4.90 mmol) is stirred at 140° C. for 3 hours. The reaction is quenched with methanol and the precipitate is filtered off, washed with methanol and dried.
Yield: 314 mg (49% of theory)
Mass spectrometry (ESI⁺): m/z=376, 378 [M+H]⁺ (Br)
HPLC (Method 1): Retention time=0.800 min.

Step C 5-({7-Amino-5-methyl-[1,2,4]triazolo[1,5-a]pyrimidin-6-yl}methyl)-2-bromobenzoic acid

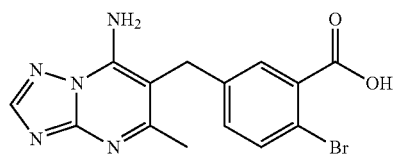 [SMILES: Cc1nc2ncnn2c(N)c1Cc1ccc(Br)c(C(=O)O)c1]

To a mixture of methyl 5-({7-amino-5-methyl-[1,2,4]triazolo[1,5-a]pyrimidin-6-yl}methyl)-2-bromobenzoate (310 mg; 0.82 mmol) in 3 mL of tetrahydrofuran is added lithium hydroxide (2M aqueous solution) (1.24 mL; 2.47 mmol) and 3 mL of water. After stirring for 15 minutes at 100° C., the reaction is acidified with HCl (4M aqueous solution) and stirred for 30 minutes. The precipitate is filtered off and dried.
Yield: 280 mg (94% of theory)
Mass spectrometry (ESI⁺): m/z=362, 364 [M+H]⁺ (Br)
HPLC (Method 3): Retention time=0.707 min Step D Example 22.1

2,2,2-Trifluoroethyl 5-({7-amino-5-methyl-[1,2,4]triazolo[1,5-a]pyrimidin-6-yl}methyl)-2-bromobenzoate

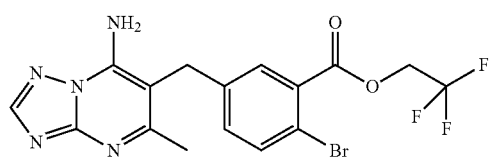 [SMILES: Cc1nc2ncnn2c(N)c1Cc1ccc(Br)c(C(=O)OCC(F)(F)F)c1]

5-({7-Amino-5-methyl-[1,2,4]triazolo[1,5-a]pyrimidin-6-yl}methyl)-2-bromobenzoic acid (50 mg; 0.14 mmol) and thionyl chloride (500 µL; 6.89 mmol) are stirred at 80° C. for 1 hour. 2,2,2-trifluoroethan-1-ol (500 µL; 6.95 mmol) is added and the reaction is stirred for 3 hours at room temperature and overnight at 50° C. The reaction is quenched with water and extracted two times with dichloromethane. The combined organic layers are dried and concentrated under reduced pressure. The residue is purified by reverse phase chromatography (modifier: trifluoroacetic acid).
Yield: 4 mg (7% of theory)
Mass spectrometry (ESI⁺): m/z=444/446 [M−H]⁺ (Br)
HPLC (Method 3): Retention time=0.922 min Procedure 23

Step A

Example 23.1

6-{[5-Bromo-6-(3,3-difluoropyrrolidin-1-yl)pyridin-2-yl]methyl}-5-methyl-[1,2,4]triazolo[1,5-a]pyrimidin-7-amine

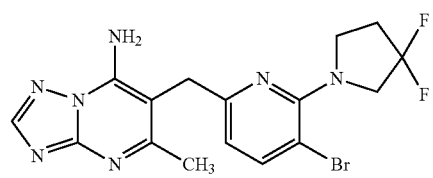 [SMILES: Cc1nc2ncnn2c(N)c1Cc1ccc(Br)c(N2CCC(F)(F)C2)n1]

A mixture of 6-[(5-bromo-6-chloropyridin-2-yl)methyl]-5-methyl-[1,2,4]triazolo[1,5-a]pyrimidin-7-amine (17.6 mg; 50.0 µmol) (see procedure 1, step F), 3,3-difluoropyrrolidine (16 mg; 150 µmol), N,N-diisopropylethylamine (25.9 µL; 150 µmol), potassium fluoride (8.7 mg; 150 µmol) and 1.2 mL 1-methylpyrrolidin-2-one is stirred overnight at 150° C. The reaction is quenched with methanol, filtered and purified by reverse phase chromatography-HPLC (modifier: ammonium hydroxide).
Yield: 9.3 mg (44% of theory)
Mass spectrometry (ESI⁺): m/z=424/426 [M+H]⁺ (Br)
HPLC (Method 8): Retention time=0.97 min.
Following examples are prepared analogously to procedure 23 starting from 6-[(5-bromo chloropyridin-2-yl)methyl]-5-methyl-[1,2,4]triazolo[1,5-a]pyrimidin-7-amine and the corresponding amine

| Example | Structure | Mass spectrometry | HPLC Retention time |
|---|---|---|---|
| 23.2 | ![structure] | (ESI⁺): m/z = 438/440 [M + H]⁺ (Br) | (Method 8): 1.00 min |

-continued

| Example | Structure | Mass spectrometry | HPLC Retention time |
|---|---|---|---|
| 23.3 | 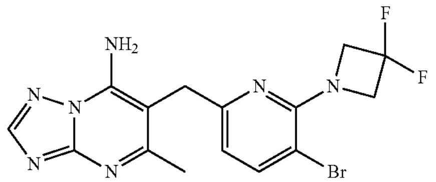 [SMILES: Cc1nc2ncnn2c(N)c1Cc1ccc(Br)c(N2CC(F)(F)C2)n1] | (ESI⁺): m/z = 410/412 [M + H]⁺ (Br) | (Method 8): 0.95 min |
| 23.4 | 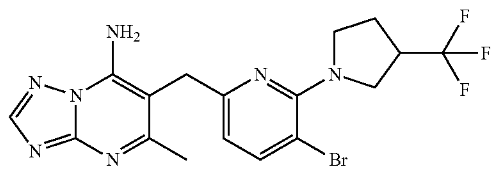 [SMILES: Cc1nc2ncnn2c(N)c1Cc1ccc(Br)c(N2CCC(C(F)(F)F)C2)n1] | (ESI⁺): m/z = 456/458 [M + H]⁺ (Br) | (Method 8): 1.04 min |
| 23.5 | 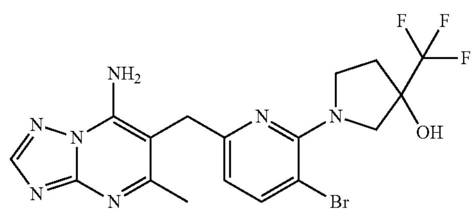 [SMILES: Cc1nc2ncnn2c(N)c1Cc1ccc(Br)c(N2CCC(O)(C(F)(F)F)C2)n1] | (ESI⁺): m/z = 472/474 [M + H]⁺ (Br) | (Method 8): 0.94 min |
| 23.6 | 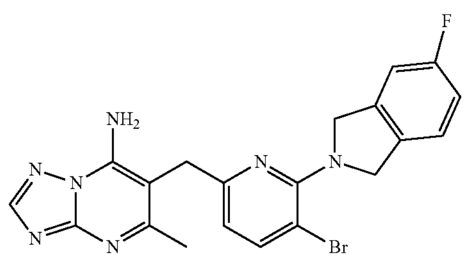 [SMILES: Cc1nc2ncnn2c(N)c1Cc1ccc(Br)c(N2Cc3ccc(F)cc3C2)n1] | (ESI⁺): m/z = 454/456 [M + H]⁺ (Br) | (Method 8): 1.08 min |
| 23.7 | 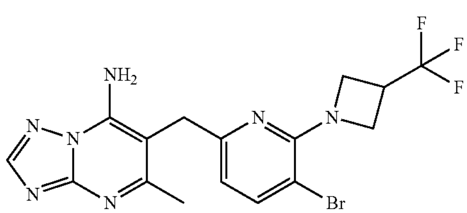 [SMILES: Cc1nc2ncnn2c(N)c1Cc1ccc(Br)c(N2CC(C(F)(F)F)C2)n1] | (ESI⁺): m/z = 442/444 [M + H]⁺ (Br) | (Method 8): 0.96 min |

Procedure 24

Step A

5-Methyl-[1,2,4]triazolo[1,5-a]pyrimidin-7-amine

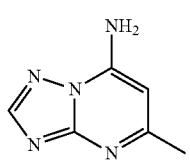

A mixture of cyanoacetone sodium salt (CAS: 70807-22-6; 3.00 g; 28.6 mmol), 1H-1,2,4-triazol-5-amine (2.53 g; 28.55 mmol) in 30 mL of acidic acid is stirred at 110° C. for 4 hours. The reaction is added to water and the mixture is stirred overnight. The precipitate is filtered off and the filtrate is concentrated under reduced pressure. The residue is dissolved in 20 mL methanol and 20 mL sodium methanolate (33% in methanol) is added. The precipitate is filtered off and dried.

Yield: 2.3 g (54% of theory)
Mass spectrometry (ESI⁺): m/z=150 [M+H]⁺
HPLC (Method 1): Retention time=0.268 min.

Step B

6-Iodo-5-methyl-[1,2,4]triazolo[1,5-a]pyrimidin-7-amine

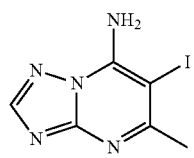

To 5-methyl-[1,2,4]triazolo[1,5-a]pyrimidin-7-amine (900 mg; 5.73 mmol) in 15 mL of acidic acid are added sodium iodide (944 mg; 5.98 mmol) and the mixture is stirred for a few minutes. N-Chloro-p-toluenesulfonamide sodium (Chloramine-T) trihydrate (2.43 g; 8.22 mmol) is added and the reaction is stirred at room temperature for 1 hour. 50 mL of ethyl acetate is added and the precipitate is filtered off and dried.

Yield: 1.45 g (92% of theory)

Mass spectrometry (ESI$^+$): m/z=276 [M+H]$^+$

HPLC (Method 3): Retention time=0.634 min.

Step C

Methyl 7-amino-5-methyl-[1,2,4]triazolo[1,5-a]pyrimidine-6-carboxylate

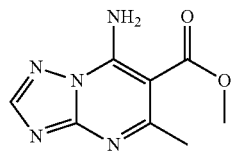

To a solution of 6-iodo-5-methyl-[1,2,4]triazolo[1,5-a]pyrimidin-7-amine (1.90 g; 6.91 mmol) in 30 mL of N,N-dimethylformamide, 30 mL of methanol and triethylamine (1.99 mL; 13.82 mmol) is added [1,1'-bis(diphenylphosphino)ferrocene]dichloropalladium (505 mg; 0.69 mmol). The reaction is stirred under a CO atmosphere at 3 bar and 60° C. for 18 hours.

[1,1'-bis(diphenylphosphino)ferrocene]dichloropalladium (505 mg; 0.69 mmol) is added and the reaction is stirred under a CO atmosphere at 3 bar and 60° C. for 18 hours. The reaction is filtered and the filtrate is concentrated under reduced pressure. The residue is purified by silica gel chromatography (eluent: dichloromethane/methanol 0→90%)

Yield: 835 mg (58% of theory)

Mass spectrometry (ESI$^+$): m/z=208 [M+H]$^+$

HPLC (Method 3): Retention time=0.632 min.

Step D

{7-Amino-5-methyl-[1,2,4]triazolo[1,5-a]pyrimidin-6-yl}methanol

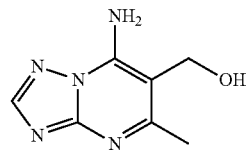

To a suspension of methyl 7-amino-5-methyl-[1,2,4]triazolo[1,5-a]pyrimidine-6-carboxylate (300 mg; 1.45 mmol) in 6 mL of tetrahydrofuran and 2 mL of toluoyl is added sodium bis(2-methoxyethoxy)aluminum hydride solution (2M in toluene, 866 μL; 2.90 mmol) and the reaction is stirred at room temperature for 18 hours. The reaction is poured into 100 mL of potassium sodium tartrate saturated aqueous solution. Ethyl acetate is added to the mixture and the precipitate is filtered off, washed with ethyl acetate and dried.

Yield: 240 mg (93% of theory)

Mass spectrometry (ESI$^+$): m/z=180 [M+H]$^+$

HPLC (Method 3): Retention time=0.218 min.

Step E

6-(Chloromethyl)-5-methyl-[1,2,4]triazolo[1,5-a]pyrimidin-7-amine

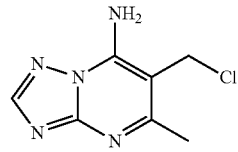

To a suspension of {7-amino-5-methyl-[1,2,4]triazolo[1,5-a]pyrimidin-6-yl}methanol (100 mg; 0.56 mmol) in 2 mL of 1-methyl-2-pyrrolidinone is added dropwise oxalyl chloride (72 μL: 0.84 mmol) and the reaction is stirred overnight at room temperature. The reaction is quenched with cooled NaHCO$_3$ (half saturated aqueous solution) and extracted two times with dichloromethane. The combined organic layers are dried and concentrated under reduced pressure. The residue is further used as crude product in step H.

Yield: 110 mg (100% of theory)

Step F

6-Iodo-3-(trifluoromethyl)pyridine-2-carbonitrile

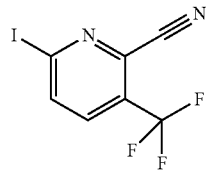 [SMILES: N#Cc1nc(I)ccc1C(F)(F)F]

6-Chloro-3-(trifluoromethyl)pyridine-2-carbonitrile (was prepared as described in US2008/275057 page 81) (0.5 g, 2.42 mmol) is dissolved in 5.0 mL acetonitrile. Sodium iodide (1.08 g, 7.26 mmol) and acetyl chloride (210 µL, 2.91 mmol) are added and the mixture is stirred at room temperature for 3.5 hours. The mixture is diluted with ethyl acetate, washed with half saturated solutions of sodium bicarbonate and sodium thiosulfate, dried and concentrated under reduced pressure. The residue is purified by recrystallization from iso-propyl alcohol.

Yield: 340 mg (47% of theory)
HPLC (Method 1): Retention time=0.97 min.

Step G 6-(Chloromagnesio)-3-(trifluoromethyl)pyridine-2-carbonitrile

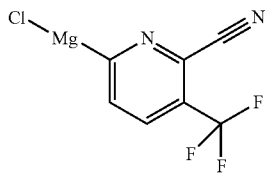

6-Iodo-3-(trifluoromethyl)pyridine-2-carbonitrile (500 mg; 1.68 mmol) in 5 mL of tetrahydrofuran is cooled to −65° C. Isopropylmagnesium chloride lithium chloride complex (1.3M solution in tetrahydrofuran) (1.46 mL; 1.90 mmol) is added dropwise at −65° C. After stirring for 10 minutes at −65° C., the mixture is further used in step H.

Yield: 0.387 mg (100% of theory)

Step H

Example 24.1

6-({7-Amino-5-methyl-[1,2,4]triazolo[1,5-a]pyrimidin-6-yl}methyl)-3-(trifluoromethyl)pyridine-2-carbonitrile

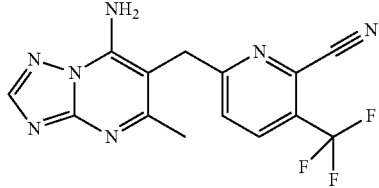 [SMILES: Cc1nc2ncnn2c(N)c1Cc1ccc(C(F)(F)F)c(C#N)n1]

6-(Chloromagnesio)-3-(trifluoromethyl)pyridine-2-carbonitrile (380 mg; 1.65 mmol) in tetrahydrofuran is cooled to −65° C. Copper(I)cyanide di(lithium chloride) complex (1.0M in tetrahydrofuran) (0.178 mL; 0.18 mmol) is added and the reaction is stirred for 5 minutes at −65° C. 6-(chloromethyl)-5-methyl-[1,2,4]triazolo[1,5-a]pyrimidin-7-amine (110 mg; 0.45 mmol) in 10 mL tetrahydrofuran is added dropwise at −65° C. and the reaction mixture is allowed to warm up to room temperature. The reaction is quenched with methanol, filtered and purified by reverse phase chromatography-HPLC (modifier: trifluoroacetic acid).

Yield: 0.39 mg (26% of theory)
Mass spectrometry (ESI$^+$): m/z=334 [M+H]$^+$
HPLC (Method 4): Retention time=0.771 min.

Procedure 25

Step A 1,3-Diethyl 2-{[2-methoxy-4-(trifluoromethyl)phenyl]methyl}propanedioate

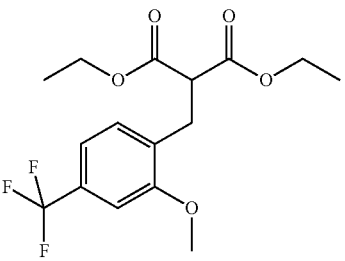 [SMILES: CCOC(=O)C(Cc1ccc(C(F)(F)F)cc1OC)C(=O)OCC]

To sodium hydride (60% dispersion in mineral oil, 500 mg; 1.86 mmol) suspended in 2 mL of N,N-dimethylformamide is added diethyl malonate (257 µL; 1.86 mmol) at 10° C. After stirring at room temperature for 1 hour, the reaction is cooled to 0° C. and 1-(bromomethyl)-2-methoxy-4-(trifluoromethyl)benzene (500 mg; 1.86 mmol) in 1 mL of N,N-dimethylformamide is added dropwise. The reaction is stirred at room temperature overnight. The reaction is purified by reverse phase chromatography-HPLC (modifier: ammonium hydroxide).

Yield: 430 mg (66% of theory)
Mass spectrometry (ESI$^+$): m/z=349 [M+H]$^+$
HPLC (Method 3): Retention time=1.184 min Step B 6-{[2-Methoxy-4-(trifluoromethyl)phenyl]methyl}-[1,2,4]triazolo[1,5-a]pyrimidine-5,7-diol

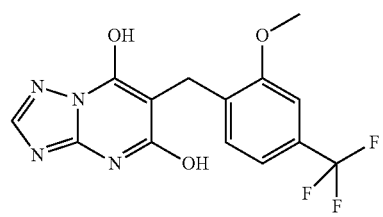 [SMILES: COc1cc(C(F)(F)F)ccc1Cc1c(O)nc2ncnn2c1O]

A mixture of 1,3-diethyl 2-{[2-methoxy-4-(trifluoromethyl)phenyl]methyl}propanedioate (200 mg; 0.57 mmol), 1H-1,2,4-triazol-3-amine (48.2 mg; 0.57 mmol) and tributylamine (150 µL; 0.63 mmol) is stirred at 150° C. overnight. The reaction is diluted with methanol and purified by reverse phase chromatography-HPLC (modifier: trifluoroacetic acid).

Yield: 73 mg (37% of theory)
Mass spectrometry (ESI$^+$): m/z=341 [M+H]$^+$
HPLC (Method 2): Retention time=0.856 min

Step C 5,7-Dichloro-6-{[2-methoxy-4-(trifluoromethyl)phenyl]methyl}-[1,2,4]triazolo[1,5-a]pyrimidine

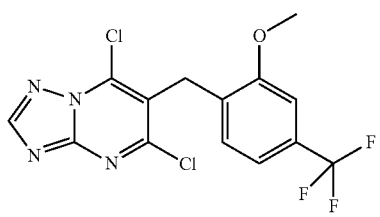 [SMILES: COc1cc(C(F)(F)F)ccc1Cc1c(Cl)nc2ncnn2c1Cl]

To 6-{[2-Methoxy-4-(trifluoromethyl)phenyl]methyl}-[1,2,4]triazolo[1,5-a]pyrimidine-5,7-diol (73 mg; 0.21 mmol) is added 3 mL phosphorus oxychloride and the reaction is stirred for 2 hours at reflux. The reaction is diluted with dichloromethane and extracted with water. The organic layer is dried and concentrated under reduced pressure. The residue is further used as crude product.

Yield: 73 mg (90% of theory)

Mass spectrometry (ESI$^+$): m/z=377/379/381 [M+H]$^+$ (Cl2)

HPLC (Method 3): Retention time=1.098 min

Step D

Example 25.1

5-Chloro-6-{[2-methoxy-4-(trifluoromethyl)phenyl]methyl}-[1,2,4]triazolo[1,5-a]pyrimidin-7-amine

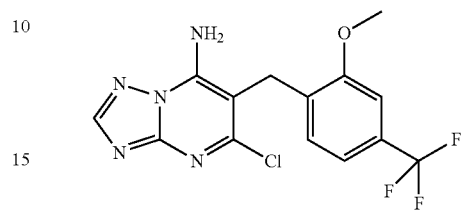

5,7-Dichloro-6-{[2-methoxy-4-(trifluoromethyl)phenyl]methyl}-[1,2,4]triazolo[1,5-a]pyrimidine (73 mg; 0.19 mmol) is dissolved in ammonia (0.5 M in dioxane) (1.29 mL; 0.65 mmol) and ammonia (7M in methanol) (0.516 mL; 3.61 mmol). The reaction is stirred in the microwave for 2 hours at 70° C. The reaction is acidified with trifluoroacetic acid and purified by reverse phase chromatography-HPLC (modifier: trifluoroacetic acid).

Yield: 16 mg (23% of theory)

Mass spectrometry (ESI$^+$): m/z=358/360 [M+H]$^+$ (Cl)

HPLC (Method 1): Retention time=0.957 min

Following examples are prepared analogously to example 25.1

| Example | Structure | Mass spectrometry | HPLC Retention time | Starting material Step A bromide |
|---|---|---|---|---|
| 25.2 | (NH$_2$, OMe, CF$_3$ substituted triazolopyrimidine) | (ESI$^+$): m/z = 358/360 [M + H]$^+$ (Cl) | (Method 2): 0.98 min | 4-(bromomethyl)-2-methoxy-1-(trifluoromethyl)benzene |
| 25.3 | (NH$_2$, CF$_3$ substituted triazolopyrimidine) | (ESI$^+$): m/z = 328/330 [M + H]$^+$ (Cl) | (Method 3): 0.976 min | 1-(bromomethyl)-4-(trifluoromethyl)benzene |

The invention claimed is:
1. A compound of formula

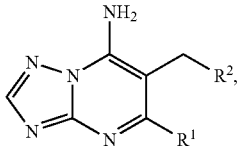
(I)

wherein
R$^1$ is Cl, Br, CN or CH$_3$,
wherein the CH$_3$ group is optionally substituted with 1, 2, or 3 F or with one OH;
R$^2$ is phenyl or pyridinyl,
wherein each phenyl or pyridinyl is substituted with one fluoro-containing substituent R$^3$ selected from the group consisting of:
(a) C$_{1-6}$-alkyl, which is substituted with one or more F;
(b) C$_{3-7}$-cycloalkyl, which is substituted with one or more F and optionally additionally substituted with one CN;
(c) —O—(C$_{1-6}$-alkyl), which is substituted with one or more F;
(d) —O—(C$_{1-3}$-alkyl)-(C$_{3-7}$-cycloalkyl), which is substituted in the cycloalkyl moiety with one or more F and/or with one mono- or polyfluorinated C$_{1-3}$-alkyl group;
(e) —S—(C$_{1-3}$-alkyl), which is substituted with one or more F;
(f) —S(=O)—(C$_{1-3}$-alkyl), which is substituted with one or more F;
(g) —SO$_2$—(C$_{1-3}$-alkyl), which is substituted with one or more F;
(h) —NH—(C$_{1-3}$-alkyl), which is substituted with one or more F;
(i) —NH—(C$_{1-4}$-alkyl)-(C$_{3-7}$-cycloalkyl), which is substituted in the cycloalkyl moiety with one or more F;
(j) —NH—(C$_{3-7}$-cycloalkyl), which is substituted in the cycloalkyl moiety with one or more F;
(k) —C(=O)—O—(C$_{1-4}$-alkyl), which is substituted with one or more F;
(l) heterocyclyl, which is substituted with one or more F and/or with one mono- or polyfluorinated C$_{1-3}$-alkyl group and which may additionally be substituted with one OH;
(m) heteroaryl, which is substituted with one or more F and/or with one mono- or polyfluorinated C$_{1-3}$-alkyl group and which may additionally be substituted with one C$_{1-3}$-alkyl group;
wherein each heterocyclyl R$^3$ group in (l) is selected from the group consisting of a 4- to 7-membered monocyclic cycloalkyl group, in which 1, 2 or 3 CH$_2$-groups are independently of each other replaced by O, S, NH or C=O; and
wherein a phenyl ring may be condensated to any 5- to 7-membered heterocyclic R$^3$ group in (l); and
wherein each heteroaryl R$^3$ group in (m) is selected from the group consisting of a 5-membered aromatic cycle containing 1, 2 or 3 heteroatoms independently selected from the group consisting of N, O and S or from a 6-membered aromatic cycle containing 1 or 2 N;
and wherein each phenyl or pyridinyl of the group R$^2$ may additionally be substituted with 1 or 2 substituents R$^4$ independently of each other selected from the group consisting of:
F, Cl, Br, I, CN, C$_{1-6}$-alkyl, C$_{3-7}$-cycloalkyl, OH, —O—(C$_{1-6}$-alkyl), —O—(C$_{1-3}$-alkyl)-(C$_{3-7}$-cycloalkyl), —O—(C$_{1-3}$-alkyl)-heterocyclyl, —O—(C$_{3-7}$-cycloalkyl), —O-heterocyclyl, —S—(C$_{1-3}$-alkyl), —SO—(C$_{1-3}$-alkyl), —SO$_2$—(C$_{1-3}$-alkyl), —C(=O)—NH$_2$, —C(=O)—NH(C$_{1-3}$-alkyl), —C(=O)—N(C$_{1-3}$-alkyl)$_2$, —C(=O) OH, —C(=O)—O—(C$_{1-4}$-alkyl), —NH$_2$, —NH—(C$_{1-4}$-alkyl), —NH—(C$_{1-4}$-alkyl)-(C$_{3-7}$-cycloalkyl), —NH—(C$_{3-7}$-cycloalkyl), —N=S(=O)(C$_{1-3}$-alkyl)$_2$, heterocyclyl and heteroaryl,
wherein the alkyl groups of the —N=S(=O)(C$_{1-3}$-alkyl)$_2$ of the group R$^4$ may be linked and together with the S atom, to which they are attached, form a 4-7-membered thio-heterocycle,
wherein each C$_{1-3}$-alkyl, C$_{1-4}$-alkyl and C$_{1-6}$-alkyl group in the C$_{1-6}$-alkyl, —O—(C$_{1-6}$-alkyl), —O—(C$_{1-3}$-alkyl)-(C$_{3-7}$-cycloalkyl), —O—(C$_{1-3}$-alkyl)-heterocyclyl, —S—(C$_{1-3}$-alkyl), —SO—(C$_{1-3}$-alkyl), —SO$_2$—(C$_{1-3}$-alkyl), —C(=O)—NH(C$_{1-3}$-alkyl), —C(=O)—N(C$_{1-3}$-alkyl)$_2$, —C(=O)—O—(C$_{1-4}$-alkyl), —NH—(C$_{1-4}$-alkyl), —NH—(C$_{1-4}$-alkyl)-(C$_{3-7}$-cycloalkyl), and —N=S(=O)(C$_{1-3}$-alkyl)$_2$ of the group of R$^4$ is optionally substituted with 1, 2 or 3 F or with one OH, CN, COOH or —C(=O)—NH$_2$;
wherein each C$_{3-7}$-cycloalkyl, —O—(C$_{1-3}$-alkyl)-(C$_{3-7}$-cycloalkyl), —O—(C$_{3-7}$-cycloalkyl), —NH—(C$_{1-4}$-alkyl)-(C$_{3-7}$-cycloalkyl), and —NH—(C$_{3-7}$-cycloalkyl) R$^4$ group is optionally substituted with one or two F and/or with one CN or —CH$_3$, which —CH$_3$ is optionally substituted with 1, 2 or 3 F;
wherein the heterocyclyl of the —O—(C$_{1-3}$-alkyl)-heterocyclyl, —O-heterocyclyl, and heterocyclyl group of R$^4$ is selected from the group consisting of a mono- or spirocyclic 4-to 7-membered cycloalkyl group, in which 1, 2 or 3 CH$_2$-groups of the 4- to 7-membered cycloalkyl group are independently of each other replaced by O, S, NH or C=O,
wherein the heterocyclyl of the —O—(C$_{1-3}$-alkyl)-heterocyclyl, —O-heterocyclyl, and heterocyclyl group of R$^4$ is optionally substituted with 1 to 3 substituents independently of each other selected from the group consisting of F, CN, OH and C$_{1-3}$-alkyl, wherein the C$_{1-3}$-alkyl is optionally substituted with one or more F; and
wherein the heteroaryl group of R$^4$ is selected from the group consisting of a 5-membered aromatic cycle containing 1, 2 or 3 heteroatoms independently selected from the group consisting of N, O and S or from a 6-membered aromatic cycle containing 1 or 2 N, and
wherein the heteroaryl group of R$^4$ is optionally substituted with 1 or 2 substituents independently of each other selected from the group consisting of F, CN and C$_{1-3}$-alkyl, which C$_{1-3}$-alkyl is optionally substituted with one or more F;
or a pharmaceutically acceptable salt thereof.
2. A pharmaceutically acceptable salt of a compound according to claim 1.

3. The compound of formula (I) according to claim 1, or a pharmaceutically acceptable salt thereof, wherein
$R^1$ is $C_1$, $CH_3$, $-CH_2F$, $-CHF_2$ or $CF_3$; and
$R^2$ is

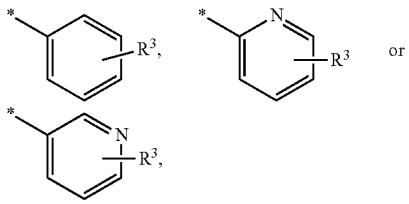

wherein each $R^2$ group may additionally be substituted by one or two substituents $R^4$.

4. The compound of formula (I) according to claim 3, or a pharmaceutically acceptable salt thereof, wherein $R^3$ is selected from the group consisting of:
(a) $C_{1-3}$-alkyl, which is substituted with one or more F;
(b) $C_{3-6}$-cycloalkyl, which is substituted with one or more F and optionally additionally substituted with one CN;
(c) $-O-(C_{1-4}$-alkyl), which is substituted with one or more F;
(d) $-O-CH_2-(C_{3-6}$-cycloalkyl), which is substituted in the cycloalkyl moiety with one or more F and/or with one mono- or polyfluorinated $C_{1-3}$-alkyl group;
(e) $-S-(C_{1-3}$-alkyl), which is substituted with one or more F;
(f) $-S(=O)-(C_{1-3}$-alkyl), which is substituted with one or more F;
(g) $-SO_2-(C_{1-3}$-alkyl), which is substituted with one or more F;
(h) $-NH-(C_{1-3}$-alkyl), which is substituted with one or more F;
(i) $-NH-CH_2-(C_{3-6}$-cycloalkyl), which is substituted in the cycloalkyl moiety with one or more F;
(j) $-NH-(C_{3-6}$-cycloalkyl), which is substituted in the cycloalkyl moiety with one or more F;
(k) $-C(=O)-O-(C_{1-4}$-alkyl), which is substituted with one or more F;
(l) heterocyclyl, which is substituted with one or more F and/or with one mono- or polyfluorinated $C_{1-3}$-alkyl group and which may additionally be substituted with one OH;
(m) heteroaryl, which is substituted with one or more F and/or with one mono- or polyfluorinated $C_{1-3}$-alkyl group and which may additionally be substituted with one $C_{1-3}$-alkyl group;
wherein each heterocyclyl $R^3$ group in (l) is selected from the group consisting of oxetanyl, tetrahydrofuranyl, tetrahydropyranyl, azetidinyl, pyrrolidinyl, piperidinyl, piperazinyl, morpholinyl and 2,3-dihydro-1H-isoindolyl; and
wherein each heteroaryl $R^3$ group in (m) is selected from the group consisting of a 5-membered aromatic cycle containing 1 or 2 heteroatoms independently selected from the group consisting of N, O and S.

5. The compound of formula (I) according to claim 4, or a pharmaceutically acceptable salt thereof, wherein $R^3$ is
$-CF_3$, $-CHF_2$, $-CH_2F$, $-O-CF_3$, $-O-CHF_2$, $-O-CH_2F$, $-O-CH_2-CH_2-F$, $-O-CH_2-CHF_2$, $-O-CH_2-CF_3$, $-O-CH_2-CH_2-CH_2-F$, $-O-CH_2-CH_2-CF_3$, $-S-CF_3$,

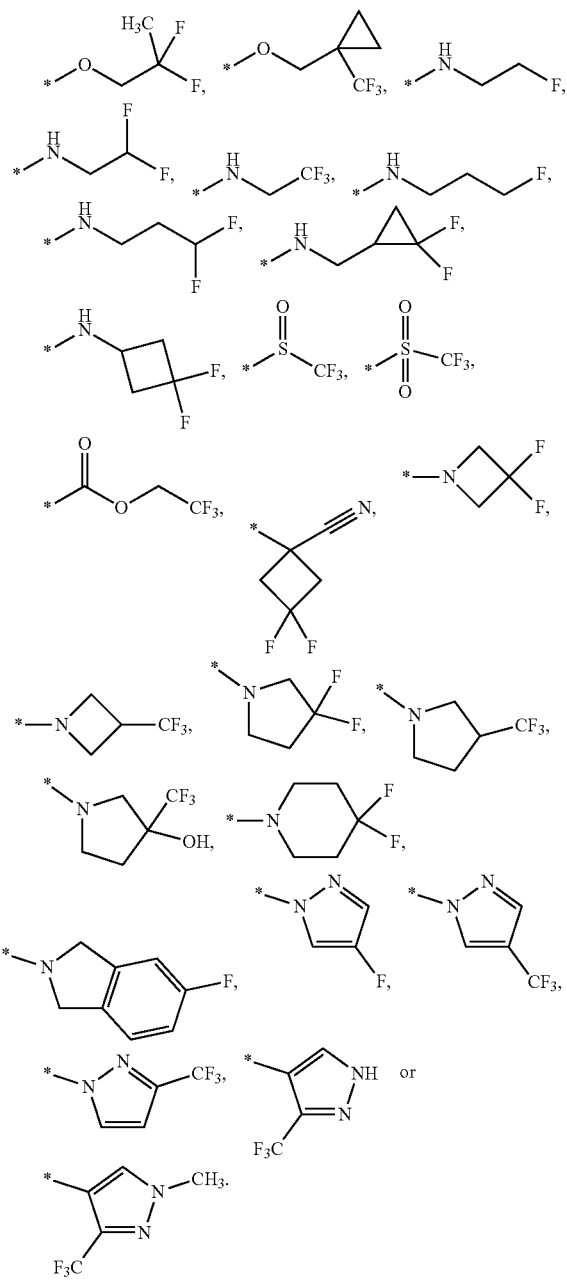

6. The compound of formula (I) according to claim 1, or a pharmaceutically acceptable salt thereof, wherein $R^4$ is independently of each other selected from the group consisting of:
F, Cl, Br, I, CN, $-O-(C_{1-6}$-alkyl), $-O-(C_{3-7}$-cycloalkyl), $-C(=O)-NH_2$, $-C(=O)-NH(C_{1-3}$-alkyl), $-C(=O)-N(C_{1-3}$-alkyl)$_2$, $-C(=O)-O-(C_{1-4}$-alkyl), $-NH_2$, $-N=S(=O)(C_{1-3}$-alkyl)$_2$, heterocyclyl and heteroaryl,
wherein the alkyl groups of the $-N=S(=O)(C_{1-3}$-alkyl)$_2$ group of $R^4$ may be linked and together with the S atom, to which they are attached, form a 4-7-membered thio-heterocycle,
wherein each $C_{1-3}$-alkyl, $C_{1-4}$-alkyl and $C_{1-6}$-alkyl group of $R^4$ in the $C_{1-6}$-alkyl, $-O-(C_{1-6}$-alkyl), $-C(=O)-NH(C_{1-3}$-alkyl), $-C(=O)-N(C_{1-3}$ alkyl)$_2$, —C(=O)—O—(C$_{1-4}$-alkyl), and —N=S(=O)(C$_{1-3}$-alkyl)$_2$ R$^4$ group is optionally substituted with 1, 2 or 3 F;

wherein the heterocyclyl group of R$^4$ is selected from the group consisting of oxetanyl, tetrahydrofuranyl, tetrahydropyranyl, azetidinyl, pyrrolidinyl, piperidinyl, piperazinyl and morpholinyl;

wherein the heteroaryl group of R$^4$ is selected from the group consisting of a 5-membered aromatic cycle containing 1 or 2 heteroatoms independently selected from the group consisting of N, O and S.

7. The compound of formula (I) according to claim 1, or a pharmaceutically acceptable salt thereof, wherein R$^4$ is independently of each other selected from the group consisting of:

F, Cl, Br, I, CN, C$_{1-3}$-alkyl, —O—(C$_{1-3}$-alkyl), —O-cyclobutyl, —C(=O)—NH$_2$, —C(=O)—NH(C$_{1-3}$-alkyl), —C(=O)—N(C$_{1-3}$-alkyl)$_2$, —C(=O)—O—(C$_{1-3}$-alkyl), —NH$_2$, —N=S(=O)(CH$_3$)$_2$, heterocyclyl and heteroaryl, wherein each C$_{1-3}$-alkyl group in the C$_{1-3}$-alkyl, —O—(C$_{1-3}$-alkyl), —C(=O)—NH(C$_{1-3}$-alkyl), —C(=O)—N(C$_{1-3}$-alkyl)$_2$, and —C(=O)—O—(C$_{1-3}$-alkyl) group of R$^4$ is optionally substituted with 1, 2, or 3 F;

wherein the heterocyclyl group of R$^4$ is selected from the group consisting of oxetanyl, tetrahydrofuranyl, tetrahydropyranyl, azetidinyl, pyrrolidinyl, piperidinyl, piperazinyl and morpholinyl;

wherein the heteroaryl group of R$^4$ is selected from the group consisting of furanyl, thienyl, pyrazolyl, imidazolyl, oxazolyl, isoxazolyl, thiazolyl and isothiazolyl.

8. The compound according to claim 1 having the following structure:

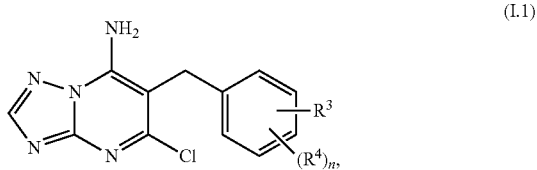

(I.1)

wherein
R$^1$ is CH$_3$ or Cl;
n is 0 or 1;
R$^3$ is —CF$_3$, —CHF$_2$, —CH$_2$F, —O—CF$_3$, —O—CHF$_2$, —O—CH$_2$F, —O—CH$_2$—CH$_2$—F, —O—CH$_2$—CHF$_2$, —O—CH$_2$—CF$_3$, —O—CH$_2$—CH$_2$—CH$_2$—F, —O—CH$_2$—CH$_2$—CF$_3$, —S—CF$_3$,

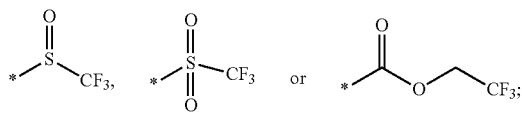 [SMILES: *S(=O)C(F)(F)F ; *S(=O)(=O)C(F)(F)F ; *C(=O)OCC(F)(F)F]

and
R$^4$ is F, Cl, Br, I, CN, C$_{1-3}$-alkyl, —O—(C$_{1-3}$-alkyl), —C(=O)—NH$_2$, —C(=O)—NH(C$_{1-3}$-alkyl), —C(=O)—N(C$_{1-3}$-alkyl)$_2$, —C(=O)—O—(C$_{1-3}$-alkyl), —N=S(=O)(CH$_3$)$_2$, heterocyclyl or heteroaryl, wherein each CH$_3$ and C$_{1-3}$-alkyl in the C$_{1-3}$-alkyl, —O—(C$_{1-3}$-alkyl), —C(=O)—NH(C$_{1-3}$-alkyl), —C(=O)—N(C$_{1-3}$-alkyl)$_2$, —C(=O)—O—(C$_{1-3}$-alkyl), and —N=S(=O)(CH$_3$)$_2$ group of R$^4$ is optionally substituted with 1, 2, or 3 F;

wherein the heterocyclyl group of R$^4$ is selected from the group consisting of oxetanyl, tetrahydrofuranyl, tetrahydropyranyl, azetidinyl, pyrrolidinyl, piperidinyl, piperazinyl and morpholinyl;

wherein the heteroaryl group of R$^4$ is selected from the group consisting of furanyl, thienyl, pyrazolyl, imidazolyl, oxazolyl, isoxazolyl, thiazolyl and isothiazolyl;

or a pharmaceutically acceptable salt thereof.

9. The compound according to claim 1 having the following structure:

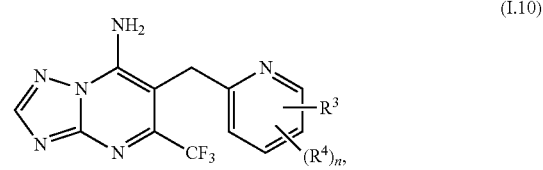

(I.10)

wherein
n is 0 or 1;
R$^3$ is:
(a) C$_{1-3}$-alkyl, which is substituted with 1, 2, or 3 F;
(c) —O—(C$_{1-3}$-alkyl), which is substituted with 1, 2, or 3 F;
(d) —O—CH$_2$-cyclopropyl, which is substituted in the cyclopropyl moiety with one or two F and/or with one CF$_3$ group;
(h) —NH—(C$_{1-3}$-alkyl), which is substituted with 1, 2, or 3 F;
(i) —NH—CH$_2$-cyclopropyl, which is substituted in the cyclopropyl moiety with one or two F;
(j) —NH-cyclobutyl, which is substituted in the cyclobutyl moiety with one or two F;
(l) heterocyclyl, which is substituted with one or two F and/or with one CF$_3$ group and which may additionally be substituted with one OH; or
(m) heteroaryl, which is substituted with one F and/or with one CF$_3$ group and which may additionally be substituted with one CH$_3$ group;
wherein the heterocyclyl group of R$^3$ is selected from the group consisting of oxetanyl, tetrahydrofuranyl, tetrahydropyranyl, azetidinyl, pyrrolidinyl, piperidinyl, piperazinyl and morpholinyl; and
wherein the heteroaryl group of R$^3$ is selected from the group consisting of furanyl, thienyl, pyrazolyl, imidazolyl, oxazolyl, isoxazolyl, thiazolyl and isothiazolyl; and R$^4$ is F, Cl, Br, I, CN, C$_{1-3}$-alkyl, —O—(C$_{1-3}$-alkyl), —NH$_2$, heterocyclyl or heteroaryl,
wherein each C$_{1-3}$-alkyl group in the C$_{1-3}$-alkyl and —O—(C$_{1-3}$-alkyl) group of R$^4$ is optionally substituted with 1, 2, or 3 F;

wherein the heterocyclyl group of R$^4$ is selected from the group consisting of oxetanyl, tetrahydrofuranyl, tetrahydropyranyl, azetidinyl, pyrrolidinyl, piperidinyl, piperazinyl and morpholinyl;

wherein the heteroaryl group of R$^4$ group is selected from the group consisting of furanyl, thienyl, pyrazolyl, imidazolyl, oxazolyl, isoxazolyl, thiazolyl and isothiazolyl;

or a pharmaceutically acceptable salt thereof.

10. The compound according to claim 1, wherein the compound is selected from the group consisting of:
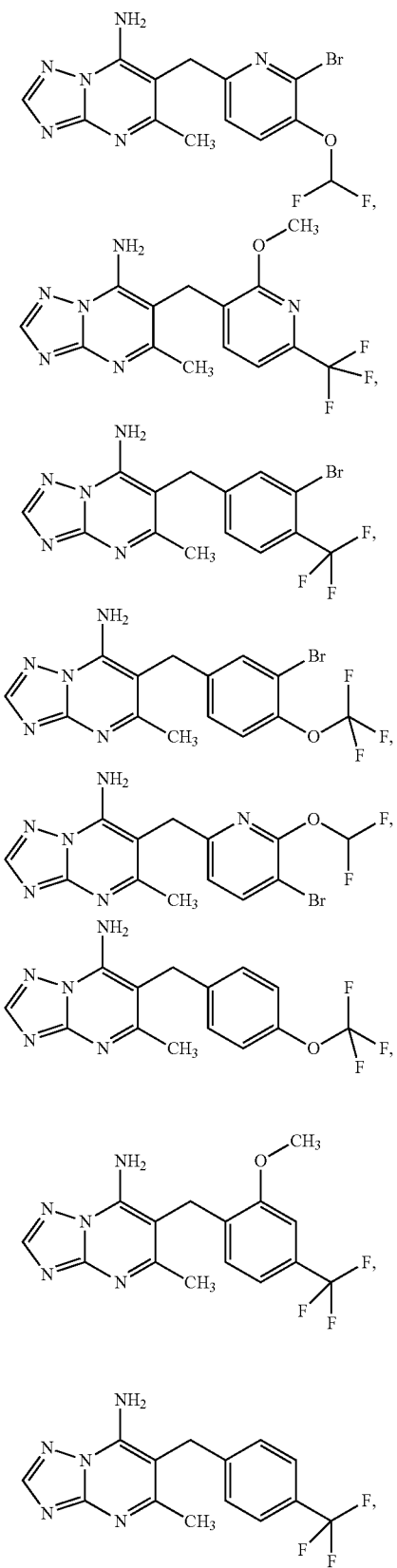
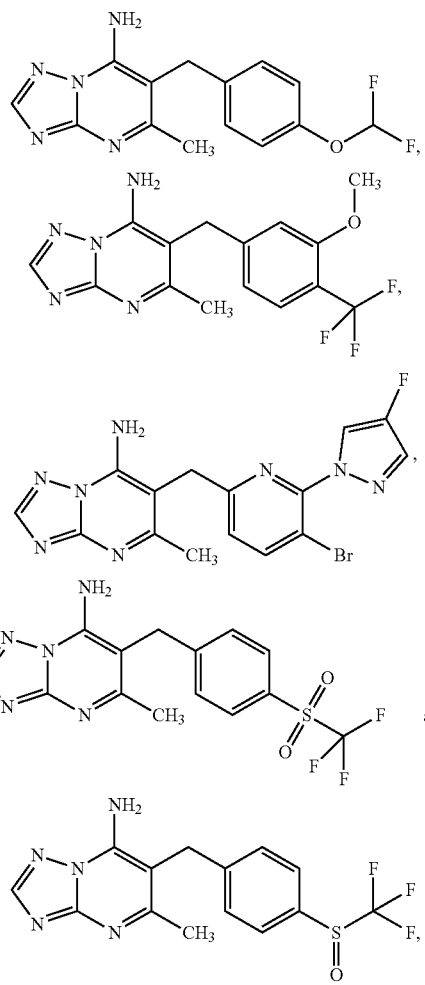
or a pharmaceutically acceptable salt thereof.
11. The compound according to claim 10, wherein the compound is:
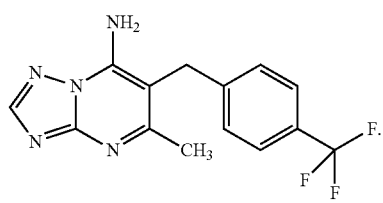 [SMILES: Cc1nc2ncnn2c(N)c1Cc1ccc(C(F)(F)F)cc1]
12. The compound according to claim 10, wherein the compound is:
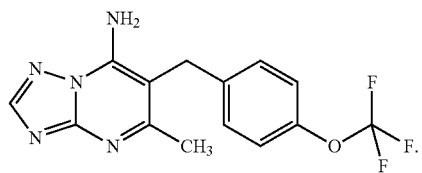 [SMILES: Cc1nc2ncnn2c(N)c1Cc1ccc(OC(F)(F)F)cc1]

13. The compound according to claim 10, wherein the compound is:

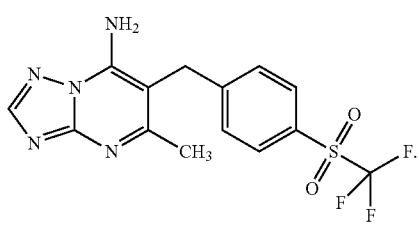 [SMILES: Cc1nc2ncnn2c(N)c1Cc1ccc(S(=O)(=O)C(F)(F)F)cc1]

14. The compound according to claim 10, wherein the compound is:

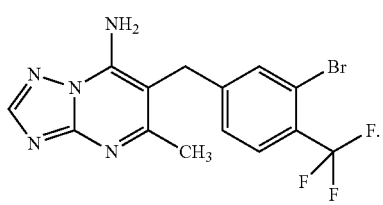 [SMILES: Cc1nc2ncnn2c(N)c1Cc1ccc(C(F)(F)F)c(Br)c1]

15. The compound according to claim 10, wherein the compound is:

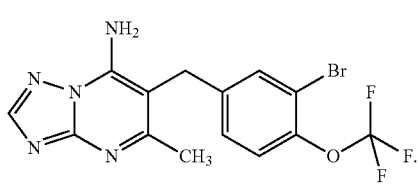 [SMILES: Cc1nc2ncnn2c(N)c1Cc1ccc(OC(F)(F)F)c(Br)c1]

16. The compound according to claim 10, wherein the compound is:

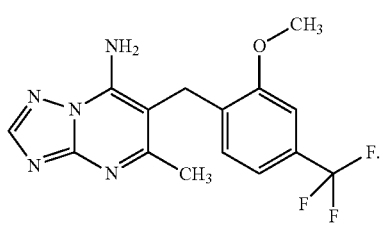 [SMILES: COc1cc(C(F)(F)F)ccc1Cc1c(C)nc2ncnn2c1N]

17. The compound according to claim 10, wherein the compound is:

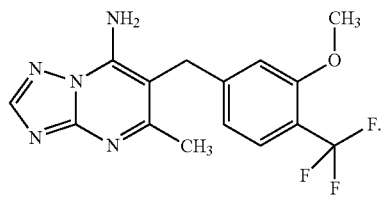 [SMILES: COc1cc(Cc2c(C)nc3ncnn3c2N)ccc1C(F)(F)F]

18. The compound according to claim 10, wherein the compound is:

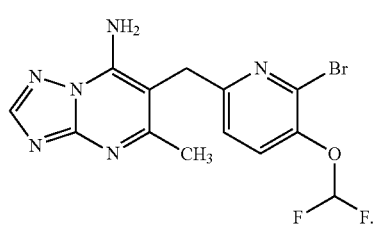 [SMILES: Cc1nc2ncnn2c(N)c1Cc1ccc(OC(F)F)c(Br)n1]

19. The compound according to claim 10, wherein the compound is:

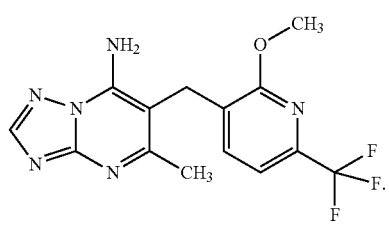 [SMILES: COc1nc(C(F)(F)F)ccc1Cc1c(C)nc2ncnn2c1N]

20. A pharmaceutical composition comprising a compound according to claim 1, or a pharmaceutically acceptable salt thereof, and one or more inert carriers and/or diluents.

21. The pharmaceutical composition according to claim 20 wherein the pharmaceutical composition comprises one or more additional therapeutic agents.

22. A method for inhibiting the activity of ghrelin O-acyl transferase in a patient, wherein the method comprising administering to the patient in need thereof a pharmaceutically effective amount of a compound of claim 1, or a pharmaceutically acceptable salt thereof.

23. The method according to claim 22, wherein the patient has a disease or condition selected from the group consisting of insulin resistance, obesity, and type 2 diabetes mellitus.

* * * * *